US009655961B2

(12) United States Patent
Tangy et al.

(10) Patent No.: US 9,655,961 B2
(45) Date of Patent: May 23, 2017

(54) RECOMBINANT MEASLES VIRUS EXPRESSING CHIKUNGUNYA VIRUS POLYPEPTIDES AND THEIR APPLICATIONS

(71) Applicants: INSTITUT PASTEUR, Paris (FR); Themis Bioscience GMBH, Vienna (AT); CENTRE NATIONAL DE LA RECHERCHE SCIENTIFIQUE, Paris (FR)

(72) Inventors: Frederic Tangy, Les Lilas (FR); Samantha Brandler, Bouguenais (FR); Philippe Despres, Sant-Denis La Reunion (FR); Andre Habel, Hamburg (FR)

(73) Assignees: INSTITUT PASTEUR, Paris (FR); THEMIS BIOSCIENCE GMBH, Vienna (AT); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/430,975

(22) PCT Filed: Sep. 26, 2013

(86) PCT No.: PCT/EP2013/070137
§ 371 (c)(1),
(2) Date: Mar. 25, 2015

(87) PCT Pub. No.: WO2014/049094
PCT Pub. Date: Apr. 3, 2014

(65) Prior Publication Data
US 2015/0238592 A1  Aug. 27, 2015

(30) Foreign Application Priority Data
Sep. 27, 2012  (EP) .................................. 12306176

(51) Int. Cl.
| | | |
|---|---|---|
| C07K 14/02 | (2006.01) | |
| A61K 39/12 | (2006.01) | |
| C07K 14/005 | (2006.01) | |
| C12N 7/00 | (2006.01) | |
| C12N 15/86 | (2006.01) | |
| A61K 39/00 | (2006.01) | |
| A61K 38/00 | (2006.01) | |

(52) U.S. Cl.
CPC ............ *A61K 39/12* (2013.01); *C07K 14/005* (2013.01); *C12N 7/00* (2013.01); *C12N 15/86* (2013.01); *A61K 38/00* (2013.01); *A61K 2039/5254* (2013.01); *A61K 2039/5256* (2013.01); *A61K 2039/5258* (2013.01); *A61K 2039/70* (2013.01); *C12N 2760/18421* (2013.01); *C12N 2760/18434* (2013.01); *C12N 2760/18443* (2013.01); *C12N 2760/18444* (2013.01); *C12N 2770/36122* (2013.01); *C12N 2770/36123* (2013.01); *C12N 2770/36134* (2013.01)

(58) Field of Classification Search
CPC .......... C12N 2730/10134; C12N 2730/10141; C12N 15/11; C12N 2750/14162; C12N 2760/12034; C12N 2760/14234; C12N 2760/18134; C12N 2760/20134; C12N 2770/20034; C12N 2800/24; C12N 2800/30; C12N 2501/335; C12N 9/1276; C12N 15/86; C12N 2760/18444; C12N 2770/36123; C12N 2770/36134; C07K 16/10; C07K 16/1027; C07K 14/005; C07K 14/1825; C07D 211/62; C07D 241/36; G01N 2458/00; A61K 39/165; A61K 2039/53; A61K 39/00; A61K 2039/70; A61K 39/12; C12Q 2600/156; C12Q 1/707
See application file for complete search history.

(56) References Cited

U.S. PATENT DOCUMENTS

| | | | | |
|---|---|---|---|---|
| 8,852,609 B2 * | 10/2014 | Weiner | ................ | C07K 14/005 424/218.1 |
| 8,961,995 B2 * | 2/2015 | Frolov | ................... | C12N 15/86 424/184.1 |
| 9,249,191 B2 * | 2/2016 | Ueno | ................... | C07K 14/005 |

FOREIGN PATENT DOCUMENTS

| | | |
|---|---|---|
| CN | 102321639 A1 | 1/2012 |
| WO | 2004/000876 A1 | 12/2003 |
| WO | 2007/105111 A2 | 9/2007 |

OTHER PUBLICATIONS

Spielhofer et al. J. Virol. 1998, vol. 72, No. 3, pp. 2150-2159.*
Li et al. J. Virol. 2012, vol. 86, No. 16, pp. 8904-8905.*

(Continued)

*Primary Examiner* — Bao Li
(74) *Attorney, Agent, or Firm* — Arrigo, Lee & Guttman LLP

(57) ABSTRACT

The invention relates to recombinant Measles virus expressing Chikungunya virus polypeptides, and concerns in particular virus like particles (VLP) that contain envelope and capsid proteins of a Chikungunya virus at their surface. These particles are recombinant infectious particles able to replicate in a host after an administration. The invention provides means, in particular nucleic acids, vectors, cells and rescue systems to produce these recombinant infectious particles. The invention also relates to the use of these recombinant infectious particles, in particular under the form of a composition, more particularly in a vaccine formulation, for the treatment or prevention of an infection by Chikungunya virus.

20 Claims, 11 Drawing Sheets

(56) References Cited

OTHER PUBLICATIONS

Kolakofsky et al. Journal of Virology, 1998, vol. 72, No. 2, pp. 891-899.*

Brandle et al. Comparative Immunology, Microbiology & Infectious Disease 2008, vol. 31, pp. 271-291.*

Wataru Akahata et al: "A virus-like particle vaccine for epidemic Chikungunya virus protects nonhuman primates against infection", Nature Medicine, Nature Publishing Group, GB, vol. 16, No. 3, Mar. 1, 2010 (Mar. 1, 2010), pp. 334-338.

Karthik Mallilankaraman et al: "A DNA Vaccine against Chikungunya Virus is Protective in Mice and Induces Neutralizing Antibodies in Mice and Nonhuman Primates", PLOS Neglected Tropical Diseases, vol. 5, No. 1, Jan. 1, 2011 (Jan. 1, 2011), pp. e928-e928.

Muthumani K et al: "Immunogenicity of novel consensus-based DNA vaccines against Chikungunya virus", Vaccine, Elsevier Ltd, GB, vol. 26, No. 40, Sep. 19, 2008 (Sep. 19, 2008), pp. 5128-5134.

Wang E et al: "Chimeric alphavirus vaccine candidates for chikungunya", Vaccine, Elsevier Ltd, GB, vol. 26, No. 39, Sep. 15, 2008 (Sep. 15, 2008), pp. 5030-5039.

Combredet C et al: "A Molecularly Clones Schwarz Strain of Measles Virus Vaccine Induces Strong Immune Responses in Macaques and Transgenic Mice", Journal of Virology, The American Society for Microbiology, US, vol. 77, No. 21, Nov. 1, 2003 (Nov. 1, 2003), pp. 11546-11554.

Akahata, Wataru, et al., "A Specific Domain of the Chikungunya Virus E2 Protein Regulates Particle Formation in Human Cells: Implications for Alphavirus Vaccine Design," Journal of Virology, vol. 86, No. 16, pp. 8879-83 (2012).

Brandler, Samantha, et al., "A recombinant Measles Vaccine Expressing Chikungunya Virus-Like Particles is Strongly Immunogenic and Protects Mice From Lethal Challenge With Chikungunya Virus," Vaccine, vol. 31, pp. 3718-3725 (2013).

* cited by examiner

FIGURE 1A

Rescue of recombinant MV expressing CHIKV VLP

FIGURE 1B

MV-CE3E26KE1   MV-sE2   MV-sE2-Δstem

SLAIPVMCLLANTTFPCSQDNFNVYKATRPYLAHCPDCGEGHSCHSPVAL
ERIRNEATDGTLKIQVSLQIGIKTDDSHDWTKLRYMDNHMPADAERAGLF
VRTSAPCTITGTMGHFILARCPKGETLTVGFTDSRKISHSCTHPFHHDPP
VIGRE*

2 10⁴ TCID50 (I.P)   2 10⁴ TCID50

MV-CE3E2E1    MV-CE3E2E1    100 pfu
MV-sE2        MV-sE2        CHIK.06-49
MV            MV            I.P.

$10^5$ TCID50 I.P

MV-CE3E2E1
or MV 100 pfu
CHIK.06-49
I.P.

Pooled sera
from MV-CE3E2E1
MV
Or anti-CHIKV HMAF
20µl+ 80µl PBS

Pooled sera    Pooled sera    100 pfu CHIK.06-49 I.P.    Pooled sera 0h    16h    24h    36h

FIGURE 13

- MV-CHIKV
- MV
- CHIKV HMAF

Percent surviving mice vs Days post-challenge

MV-Schw

21/07/11

MV-CE3E26KE1

22/08/11

MV-CE3E26KE1

21/09/11
Challenge 100 PFU CHKV 3 months

RECOMBINANT MEASLES VIRUS EXPRESSING CHIKUNGUNYA VIRUS POLYPEPTIDES AND THEIR APPLICATIONS

SEQUENCE LISTING

The instant application contains a Sequence Listing which has been submitted in ASCII format via EFS-Web and is hereby incorporated by reference in its entirety. Said ASCII copy, created on Jan. 12, 2015, is named B09995A_Listing.txt and is 278,731 bytes in size.

FIELD OF THE INVENTION

The invention is directed to recombinant Measles virus expressing Chikungunya virus polypeptides, and concerns in particular virus like particles (VLP) that contain envelope and capsid proteins of a Chikungunya virus at their surface. These particles are recombinant infectious particles able to replicate in a host after an administration. The invention provides means, in particular nucleic acids, vectors, cells and rescue systems to produce these recombinant infectious particles. The invention also relates to the use of these recombinant infectious particles, in particular under the form of a composition, more particularly in a vaccine formulation, for the treatment or prevention of an infection by Chikungunya virus.

BACKGROUND OF THE INVENTION

Chikungunya virus (CHIKV) is a positive-strand RNA virus of the genus *Alphavirus* within the family of Togaviridae, first isolated in Tanzania in 1952.

Infection by this virus causes human disease that is characterized by symptoms similar to dengue fever, with an acute febrile phase during two to five days, followed by a prolonged arthralgic disease that affects the joints of the extremities. CHIKV is endemic in Africa, India and South-East Asia and is transmitted by Aedes mosquitoes through an urban or sylvatic transmission cycle. In 2006, an outbreak of CHIKV fever occurred in numerous islands of the Indian Ocean (the Comoros, Mauritius, Seychelles, Madagascar, Reunion island . . . ), before jumping to India where an estimated 1.4 million cases have been reported. More recently, imported infections have been described in Europe, and around 200 endemic cases have been reported in Italy (Jose, J. et al., A structural and functional perspective of alphavirus replication and assembly. Future Microbiol, 2009. 4(7): p. 837-56). Clinically, this CHIKV epidemic was accompanied by more severe symptoms than previous outbreaks, with reports of severe polyarthralgia and myalgia, complications and deaths.

The CHIKV genome is an 11.8 kb, single-stranded RNA molecule of positive polarity. This virus is closely related to Semliki Forest virus (SFV), Sindbis virus (SINV), and other Old-World alphaviruses, and more distantly related to New-World alphaviruses like Venezuelan equine encephalitis virus (Griffin, D. E., Alphaviruses, in Fields Virology, 5th ed., D. M. Knipe, Editor 2007, Wolters Kluwer, Lippincott Williams & Wilkins. p. 1023-1067). The genomic RNA is capped, and directly translated into a full-length non-structural polyprotein (nsP) called P1234, which is encoded by the 5' two-thirds of the genome (Jose, J., J. E. Snyder, and R. J. Kuhn, A structural and functional perspective of alphavirus replication and assembly. Future Microbiol, 2009. 4(7): p. 837-56; Kuhn, R. J., Togaviridae: the viruses and their replication, in Fields Virology, 5th ed., D. M. Knipe, Editor 2007, Wolters Kluwer, Lippincott Williams & Wilkins. p. 1001-1022). This precursor cleaves itself to produce P123 and nsP4 that carries the RNA-dependent RNA polymerase activity. These proteins, together with cellular co-factors, assemble into a replication complex that produces antisense genomic RNA molecules. Subsequent cleavage of P123 into nsP1 and P23 gives rise to a polymerase complex making both sense and antisense genomic RNA. Further processing of P23 into nsP2 and nsP3 gives rise to a polymerase complex making only positive-sense genomic RNA molecules. In addition to replicating the viral genome, this viral protein complex transcribes a 26S subgenomic RNA from the 3' extremity of the viral genome. This messenger RNA is translated into a polyprotein precursor, which is cleaved by a combination of viral and cellular enzymes to produce a capsid protein (C), two major envelope proteins (E1 and E2), and two smaller accessory peptides, E3 and 6k. Once assembled, CHIKV virions are spherical particles of 65-70 nm in diameter, essentially composed of genomic RNA molecules associated with capsid proteins, and enveloped in a host-derived lipid membrane decorated by E1-E2 heterodimers organized in an icosahedral lattice (Voss, J. E., et al., Glycoprotein organization of Chikungunya virus particles revealed by X-ray crystallography. Nature, 2010. 468(7324): p. 709-12).

The disease severity, as much as the evolution and spread of the virus into new geographic areas are a serious health public matter that needs to be fixed. In order to solve this problem, vaccines with live attenuated virus, with chimeric alphavirus, with recombinant DNA or with virus-like particles have been developed.

A formalin inactivated vaccine was shown to be immunogenic in non-human primates and humans, but the high amount of antigen required for mass immunization that needs to be prepared under BSL-3 conditions is a limitation for the development of this strategy (Tiwari, M., et al., Assessment of immunogenic potential of Vero adapted formalin inactivated vaccine derived from novel ECSA genotype of Chikungunya virus. (Vaccine, 2009. 27(18): p. 2513-22). The live attenuated TSI-GSD-218 CHIKV vaccine developed by the US-Army was immunogenic but caused side effects in Phase II clinical trials associated with reversion to virulence raising safety issues. Therefore, although the results obtained with vaccines based on live attenuated virus show that an efficient immunization can be achieved by this way, those vaccines are still questionable as there could be a risk of possibly side effects (Edelman R et al., Am J Trop Med Hyg. 2000 June; 62(6):681-685). Chimeric alphavirus vaccine strategies encoding the E1, E2 and capsid proteins from CHIKV are immunogenic in mice (Wang, E., et al., Chimeric alphavirus vaccine candidates for Chikungunya. Vaccine, 2008. 26(39): p. 5030-9), but the ability of alphavirus to easily recombine raises safety issues against the development of such strategies (Weaver, S. C., et al., Recombinational history and molecular evolution of western equine encephalomyelitis complex alphaviruses. J Virol, 1997. 71(1): p. 613-23).

Another strategy, which has been explored is to design recombinant DNA construct for use as a vaccine. DNA based CHIKV vaccines encoding the E1, E2 and capsid protein have been shown to be immunogenic in mice and non-human primates (Muthumani, K., et al., Immunogenicity of novel consensus-based DNA vaccines against Chikungunya virus. Vaccine, 2008. 26(40): p. 5128-34; Mallilankaraman, K., et al., A DNA vaccine against chikungunya virus is protective in mice and induces neutralizing antibodies in mice and nonhuman primates. PLoS Negl Trop Dis, 2011. 5(1): p. e928), but the DNA strategies do not induce the strong neutralizing immune response required for CHIKV clearance in humans. The disadvantages of DNA vaccines are that high quantities of DNA are required to induce an immune response and multiple booster vaccinations must be performed. The need for multiple boosts and high quantities of DNA injected into the nuclei of many cells raises concern regarding the fact that DNA vaccines can integrate into the host DNA and cause insertional mutagenesis. Therefore a recent study reports using DNA vaccines combined with live attenuated virus (WO2011/082388). Although this technique allows reducing drawbacks of live attenuated virus and DNA vaccines, there is still a need in providing a vaccine with reduced side effects.

In order to avoid drawbacks of live attenuated virus and DNA vaccines, other types of vaccines have been developed such as vaccines based on virus-like particles (VLPs) which are obtained by expressing structural proteins of the Chikungunya virus. These structural proteins are able to self-assemble in virus-like particles. On that basis, vaccines comprising polynucleotides encoding all Chikungunya virus structural proteins have been worked out (Akahata, W., et al., A virus-like particle vaccine for epidemic Chikungunya virus protects nonhuman primates against infection. Nat Med, 2010. 16(3): p. 334-8). However, VLPs produced in vitro are expensive to manufacture and require three administrations for a complete immunity, therefore these vaccines are not cheaply affordable. The CHIKV VLPs strategy disclosed in Akata et al. required several immunizations with an adjuvant to induce protection. For this reason, there is still a need for the design of improved vaccines that would enable the CHIKV VLPs to be generated in vivo in infected cells, in particular in infected cells of a host, and thus to provide an efficient and long-lasting immunity, especially which induces life-long immunity after only a single or two administration steps.

DESCRIPTION OF THE INVENTION

To this end, the inventors achieved the production of vaccines based on recombinant infectious replicative measles virus recombined with polynucleotides encoding Chikungunya virus antigens, which are recovered when the recombinant virus replicates in particular in the host after administration. The invention thus relates to a live CHIKV vaccine active ingredient based on the widely used Schwarz measles pediatric vaccine. In a preferred embodiment, this recombinant live MV-CHIKV vaccine yields CHIK virus-like particles by replicating in infected cells.

Measles virus is a non-segmented single-stranded, negative-sense enveloped RNA virus of the genus *Morbilivirus* within the family of Paramyxoviridae. This virus has been isolated in 1954 (Enders, J. F., and T. C. Peebles. 1954. Propagation in tissue cultures of cytopathogenic agents from patients with measles. Proc. Soc. Exp. Biol. Med. 86:277-286.), and live attenuated vaccines have been derived from this virus since then to provide vaccine strains and in particular from the Schwarz strain. Measles vaccines have been administered to hundreds of millions of children over the last 30 years and have proved its efficiency and safety. It is produced on a large scale in many countries and is distributed at low cost. For all these reasons, the inventors used attenuated Measles viruses to generate recombinant Measles virus particles stably expressing structural antigens of Chikungunya virus, in particular as VLPs.

The invention thus relates to a nucleic acid construct which comprises a polynucleotide encoding at least one Chikungunya virus (CHIKV) structural protein said polynucleotide being operably linked, in particular cloned into a cDNA molecule which encodes the nucleotide sequence of the full-length, infectious antigenomic (+) RNA strand of a measles virus (MV).

A nucleic acid construct according to the invention is in particular a purified DNA molecule, obtained or obtainable by recombination of various polynucleotides of different origins, operably linked together.

The expression "operably linked" refers to the functional link existing between the different polynucleotides of the nucleic acid construct of the invention such that said different polynucleotides and nucleic acid construct are efficiently transcribed and if appropriate translated, in particular in cells or cell lines, especially in cells or cell lines used as part of a rescue system for the production of chimeric infectious MV particles of the invention or in host cells.

In a particular embodiment of the invention, the construct is prepared by cloning a polynucleotide encoding one structural protein or a plurality of structural proteins of CHIKV in the cDNA encoding the full-length antigenomic (+) RNA of the measles virus. Alternatively, a nucleic acid construct of the invention may be prepared using steps of synthesis of nucleic acid fragments or polymerization from a template, including by PCR.

In a particular embodiment of the invention, the polynucleotide encoding the at least one protein of the CHIKV, or each of these polynucleotides, is cloned into an ATU (Additional Transcription Unit) inserted in the cDNA of the measles virus. ATU sequences are known from the skilled person and comprise, for use in steps of cloning into cDNA of MV, cis-acting sequences necessary for MV-dependant expression of a transgene, such as a promoter of the gene preceding, in MV cDNA, the insert represented by the polynucleotide encoding the CHIKV protein(s) inserted into a multiple cloning sites cassette.

When used to carry out the invention, the ATU is advantageously located in the N-terminal sequence of the cDNA molecule encoding the full-length (+)RNA strand of the antigenome of the MV and is especially located between the P and M genes of this virus or between the H and L genes. It has been observed that the transcription of the viral RNA of MV follows a gradient from the 5' to the 3' end. This explains that, when inserted in the 5' end of the coding sequence of the cDNA, the ATU will enable a more efficient expression of the heterologous DNA sequence (e.g. the polynucleotide encoding the at least one structural protein of the CHIKV) that it contains.

The polynucleotide encoding at least one structural protein of CHIKV may thus be inserted in any intergenic region of the cDNA molecule of the measles virus in particular in an ATU. Particular constructs of the invention are those illustrated in the examples.

In a particular embodiment, when several distinct polynucleotides are present in the DNA construct, each of these polynucleotides encoding at least one structural protein of the CHIKV may be inserted in different sites of MV cDNA, possibly in distinct ATU of the cDNA of the measles virus.

In a preferred embodiment of the invention, the polynucleotide encoding at least one of the structural proteins of CHIKV is inserted in the intergenic region of the P and M genes of the measles virus cDNA molecule, in particular in an ATU.

The expression "encoding" used in the present application defines the ability of the nucleic acid molecules to be transcribed and where appropriate translated for product expression into selected cells or cell lines. Accordingly, the nucleic acid construct of the invention may comprise regulatory elements controlling the transcription of the coding sequences, in particular promoters and termination sequences for the transcription and possibly enhancer and other cis-acting elements. These regulatory elements may be heterologous with respect to the CHIKV polynucleotide sequences.

The term "protein" is used interchangeably with the terms "antigen" or "polypeptide" and defines a molecule resulting from a concatenation of amino acid residues. In particular, the proteins disclosed in the application originate from the CHIKV and are structural proteins that may be identical to native proteins or alternatively that may be derived thereof by mutation, including by substitution (in particular by conservative amino acid residues) or by addition of amino acid residues or by secondary modification after translation or by deletion of portions of the native proteins(s) resulting in fragments having a shortened size with respect to the native protein of reference. Fragments are encompassed within the present invention to the extent that they bear epitopes of the native protein suitable for the elicitation of an immune response in a host in particular in a human host, preferably a response that enables the protection against CHIKV infection or against CHIKV associated disease. Epitopes are in particular of the type of B epitopes involved in the elicitation of a humoral immune response through the activation of the production of antibodies in a host to whom the protein has been administered or in whom it is expressed following administration of the infectious replicative particles of the invention. Epitopes may alternatively be of the type of T epitopes involved in elicitation of Cell Mediated Immune response (CMI response). Fragments may have a size representing more than 50% of the amino-acid sequence size of the native protein of CHIKV, preferably at least 90% or 95%. Alternatively, fragments may be short polypeptides with at least 10 amino acid residues, which harbor epitope(s) of the native protein. Fragments in this respect also include polyepitopes as defined herein.

In a particular embodiment of the invention, the cDNA encoding the nucleotide sequence of the full-length, infectious antigenomic (+) RNA strand of MV in nucleic acid construct complies with the rule of six (6) of the measles virus genome.

The organization of the genome of measles viruses and their replication and transcription process have been fully identified in the prior art and are especially disclosed in Horikami S. M. and Moyer S. A. (Curr. Top. Microbiol. Immunol. (1995) 191, 35-50 or in Combredet C. et al (Journal of Virology, November 2003, p 11546-11554) for the Schwarz vaccination strain of the virus or for broadly considered negative-sense RNA viruses, in Neumann G. et al (Journal of General Virology (2002) 83, 2635-2662).

The "rule of six" is expressed in the fact that the total number of nucleotides present in a nucleic acid representing the MV(+) strand RNA genome or in nucleic acid constructs comprising same is a multiple of six. The "rule of six" has been acknowledged in the state of the art as a requirement regarding the total number of nucleotides in the genome of the measles virus, which enables efficient or optimized replication of the MV genomic RNA. In the embodiments of the present invention defining a nucleic acid construct that meets the rule of six, said rule applies to the nucleic acid construct specifying the cDNA encoding the full-length MV (+) strand RNA genome. In this regard the rule of six applies individually to the cDNA encoding the nucleotide sequence of the full-length infectious antigenomic (+) RNA strand of the measles virus possibly but not necessarily to the polynucleotide cloned into said cDNA and encoding one or more protein(s) of the CHIKV.

According to a particular aspect of the invention, the nucleic acid construct comprises the following gene transcription units encompassing from 5' to 3':

(a) a polynucleotide encoding the N protein of a MV,
(b) a polynucleotide encoding the P protein of a MV,
(c) the polynucleotide encoding at least one CHIKV structural protein,
(d) a polynucleotide encoding the M protein of a MV,
(e) a polynucleotide encoding the F protein of a MV,
(f) a polynucleotide encoding the H protein of a MV, and
(g) a polynucleotide encoding the L protein of a MV, said polynucleotides and nucleic acid construct being operably linked and under the control of viral replication and transcription regulatory sequences such as MV leader and trailer sequences.

The expressions "N protein", "P protein", "M protein", "F protein", "H protein" and "L protein" refer respectively to the nucleoprotein (N), the phosphoprotein (P), the matrix protein (M), the fusion protein (F), the hemagglutinin protein (H) and the RNA polymerase large protein (L) of a Measles virus. These components have been identified in the prior art and are especially disclosed in Fields, Virology (Knipe & Howley, 2001).

In a preferred embodiment of the invention, the cDNA molecule encoding the full-length, infectious antigenomic (+)RNA strand of a measles virus is characteristic of or is obtained from an attenuated strain of MV.

An "attenuated strain" of measles virus is defined as a strain that is avirulent or less virulent than the parent strain in the same host, while maintaining immunogenicity and possibly adjuvanticity when administered in a host i.e., preserving immunodominant T and B cell epitopes and possibly the adjuvanticity such as the induction of T cell costimulatory proteins or the cytokine IL-12.

An attenuated strain of a Measles virus accordingly refers to a strain which has been serially passaged on selected cells and, possibly, adapted to other cells to produce seed strains suitable for the preparation of vaccine strains, harboring a stable genome which would not allow reversion to pathogenicity nor integration in host chromosomes. As a particular "attenuated strain", an approved strain for a vaccine is an attenuated strain suitable for the invention when it meets the criteria defined by the FDA (US Food and Drug Administration) i.e., it meets safety, efficacy, quality and reproducibility criteria, after rigorous reviews of laboratory and clinical data.

Particular strains that can be used to implement the present invention and especially to derive the MV cDNA of the nucleic acid construct are the Schwarz MV strain, the Zagreb strain, the AIK-C strain and the Moraten strain. All these strains have been described in the prior art and access to them is provided in particular as commercial vaccines.

According to a particular embodiment of the invention, the cDNA molecule is placed under the control of heterologous expression control sequences.

The insertion of such a control for the expression of the cDNA, is favorable when the expression of this cDNA is sought in cell types which do not enable full transcription of the cDNA with its native control sequences.

According to a particular embodiment of the invention, the heterologous expression control sequence comprises the T7 promoter and T7 terminator sequences. These sequences are respectively located 5' and 3' of the coding sequence for the full length antigenomic (+)RNA strand of MV and from the adjacent sequences around this coding sequence.

In a particular embodiment of the invention, the cDNA molecule, which is defined hereabove is modified i.e., comprises additional nucleotide sequences or motifs.

In a preferred embodiment, the cDNA molecule of the invention further comprises, at its 5'-end, adjacent to the first nucleotide of the nucleotide sequence encoding the full-length antigenomic (+)RNA strand of the MV approved vaccine strain, a GGG motif followed by a hammerhead ribozyme sequence and which comprises, at its 3'-end, adjacent to the last nucleotide of said nucleotide sequence encoding the full length anti-genomic (+)RNA strand, the sequence of a ribozyme. The Hepatitis delta virus ribozyme (δ) is appropriate to carry out the invention.

The GGG motif placed at the 5' end, adjacent to the first nucleotide of the above coding sequence improves the efficiency of the transcription of said cDNA coding sequence. As a requirement for the proper assembly of measles virus particles is the fact that the cDNA encoding the antigenomic (+)RNA complies with the rule of six, when the GGG motif is added, a ribozyme is also added at the 5' end of the coding sequence of the cDNA, 3' from the GGG motif, in order to enable cleavage of the transcript at the first coding nucleotide of the full-length antigenomic (+)RNA strand of MV.

In a particular embodiment of the invention, in order to prepare the nucleic acid construct of the invention, the preparation of a cDNA molecule encoding the full-length antigenomic (+) RNA of a measles virus disclosed in the prior art is achieved by known methods. Said cDNA provides especially the genome vector when it is inserted in a vector such as a plasmid.

A particular cDNA molecule suitable for the preparation of the nucleic acid construct of the invention is the one obtained using the Schwarz strain of measles virus. Accordingly, the cDNA used within the present invention may be obtained as disclosed in WO2004/000876 or may be obtained from plasmid pTM-MVSchw deposited by Institut Pasteur at the CNCM under No I-2889 on Jun. 12, 2002, the sequence of which is disclosed in WO2004/000876 incorporated herein by reference. The plasmid pTM-MVSchw has been obtained from a Bluescript plasmid and comprises the polynucleotide coding for the full-length measles virus (+) RNA strand of the Schwarz strain placed under the control of the promoter of the T7 RNA polymerase. It has 18967 nucleotides and a sequence represented as SEQ ID NO: 1. cDNA molecules (also designated cDNA of the measles virus or MV cDNA for convenience) from other MV strains may be similarly obtained starting from the nucleic acid purified from viral particles of attenuated MV such as those described herein.

The nucleic acid construct of the invention is suitable and intended for the preparation of recombinant infectious replicative measles-Chikungunya virus (MV-CHIKV) and accordingly said nucleic acid construct is intended for insertion in a transfer genome vector that as a result comprises the cDNA molecule of the measles virus, especially of the Schwarz strain, for the production of said MV-CHIKV virus and yield of CHIKV structural protein(s), in particular CHIKV VLPs. The pTM-MVSchw plasmid is suitable to prepare the transfer vector, by insertion of the CHIKV polynucleotide(s) necessary for the expression of CHIKV structural protein(s), in particular CHIKV VLPs.

The invention thus relates to a transfer vector, which is used for the preparation of recombinant MV-CHIKV particles when rescued from helper cells. The transfer vector of the invention is advantageously a plasmid, in particular a plasmid obtained from a Bluescript plasmid.

The invention also concerns the use of the transfer vector to transform cells suitable for rescue of viral MV-CHIKV particles, in particular to transfect or to transduce such cells respectively with plasmids or with viral vectors harbouring the nucleic acid construct of the invention, said cells being selected for their capacity to express required measles virus proteins for appropriate replication, transcription and encapsidation of the recombinant genome of the virus corresponding to the nucleic acid construct of the invention in recombinant, infectious, replicative MV-CHIKV particles.

The invention also relates to the cells or cell lines thus transformed by the transfer vector of the invention and by further polynucleotides providing helper functions and proteins.

Polynucleotides are thus present in said cells, which encode proteins that include in particular the N, P and L proteins of a measles virus (i.e., native MV proteins or functional variants thereof capable of forming ribonucleoprotein (RNP) complexes), preferably as stably expressed proteins at least for the N and P proteins functional in the transcription and replication of the recombinant viral MV-CHIKV particles. The N and P proteins may be expressed in the cells from a plasmid comprising their coding sequences or may be expressed from a DNA molecule inserted in the genome of the cell. The L protein may be expressed from a different plasmid. It may be expressed transitory. The helper cell is also capable of expressing a RNA polymerase suitable to enable the synthesis of the recombinant RNA derived from the nucleic acid construct of the invention, possibly as a stably expressed RNA polymerase. The RNA polymerase may be the T7 phage polymerase or its nuclear form (nlsT7).

In an embodiment, the cDNA clone of a measles virus is from the same measles virus strain as the N protein and/or the P protein and/or the L protein. In another embodiment, the cDNA clone of a measles virus is from a different strain of virus than the N protein and/or the P protein and/or the L protein.

The invention thus relates to a process for the preparation of recombinant infectious measles virus particles comprising:
 1) transferring, in particular transfecting, the nucleic acid construct of the invention or the transfer vector containing such nucleic acid construct in a helper cell line which also expresses proteins necessary for transcription, replication and encapsidation of the antigenomic (+)RNA sequence of MV from its cDNA and under conditions enabling viral particles assembly and
 2) recovering the recombinant infectious MV-CHIKV virus expressing at least one structural protein of CHIKV.

According to a particular embodiment this process comprises:
 1) transfecting helper cells with a nucleic acid construct according to the invention with a transfer vector, wherein said helper cells are capable of expressing helper functions to express an RNA polymerase, and to express the N, P and L proteins of a MV virus;
 2) co-cultivating said transfected helper cells of step 1) with passaged cells suitable for the passage of the MV attenuated strain from which the cDNA originates;
 3) recovering the recombinant infectious MV-CHIKV virus expressing at least one structural protein of CHIKV.

According to another particular embodiment of the invention the method for the production of recombinant infectious MV-CHIKV virus comprises:

1) recombining a cell or a culture of cells stably producing a RNA polymerase, the nucleoprotein (N) of a measles virus and the polymerase cofactor phosphoprotein (P) of a measles virus, with a nucleic acid construct of the invention and with a vector comprising a nucleic acid encoding a RNA polymerase large protein (L) of a measles virus, and
2) recovering the infectious, MV-CHIKV virus from said recombinant cell or culture of recombinant cells.

According to a particular embodiment of said process, recombinant MV are produced, which express CHIKV structural protein, in particular CHIKV VLPs wherein the particles express a combination of antigens, e.g. CE3E26KE1 antigens of CHIK virus. As an illustration, a process to rescue recombinant MV expressing CHIKV structural proteins, in particular CHIKV VLPs comprises the steps of:

1) cotransfecting helper cells, in particular HEK293 helper cells, that stably express T7 RNA polymerase, and measles N and P proteins with (i) a transfer vector, in particular a plasmid, comprising cDNA encoding the full-length antigenomic (+)RNA of a measles virus recombined with at least one polynucleotide encoding CHIKV structural proteins, for example encoding the CHIKV-CE3E26KE1 antigens and with (ii) a vector, especially a plasmid, encoding the MV L polymerase cDNA;
2) cultivating said cotransfected helper cells in conditions enabling the production of MV-CHIKV recombinant virus;
3) propagating the thus produced recombinant virus by co-cultivating said helper cells of step 2) with cells enabling said propagation such as Vero cells;
4) recovering replicating MV-CHIKV recombinant virus and CHIKV structural proteins, in particular CHIKV Virus Like Particles, in particular CHIKV-CE3E26KE1 VLPs.

Such a process, together with the constructs and conditions used are illustrated in FIG. 1B.

As used herein, "recombining" means introducing at least one polynucleotide into a cell, for example under the form of a vector, said polynucleotide integrating (entirely or partially) or not integrating into the cell genome (such as defined above).

According to a particular embodiment, recombination can be obtained with a first polynucleotide, which is the nucleic acid construct of the invention. Recombination can, also or alternatively, encompasses introducing a polynucleotide, which is a vector encoding a RNA polymerase large protein (L) of a measles virus, whose definition, nature and stability of expression has been described herein.

In accordance with the invention, the cell or cell lines or a culture of cells stably producing a RNA polymerase, a nucleoprotein (N) of a measles virus and a polymerase cofactor phosphoprotein (P) of a measles virus is a cell or cell line as defined in the present specification or a culture of cells as defined in the present specification, i.e., are also recombinant cells to the extent that they have been modified by the introduction of one or more polynucleotides as defined above. In a particular embodiment of the invention, the cell or cell line or culture of cells, stably producing the RNA polymerase, the N and P proteins, does not produce the L protein of a measles virus or does not stably produce the L protein of a measles virus, e.g., enabling its transitory expression or production.

The production of MV-CHIKV virus of the invention may involve a transfer of cells transformed as described herein. "Transfer" as used herein refers to the plating of the recombinant cells onto a different type of cells, and particularly onto monolayers of a different type of cells. These latter cells are competent to sustain both the replication and the production of infectious MV-CHIKV virus i.e., respectively the formation of infectious viruses inside the cell and possibly the release of these infectious viruses outside of the cells. This transfer results in the co-culture of the recombinant cells of the invention with competent cells as defined in the previous sentence. The above transfer may be an additional, i.e., optional, step when the recombinant cells are not efficient virus-producing culture i.e., when infectious MV-CHIKV virus cannot be efficiently recovered from these recombinant cells. This step is introduced after further recombination of the recombinant cells of the invention with nucleic acid construct of the invention, and optionally a vector comprising a nucleic acid encoding a RNA polymerase large protein (L) of a measles virus.

In a particular embodiment of the invention, a transfer step is required since the recombinant cells, usually chosen for their capacity to be easily recombined are not efficient enough in the sustaining and production of recombinant infectious MV-CHIKV virus. In said embodiment, the cell or cell line or culture of cells of step 1) of the above-defined methods is a recombinant cell or cell line or culture of recombinant cells according to the invention.

Cells suitable for the preparation of the recombinant cells of the invention are prokaryotic or eukaryotic cells, particularly animal or plant cells, and more particularly mammalian cells such as human cells or non-human mammalian cells or avian cells or yeast cells. In a particular embodiment, cells, before recombination of its genome, are isolated from either a primary culture or a cell line. Cells of the invention may be dividing or non-dividing cells.

According to a preferred embodiment, helper cells are derived from human embryonic kidney cell line 293, which cell line 293 is deposited with the ATCC under No. CRL-1573. Particular cell line 293 is the cell line disclosed in WO2008/078198 and referred to in the following examples.

According to another aspect of this process, the cells suitable for passage are CEF cells. CEF cells can be prepared from fertilized chicken eggs as obtained from EARL Morizeau, 8 rue Moulin, 28190 Dangers, France, or from any other producer of fertilized chicken eggs.

The process which is disclosed according to the present invention is used advantageously for the production of infectious replicative MV-CHIKV virus appropriate for use as immunization compositions.

The invention thus relates to an immunogenic composition whose active principle comprises infection replicative MV-CHIKV virus rescued from the nucleic acid construct of the invention and in particular obtained by the process disclosed.

As defined herein the nucleic acid construct of the invention and the MV-CHIKV virus of the invention encode or express at least one CHIKV structural protein.

By "Chikungunya virus structural protein" is meant a "protein" as defined herein the sequence of which is identical to a counterpart in a strain of CHIKV, including a polypeptide which is a native mature or precursor of a structural protein of CHIKV or is a fragment thereof or a mutant thereof as defined herein in particular a fragment or a mutant having at least 50%, at least 80%, in particular advantageously at least 90% or preferably at least 95% amino acid sequence identity to a naturally occurring Chikungunya virus capsid or envelope protein. Amino acid sequence identity can be determined by alignment by one of skill in the art using manual alignments or using the numerous alignment programs available (for example, BLASTP—http://blast.ncbi.nlm.nih.gov/). Fragments or mutants of CHIKV structural proteins of the invention may be defined with respect to the particular amino acid sequences illustrated herein.

According to the invention, the polynucleotide encoding at least one of the structural proteins of CHIKV encodes one or a plurality of proteins selected in the group of structural glycoproteins, structural polypeptides and capsid protein.

In a particular embodiment, the glycoproteins encompass the envelope glycoproteins E1, E2 and E3 envelope glycoproteins. The polypeptides encompass the 6K polypeptide and the capsid protein. In the following paragraphs the terms protein or glycoprotein will be used interchangeably to designate the E1, E2, or E3 glycoproteins or their combinations.

According to a particular embodiment of the invention, the polynucleotide encoding the CHIKV structural proteins is selected in the group of:
- A polynucleotide encoding one of the E1, E2, E3, 6K or C proteins;
- A fusion polynucleotide encoding several proteins selected among the E1, E2, E3, 6K and C proteins;
- A polynucleotide encoding the E3-E2-6K-E1 polyprotein;
- A polynucleotide which encodes the C-E3-E2-6K-E1 polyprotein and in particular the open reading frame (ORF) derived from a CHIKV genome or a corresponding cDNA which encodes said polyprotein;
- Any of these polynucleotides which has been modified in order to encode a mutated form of one or more of these proteins, in particular a mutated form of the E2 protein.

A particular polynucleotide in this respect encodes a soluble form of the E2 protein (sE2) or encodes the ectodomain of the E2 protein or its soluble form (sE2Δstem). In a particular embodiment, the polynucleotide encodes one of the following polypeptides: E3-sE2-6K-E1, E3-sE2Δstem-6K-E1, C-E3-sE2-6K-E1, and C-E3-sE2Δstem-6K-E1.

As used herein, the term "ectodomain" means the domain of glycoprotein E2 which extends outside the viral particle and is responsible for attachment to and entry into cells during infection by CHIKV viral particles.

According to a particular embodiment, the polynucleotide encodes a single epitope of a CHIKV structural protein or encodes a polyepitope resulting from expression of repeated epitopes (having identical or similar sequences) or multiple distinct epitopes of one or many CHIKV structural proteins.

By way of illustration a polyepitope is formed by fusion of repeated polynucleotides encoding the E2 EP3 single epitope located at N-terminus of the E2 glycoprotein proximal to a furin E2/E3-cleavage site. The amino acid sequence of the E2 EP3 epitope is disclosed in Kam Y. W et al. (EMBO Mol Med 4, 330-343) and as SEQ ID NO: 33.

According to a particular embodiment of the invention, several polynucleotides wherein each polynucleotide encodes at least one structural protein of CHIKV are combined or fused to form a polynucleotide encoding several structural proteins of the CHIKV. These polynucleotides may distinguish from each other by the fact that they code for proteins of various strains of the CHIKV. As a result, the polynucleotide encodes a polyepitope as described herein, such as a polyepitope of single E2 EP3 epitope.

The polynucleotide(s) encoding at least one structural protein(s) of CHIKV is (are) cloned in the cDNA molecule encoding the full-length infectious antigenomic (+)RNA strand of a measles virus, to give rise to the nucleic acid construct of the invention, possibly into different sites.

According to one aspect of the invention, a polynucleotide encoding at least one Chikungunya virus (CHIKV) structural protein is derived from the genome of isolated and purified wild strain(s) of CHIKV. Wild strains of CHIKV can be for example the Ross strain (GenBank: AF490259.3), or the S27 strain (GenBank: AF339485.1), both isolated from patients during the 1952 Tanzania outbreak or, a strain isolated during the Senegal 1983 outbreak and named Ae. furcifer (GenBank: AY726732.1).

According to another aspect of the present invention, a polynucleotide encoding at least one CHIKV structural protein derives from the following purified and isolated wild strains of CHIKV: 05.61, 05.115, 05.209, 06.21, 06.27 and 06.49, which have been described in WO2007/105111. The nearly complete genome sequences of these CHIKV isolates representing distinct geographic origins, time points and clinical forms of the Indian Ocean outbreak of Chikungunya virus have been sequenced and disclosed in WO2007/105111. 11,601 nucleotides were determined, corresponding to positions 52 (5'NTR) to 11,667 (3'NTR, end of third Repeat Sequence Element) in the nucleotide sequence of the 1952 Tanzanian isolate S27 taken as a reference (total length 11,826 nt).

The genome sequences of the isolates 05.61, 05.115, 05.209, 06.21, 06.27 and 06.49 presented in WO2007/105111 and from which the polynucleotides according to the present invention may be derived in a particular embodiment of the invention are organized as follows. Coding sequences consist of two large open reading frames (ORF) of 7,422 nt and 3,744 nt encoding the nonstructural polyprotein (2,474 amino-acids) and the structural polyprotein (1,248 amino-acids), respectively. The non structural polyprotein is the precursor of proteins nsP1 (535 aa), nsP2 (798 aa), nsP3 (530 aa) and nsP4 (611 aa), and the structural polyprotein is the precursor of proteins C (261 aa), p62 (487 aa, precursor to E3-64 aa- and E2-423 aa), 6K (61 aa), and E1 (439 aa). Cleavage sites characteristic of the alphavirus family in the non-structural and structural polyproteins are conserved. Glycosylation sites in E3, E2 and E1 are also conserved. The disclosure of the genome sequences is incorporated herewith by reference.

According to one embodiment, a polynucleotide encoding the CHIKV structural protein(s) is derived from the genome of the following group of wild strains of CHIKV designated: 06.115, 06.21, 06.27 and 06.49, previously described.

The term "derive" appearing in the definition of the polynucluotides merely specifies that the sequence of said polynucleotide may be identical to the corresponding sequence in a CHIKV strain or may vary to the extent that it encodes structural protein(s) of CHIKV that meet(s) the definition of the "protein" according to the present invention. Accordingly, the term does not restrict the production mode of the polynucleotide.

The polynucleotide(s) and nucleic acid construct of the invention may rather be prepared in accordance with any known method in the art and in particular may be cloned, obtained by polymerization especially using PCR methods or may be synthesized.

The nucleic acid constructs of the invention are further defined as including one of the following polynucleotides encoding at least one CHIKV structural proteins.

According to a particular embodiment, a polynucleotide which encodes one or several structural protein(s) of CHIKV encodes a soluble form of the glycoprotein E2. As an example such a polynucleotide comprises a coding domain which has the sequence of SEQ ID NO: 2, 4, 6, 8.

In a particular embodiment, a polynucleotide which encodes one or several structural protein(s) of CHIKV encodes the E2 ectodomain. As an example, such a polynucleotide comprises a coding domain which has the sequence of SEQ ID NO: 10, 12, 14.

In another embodiment of the invention, the polynucleotide encoding a soluble form of the glycoprotein E2 encodes one polypeptide having an amino acid sequence selected in the group of SEQ ID NO: 3, 5, 7, 9.

In another embodiment of the invention, the polynucleotide encoding the ectodomain of the glycoprotein E2 encodes one polypeptide having an amino-acid sequence selected in the group of SEQ ID NO: 11, 13, 15.

According to a particular embodiment of the invention, the polynucleotide encoding structural protein of CHIKV encompasses one of the above defined nucleotide sequences encoding the soluble form of the E2 glycoprotein or the ectodomain of said protein and comprises further, a polynucleotide encoding one of the E3, E1, 6K or C protein, or a polynucleotide encoding any combination thereof.

Accordingly particular polynucleotides of the invention encoding structural polyprotein E2-6K-E1 of France/2010 strains isolated in Fréjus are selected in the following group: polynucleotides comprising a coding domain which has the sequence of SEQ ID NO: 16 (GenBank: CCA61130.1) and 20 (GenBank: CCA61131.1).

Preferred polynucleotide of the invention encodes structural proteins C-E3-E2-6K-E1 from a strain of CHIKV. In a particular embodiment, the polynucleotide encodes polyprotein C-E3-E2-6K-E1 of one of the strains named S27 or 06.49 and have respectively the sequences of SEQ ID NO: 20 and 27.

In another embodiment of the invention, the polynucleotide which is used encodes the E2 EP3 epitope or a polyepitope formed with a repetition of this epitope or comprising such repetition. This polynucleotide has in particular the nucleotide sequence disclosed as SEQ ID NO: 32.

According to a preferred embodiment, the invention also concerns modifications and optimization of the polynucleotide to allow an efficient expression of the Chikungunya virus proteins at the surface of chimeric infectious particles of MV-CHIKV in the host.

According to this embodiment, optimization of the polynucleotide sequence can be operated avoiding cis-active domains of nucleic acid molecules: internal TATA-boxes, chi-sites and ribosomal entry sites; AT-rich or GC-rich sequence stretches; ARE, INS, CRS sequence elements; repeat sequences and RNA secondary structures; cryptic splice donor and acceptor sites, branch points.

The optimized polynucleotides may also be codon optimized for expression in a specific cell type, in particular may be modified for the Maccaca codon usage or for the human codon usage. This optimization allows increasing the efficiency of chimeric infectious particles production in cells without impacting the expressed protein(s).

In particular, the optimization of the polynucleotide encoding the CHIKV protein(s) may be performed by modification of the wobble position in codons without impacting the identity of the amino acid residue translated from said codon with respect to the original one.

Optimization is also performed to avoid editing-like sequences from Measles virus. The editing of transcript of Measles virus is a process which occurs in particular in the transcript encoded by the P gene of Measles virus. This editing, by the insertion of extra G residues at a specific site within the P transcript, gives rise to a new protein truncated compared to the P protein. Addition of only a single G residue results in the expression of the V protein, which contains a unique carboxyl terminus (Cattaneo R et al., Cell. 1989 Mar. 10; 56(5):759-64).

In the polynucleotides according to this particular embodiment of the invention, the following editing-like sequences from Measles virus can be mutated: AAAGGG, AAAAGG, GGGAAA, GGGGAA, as well as their complementary sequence: TTCCCC, TTTCCC, CCTTTT, CCCCTT. For example, AAAGGG can be mutated in AAAGGC, AAAAGG can be mutated in AGAAGG or in TAAAGG or in GAAAGG, and GGGAAA in GCGAAA.

An embodiment of a modified and optimized polynucleotide according to the present invention is as defined in SEQ ID NO:29. This polynucleotide encodes the soluble form of the envelope protein E2 without the stem region.

An embodiment of a modified and optimized polynucleotide encoding all the structural proteins C-E3-E2-6K-E1 is as defined in SEQ ID NO: 31.

These optimized polynucleotides according to this particular embodiment of the invention as defined in SEQ ID NO: 29 and 31, present mutations in BsiWI and BssHII sites inside the sequences but not at the end of these sequences in order to maintain the sites for cloning purposes.

Therefore, according to this particular embodiment the invention provides nucleic acid constructs comprising polynucleotides which increase the efficiency of chimeric MV-CHIKV infectious particles production.

Other optimized polynucleotides comprising the sequences coding for structural proteins of the CHIKV and also suitable for use in the nucleic acid constructs of the invention are optimized fusion polynucleotides encoding one of the following combinations of structural proteins: E3-E2-6K-E1, E3-sE2-6K-E1, E3-sE2Δstem-6K-E1, C-E3-E2-6K-E1, C-E3-sE2-6K-E1, and C-E3-sE2Δstem-6K-E1.

The invention also relates to nucleic acid construct wherein the polynucleotide encoding at least one structural protein of CHIKV encodes one of the following polypeptides.

Examples of amino acid sequences of CHIK virus structural proteins according to preferred embodiments of the invention and related to a soluble form of the glycoprotein E2 from the following strains designated 05.115, 06.21, 06.27 and 06.49, are as defined in SEQ ID NO: 3, 5, 7, 9.

Examples of amino acid sequences of CHIK virus structural proteins according to preferred embodiments of the invention and related to the ectodomain of the glycoprotein E2 from the following strains designated 05.115, 06.21, 06.27 and 06.49, are as defined in SEQ ID NO: 11, 13, 15.

In a particular embodiment, the invention relates to fusion proteins constituted by the structural proteins E2-6K-E1 of a France/2010 strain isolated in Fréjus. These proteins result respectively from the expression of the polynucleotides which have the sequence of SEQ ID NO: 16 (GenBank: CCA61130.1) and 18 (GenBank: CCA61131.1). Their sequences are defined respectively in SEQ ID NO: 17 and 19.

In a particularly preferred embodiment, the invention concerns fusion proteins constituted by all CHIKV structural proteins. These proteins results from the expression of the polynucleotides encoding all the structural proteins C-E3-E2-6K-E1 and are defined in SEQ ID NO: 21, 22, 23, 24, 25, 26 and 28.

The structural proteins C-E3-E2-6K-E1 obtained are able to auto-assemble into CHIKV virus-like-particles (VLPs), in the CHIKV-MV particles.

As used herein, the term "virus-like particle" (VLP) refers to a structure that in at least one attribute resembles a virus but which has not been demonstrated to be infectious as such. Virus Like Particles in accordance with the invention do not carry genetic information encoding the proteins of the Virus Like Particles, in general, virus-like particles lack a viral genome and, therefore, are noninfectious and non replicative. In accordance with the present invention, Virus Like Particles can be produced in large quantities and are expressed together with CHIKV-MV recombinant particles.

In a particular embodiment, the invention relates to a soluble form of the glycoprotein E2 without the stem region from the strain of CHIKV designated 06.49. This glycoprotein results from the expression of the modified and optimized polynucleotide as defined in SEQ ID NO:29. Its sequence is defined in SEQ ID NO: 30.

According to another aspect, the invention relates to recombinant CHIKV-Measles virus particles expressing the Chikungunya virus structural protein(s) as defined herein, in particular by reference to their nucleic acid and polypeptide sequences. The recombinant CHIKV-MV virus advantageously expresses the CHIKV structural proteins as VLPs.

The invention also concerns the association, in a composition, of virus-like particles of CHIKV structural proteins, in particular VLPs of C-E3-E2-6K-E1, with CHIKV-MV infectious replicative virus particles.

According to a preferred embodiment of the invention, the recombinant measles virus vector is designed in such a way and the production process involves cells such that the virus particles produced in helper cells transfected or transformed with said vector, originated from a measles virus strain adapted for vaccination, enable the production of recombinant Measles-Chikungunya infectious and replicative virus and the production of CHIKV-VLPs for use in immunogenic compositions, preferably protective or even vaccine compositions.

Advantageously, the genome of the recombinant Measles-Chikungunya infectious virus of the invention is replication competent. By "replication competent", it is meant a nucleic acid, which when transduced into a helper cell line expressing the N, P and L proteins of a MV, is able to be transcribed and expressed in order to produce new viral particles.

Replication of the recombinant virus of the invention obtained using MV cDNA for the preparation of the recombinant genome of MV-CHIKV can also be achieved in vivo in the host, in particular the human host to which recombinant MV-CHIKV is administered.

The invention also concerns a composition or an assembly of active ingredients which comprises the recombinant Measles-Chikungunya replicative virus in association with VLPs of CHIKV structural proteins, such as VLPs of CE3E26KE1 proteins. These compositions or assemblies induce an immune response, in particular a protective immune response, against Chikungunya virus, and in particular elicit antibodies production directed against Chikungunya virus structural proteins and/or elicit a cellular immune response against CHIKV infection. These compositions accordingly may comprise a suitable vehicle for administration e.g. a pharmaceutically acceptable vehicle to a host, especially a human host and may further comprise but not necessarily adjuvant to enhance immune response in a host. The inventors have indeed shown that the administration of the active ingredients of the invention may elicit an immune response without the need for adjuvantation.

The invention relates in particular to a composition for administration to children.

The invention is also directed to an immunogenic composition, in particular a vaccine composition and in particular to a vaccine composition for administration to children. Said composition or vaccine is used for protection against CHIKV infection in a prophylactic treatment. Such a vaccine composition has advantageously active principles (active ingredients) which comprise recombinant Measles-Chikungunya infectious replicative viral particles rescued from the vector which has been defined herein associated with VLPs of CHIKV structural proteins, such as VLPs of CE3E26KE1 proteins.

In the context of the invention, the terms "associated" or "in association" refer to the presence, in a unique composition, of both MV-CHIKV recombinant viral particles and CHIKV structural proteins, in particular as VLPs, usually as physically separate entities.

The invention also concerns the recombinant MV-CHIKV infectious replicating virus particles in association with CHIKV-Virus structural proteins, in particular CHIKV-Virus Like Particles expressing CHIKV structural proteins, in particular CHIKV-CE3E26KE1 VLPs or the composition according to the invention, for use in the treatment or the prevention of an infection by Chikungunya virus in a subject, in particular in a human.

The invention also concerns MV-CHIKV infectious, replicative virus and associated CHIKV-Virus structural proteins, in particular associated VLPs of CHIKV structural proteins, such as VLPs of CE3E26KE1 proteins for use in an administration scheme and according to a dosage regime that elicit an immune response, advantageously a protective immune response, against CHIKV virus infection or induced disease, in particular in a human host.

The administration scheme and dosage regime may require a unique administration of a selected dose of MV-CHIKV infectious, replicative virus and associated CHIKV structural proteins, in particular associated VLPs of CHIKV structural proteins, such as VLPs of CE3E26KE1 proteins.

Alternatively it may require multiple doses administration in a prime-boost regimen. Priming and boosting may be achieved with identical active ingredients consisting of MV-CHIKV infectious, replicative virus and associated CHIKV structural proteins, in particular associated VLPs of CHIKV structural proteins, such as VLPs of CE3E26KE1 proteins.

Alternatively priming and boosting administration may be achieved with different active ingredients, involving MV-CHIKV infectious, replicative virus and associated CHIKV structural proteins, in particular associated VLPs of CHIKV structural proteins, such as VLPs of CE3E26KE1 proteins in at least one of the administration steps and other active immunogens of CHIKV, such as CHIKV proteins or VLPs expressing C-E3-E2-6K-E1 polyprotein, in other administration steps.

The invention also concerns an assembly of different active ingredients including as one of these ingredients MV-CHIKV infectious, replicative virus and associated CHIKV structural proteins, in particular associated VLPs of CHIKV structural proteins, such as VLPs of CE3E26KE1 proteins. The assembly of active ingredients is advantageously for use in immunization of a host, in particular a human host.

The inventors have shown that administration of MV-CHIKV infectious, replicative virus and associated VLPs of CHIKV structural proteins elicit an immune response and especially elicit antibodies that are cross-reactive for various CHIKV strains, at least in the ECSA genotype. Accordingly, it has been shown that administration of the active ingredients according to the invention, when prepared with the coding sequences of a particular strain of CHIKV, can elicit an immune response against a group of strains of CHIKV, in particular a group of strains of the ECSA genotype, in particular a group of strains encompassing CHIKV strain India, CHIKV strain Congo, CHIKV strain Thailand and CHIKV strain La Reunion.

Considering available knowledge on doses of vaccines suitable for other pathogens (such as HBV or HPV) which involve the administration of Virus Like Particles (VLP) and also for known human MV vaccines, the inventors have determined that the recovery of CHIKV-VLPs with the recombinant MV-CHIKV virus enables proposing administration of effective low doses of the active ingredients. Indeed, considering that the recombinant MV-CHIKV virus enables production of around $10^4$ CHIKV-VLPs per recombinant MV-CHIKV replicated particle, and considering that the currently known doses for human MV vaccines are in the range of $10^3$ to $10^4$ pfu, a suitable dose of recombinant MV-CHIKV virus to be administered may be in the range of 0.1 to 10 ng, in particular 0.2 to 6 ng, and possibly as low as 0.2 to 2 ng. For comparison doses of VLPs administered in the case of HBV or HPV vaccines are in the range of 10 μg which means that a dose of recombinant MV-CHIKV vaccine could comprise around 2 000 or up to 5 000 to 10 000 times less VLPs.

According to a particular embodiment of the invention, the immunogenic composition or the vaccine defined herein may also be used for protection against an infection by the measles virus.

DESCRIPTION OF THE DRAWINGS

FIG. 1 Schematic representation of ORFs for structural proteins of Chikungunya virus and for the backbone of MV genome-MV-CHIKV constructs including antigens of said CHIK virus for expression by Measles virus are proposed.

FIG. 1B. Rescue of recombinant MV expressing CHIKV VLP

FIG. 2 Immunofluorescence detection of E2 antigen in Vero cells infected by recombinant MV-CHIKV for 24 h at MOI 0.1 E2 was detected using the anti-E2 Mab 3E4 used at 1/100 dilution and secondary antibody were used at 1/5000 dilution.

FIG. 3: Expression of E2 and capsid proteins by MV-CHIKV vectors. Cell lysates (cells) and supernatants (SN) of Vero cells infected for 24 h by MV-sE2Δstem, and MV-CE3E26KE1 analyzed by western blot. E2 was probed with the 3E4 Mab, and C protein was detected using an anti-capsid Mab (from P. Després) used at 1/100 dilution and secondary antibodies were used at 1/5000 dilution.

FIG. 4. Electron microscopy analysis of CHIKV VLPs secreted in the supernatant of Vero cells infected by MV-CE3E26KE1 recombinant virus at MOI 0.1. Scale bar 200 nm (left) and 100 nm (right). Red arrows indicate the specific arrangement of spikes on particles surface and the icosahedral symmetry of the capsid protein inside the particles.

FIG. 5. Sequence of the truncated sE2 expressed by MV-sE2 recombinant virus (156 aa, 19 kDa).

FIG. 6: Growth kinetics of recombinant MV-sE2Δstem, and MV-CE3E26KE1 viruses compared with standard MV on Vero cells (MOI 0.01). Cell-associated virus titers are indicated in TCID50.

FIG. 7: Immunization and challenge schedule of example 2.

FIG. 8: Survival curve of mice lethally challenged with 100 PFU of CHIKV-06-49 after two immunizations with MV-CE3E26KE1 recombinant virus.

FIG. 9: Immunization and challenge schedule of example 3.

FIG. 10: Survival curve of mice lethally challenged with 100 PFU of CHIKV-06-49 after a single immunization with MV-CE3E26KE1 recombinant virus.

FIG. 13: Passive transfer of immune sera and challenge schedule of example 5.

FIG. 14: Survival curve of mice lethally challenged with 100 PFU of CHIKV-06-49 after passive transfer of MV-CE3E26KE1 immune sera.

FIG. 16: Immunization and challenge schedule of example 6.

FIG. 17: Survival curve of MV pre-immune mice lethally challenged with 100 PFU of CHIKV-06-49 after immunization with MV-CE3E26KE1.

EXAMPLES

Figure 11:
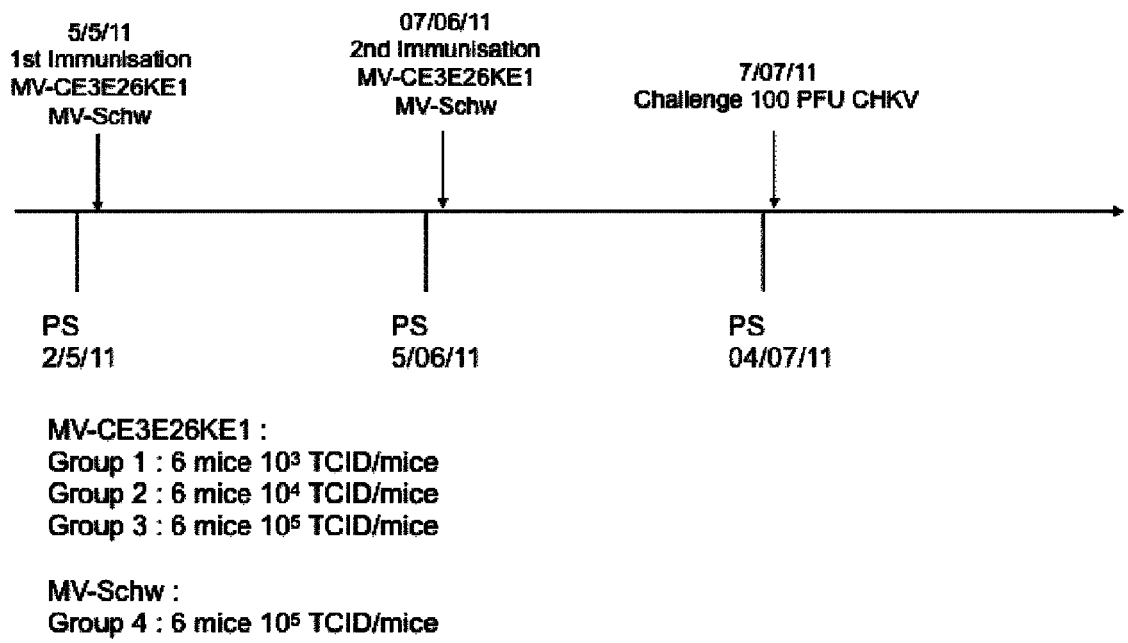
FIG. 11: Immunization and challenge schedule of example 4.

Construction and Characterization of Recombinant Measles Virus Vectors Expressing Chikungunya Virus Proteins.

The inventors designed three Chikungunya Virus antigens based on peptide sequences from native proteins of the strain 06-49 of Chikungunya virus. The native proteins enabling preparation of these peptide sequences were the five structural proteins which consist of capsid (C) envelope and accessory proteins E1, E2, E3 and 6K.

Figure 1A:
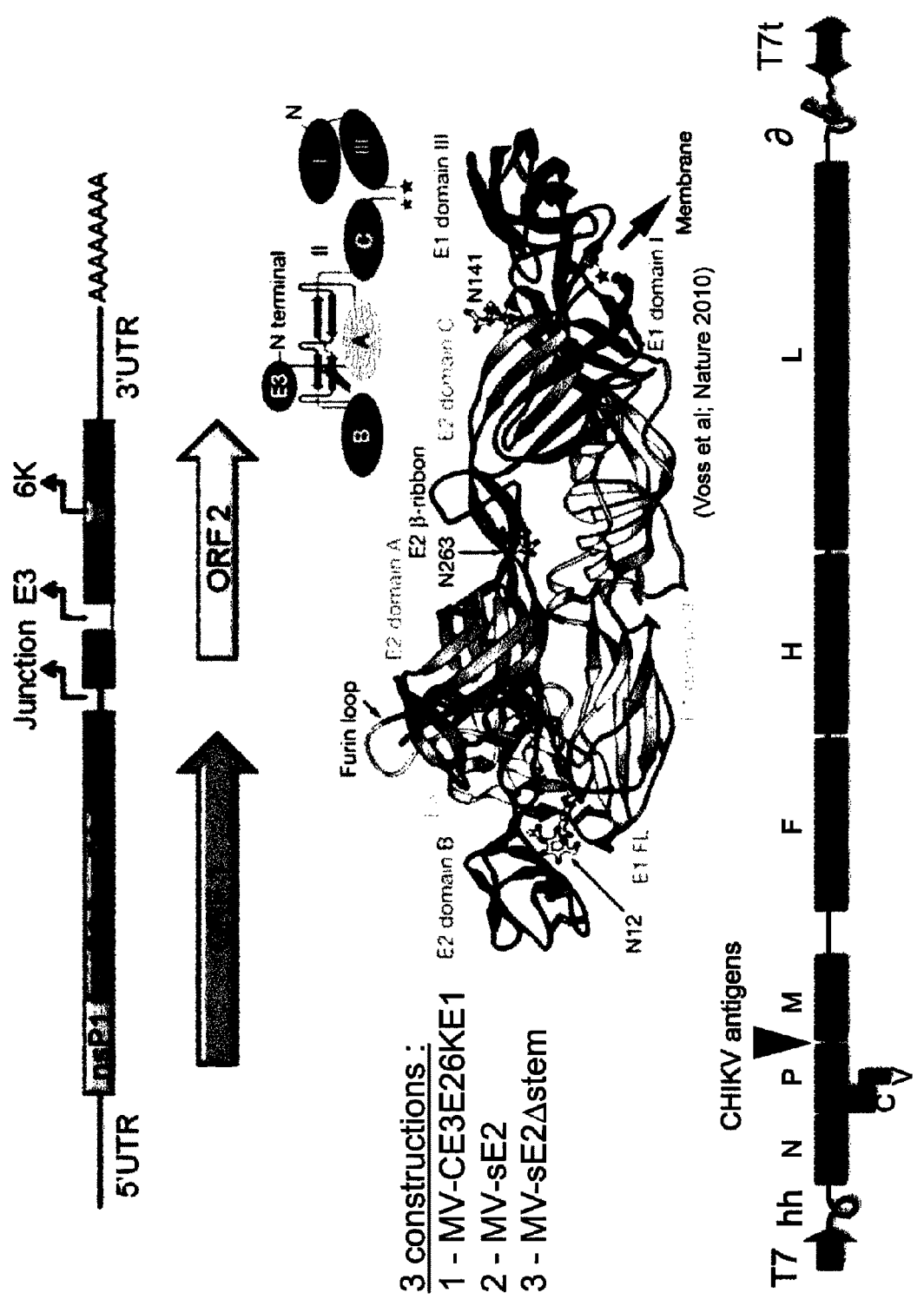
Figure 1B:
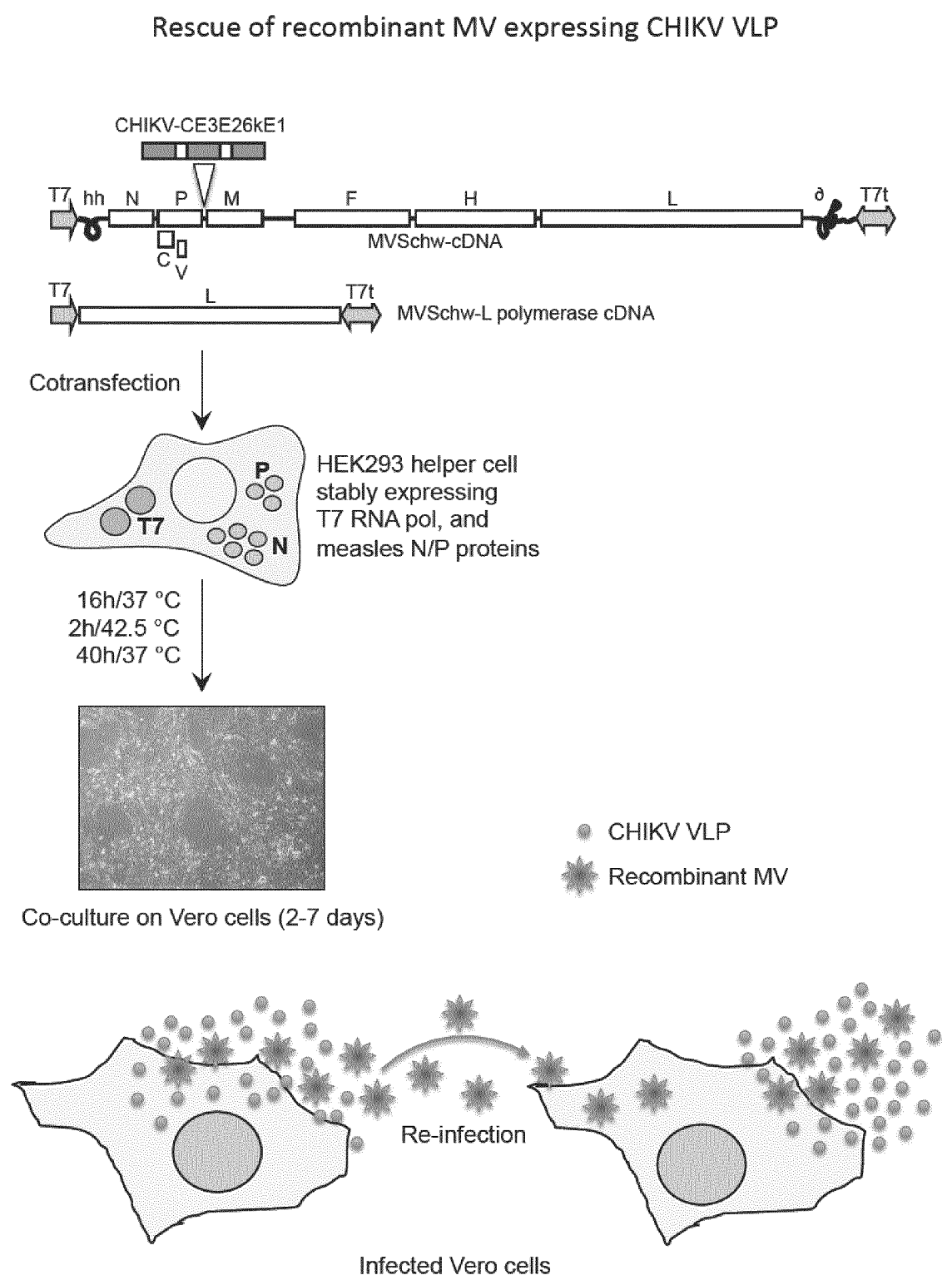

The first construct was directed to the expression of the soluble form of the envelope protein E2 (sE2), the second construct to the expression of the sE2 without the stem region (sE2Δstem), and the third construct was directed to the expression of all viral structural proteins (C-E3-E2-6K-E1) (FIG. 1). The experiment protocols have been described herein with respect to this latter construct.

Cell culture. Vero (African green monkey kidney) cells were maintained in DMEM GlutaMAX™ (Gibco-BRL) supplemented with 5% heat-inactivated fetal calf serum (FCS, Invitrogen, Frederick, Md.). HEK-293-T7-MV helper cells (WO2008/078198) used for recombinant measles virus rescue were grown in DMEM supplemented with 10% FCS.

Construction of pTM-MVSchw-CE3E26KE1. The plasmid pTM-MVSchw, which contains an infectious MV cDNA corresponding to the anti-genome of the Schwarz MV vaccine strain, has been described elsewhere (Combredet, C., et al., A molecularly cloned Schwarz strain of measles virus vaccine induces strong immune responses in macaques and transgenic mice. J Virol, 2003. 77(21): p. 11546-54). The cDNA encoding for the structural CE3E26KE1 CHIKV antigens was generated by chemical synthesis (GenScript, USA). It contains the sequence for viral structural proteins C-E3-E2-6K-E1 from CHIKV strain 06-49 (WO2007/105111). The complete sequence respects the "rule of six", which stipulates that the number of nucleotides into the MV genome must be a multiple of 6, and contains BsiWI restriction site at the 5' end, and BssHII at the 3' end. The sequence was optimized for measles virus expression in mammalian cells. This cDNA was inserted into BsiWI/BssHII-digested pTM-MVSchw-ATU2, which contains an additional transcription unit (ATU) between the phosphoprotein (P) and the matrix (M) genes of the Schwarz MV genome (Combredet, C., et al., A molecularly cloned Schwarz strain of measles virus vaccine induces strong immune responses in macaques and transgenic mice. J Virol, 2003. 77(21): p. 11546-54). The resulting plasmid was designated as pTM-MVSchw-CE3E26KE1.

Rescue of recombinant MV-CE3E26KE1. Rescue of recombinant Schwarz MV-CHIKV from the plasmid pTM-MVSchw-CE3E26KE1 was performed as previously described using a rescue system previously described (Radecke, F., et al., Rescue of measles viruses from cloned DNA. Embo J, 1995. 14(23): p. 5773-84; WO2008/078198). Viral titers were determined by endpoint limit dilution assay on Vero cells and TCID50 was calculated by using the Kärber method.

Immunofluorescence. Immunofluorescence staining was performed on infected cells, as described elsewhere (Lucas, M., et al., Infection of mouse neurons by West Nile virus is modulated by the interferon-inducible 2'-5' oligoadenylate synthetase 1b protein. Immun. Cell Biol., 2003. 81: p. 230-236). Cells were probed with mouse anti-E2 (3E4) and anti-capsid antibodies. Cy3-conjugated goat anti mouse IgG antibody Cy3 conjugated (Jackson Immunoresearch laboratories), was used as secondary antibody.

Western blot assays. Protein lysates from Vero cells infected with recombinant virus were fractionated by SDS-PAGE gel electrophoresis and transferred to cellulose membranes (Amersham Pharmacia Biotech). The blots were probed with mouse Mab 3E4 anti-E2 and anti-capsid. A goat anti-mouse immunoglobulin G (IgG)-horseradish peroxidase (HRP) conjugate (Amersham) was used as a secondary antibody. Peroxidase activity was visualized with an enhanced chemiluminescence detection kit (Pierce).

Analysis of VLP production by electron microscopy. Vero cells (3×T-150 flasks) were infected with MV-CHIKV recombinant virus at MOI 1. Supernatants collected after 36 h of infection were clarified by centrifugation at 3000 rpm for 30 min, layered on 20% sucrose cushion in PBS and centrifuged at 41,000 rpm for 2 h in a SW41 rotor. Pellets were resuspended in PBS with 1% BSA and analysed by electron microscopy. Negative staining was made by 2% uranyl acetate on copper grids coated with carbon and glow discharged just before use. The samples were observed at 80 kV with a Jeol JEM1200 (Tokyo, Japan) transmission electron microscope. Images were recorded using an Eloise Keenview camera and the Analysis Pro-software version 3.1 (Eloise SARL, Roissy, France).

Mice experiments. CD46-IFNAR mice susceptible to MV infection were produced as previously described (Combredet, C., et al., A molecularly cloned Schwarz strain of measles virus vaccine induces strong immune responses in macaques and transgenic mice. J Virol, 2003. 77(21): p. 11546-54). Mice were housed under specific pathogen-free conditions at the Pasteur Institute animal facility. For immunization, six-week-old CD46-IFNAR mice were inoculated intraperitoneally (i.p.) with $10^5$ TCID50 of recombinant MV-CE3E26KE1 or MV. For protection assays, immunized mice were i.p inoculated with 100 pfu of CHIKV 06-49 strain and mortality was followed for 2 weeks. All experiments were approved and conducted in accordance with the guidelines of the Office of Laboratory Animal Care at Pasteur Institute. For passive transfer study, CD46-IFNAR mice were inoculated intraperitoneally with 20 µl of pooled sera from 6 mice immunized with $10^5$ TCID50 of MV-CE3E26KE1. Control mice received either 20 µl of pooled sera from mice immunized with $10^5$ TCID50 of empty MVSchw or 20 µl of anti-CHIKV HMAF. The sera were diluted in a total volume of 100 µl in PBS before passive transfer at 24 h and 16 h before challenge with 100 pfu of CHIKV 06-49 strain, and then 12 h post-challenge to mimic antibody persistence in infected animals. Mice mortality was analyzed for 2 weeks to determine protection.

Analysis of humoral immune responses. To evaluate the specific antibody responses, mice were bled via the periorbital route at different time after immunization. Sera were heat inactivated at 56° C. for 30 min and anti-MV antibodies were detected by ELISA (ENZYGNOST-Siemens). HRP-conjugated anti-mouse immunoglobulin (Jackson Immuno Research) was used as secondary antibody. Anti-CHIKV antibodies were detected with a specific ELISA. Briefly, 96-wells plates were coated with a recombinant CHIKV-E2 protein produced in E. Coli. HRP-conjugated anti-mouse immunoglobulin was used as secondary antibody. The endpoint titers of pooled sera were calculated as the reciprocal of the last dilution giving twice the absorbance of sera from MV inoculated mice that served as negative controls. Anti-CHIKV neutralizing antibodies were measured by using a plaque reduction neutralization test (PRNT). Vero cells were seeded into 12-well plates for 24 h.

Serum samples were serially diluted in DMEM Glutamax/2% FCS. Dilutions of 100 µl were incubated for 2 h at 37° C., under gentle agitation, with an equal volume of CHIKV containing 100 pfu of 06-49 strain. Remaining infectivity was then assayed on Vero cell monolayers overlaid with DMEM GlutaMAX™/2% FCS containing 0.8% final (wt/vol) carboxy methylcellulose. After 3 days of incubation, cells were fixed and stained with crystal violet for plaque count determination. The endpoint neutralization titer was calculated as the highest serum dilution tested that reduced the number of plaques by at least 50% (PRNT50).

Analysis of cell mediated immune response. Six-week-old CD46+/−IFNα/βR−/− mice were inoculated intraperitoneally with $10^6$ TCID50 of MV-CHIKV recombinant virus. Control mice were immunized with $10^6$ TCID50 of empty MV vector. Mice were euthanized at 7 days post-infection and spleens were collected. Splenocytes from immunized mice were incubated in RPMI, 10% FCS, and 10 IU of recombinant human interleukin-2 (rh-IL-2; Boehringer Mannheim). Their capacity to secrete IFN-γ upon stimulation was tested by enzyme-linked immunospot (ELISPOT) assay. Cells were stimulated 18 h by concanavalin A (5 µg/ml; Sigma) as a positive control, RPMI-IL-2 (10 U/ml) as a negative control, CHIKV (MOI 1), or MV (MOI 1). Multiscreen-HA 96-well plates were coated overnight at 4° C. with 5 µg of anti-mouse IFN-γ/ml (R4-6A2; Pharmingen) in PBS, washed, and then incubated with 100 µl of RPMI and 10% FCS for 1 h at 37° C. The medium was replaced by 100 µl of cell suspension ($5\times10^5$ splenocytes per well in triplicate) and 100 µl of stimulating agent. After 2 h at 37° C., heated-FCS (10%) was added, and the plates were incubated for 18 h at 37° C. After washing, biotinylated anti-mouse IFN-α antibody (XMG1.2; Pharmingen) was added and the plates were incubated for 2 hours at room temperature. Streptavidin-alkaline phosphatase conjugate (Roche) was used as secondary step. Spots were developed with BCIP/NBT (Promega) and counted (ELISpot Reader; Bio-Sys).

Expression of CHIKV virus-like particles by recombinant MV vector. CHIKV VLPs have been shown to elicit protective immunity against CHIKV infection (Akahata, W., et al., A virus-like particle vaccine for epidemic Chikungunya virus protects nonhuman primates against infection. Nat Med, 2010. 16(3): p. 334-8). To benefit of this capacity, the inventors designed a recombinant MV vector able to induce the secretion of CHIKV VLPs. To this aim, a cDNA encoding the C-E3-E2-6K-E1 structural proteins required for CHIKV VLPs production was chemically synthetized (Genscript) and optimized for measles virus expression in mammalian cells, then introduced into an additional transcription unit (ATU) of the Schwarz MV vaccine infectious cDNA (FIG. 1). The recombinant MV-CHIKV virus was obtained by transfecting this plasmid into HEK-293 helper cells and propagation on Vero cells. Virus stocks were grown on Vero cells and titer was determined.

High amounts of CHIKV VLPs were secreted in the culture medium of infected cells, as demonstrated by immunofluorescence, western blot and electron microscopy.

This strategy provides a live recombinant MV vaccine virus secreting CHIKV VLPs at each round of replication. It was not expected that the assembly of native alphavirus particles would take place and that these VLPs would not hamper the simultaneous replication of a paramyxovirus. This is demonstrated here for the first time. Because MV vaccine is industrially produced as a crude viral extract, the batches of recombinant MV-CHIKV contain both live MV virus and non-replicating CHIKV VLPs. This strategy allows benefiting of the advantageous immunogenic property of multimeric antigens displayed on VLPs with no need of fastidious and expensive purification and concentration process. Moreover, no adjuvant is needed as the VLPs benefit of the advantageous immunogenic characteristics of live vaccines, such as balanced Th1 response and long-term memory.

Figures 2, 3:
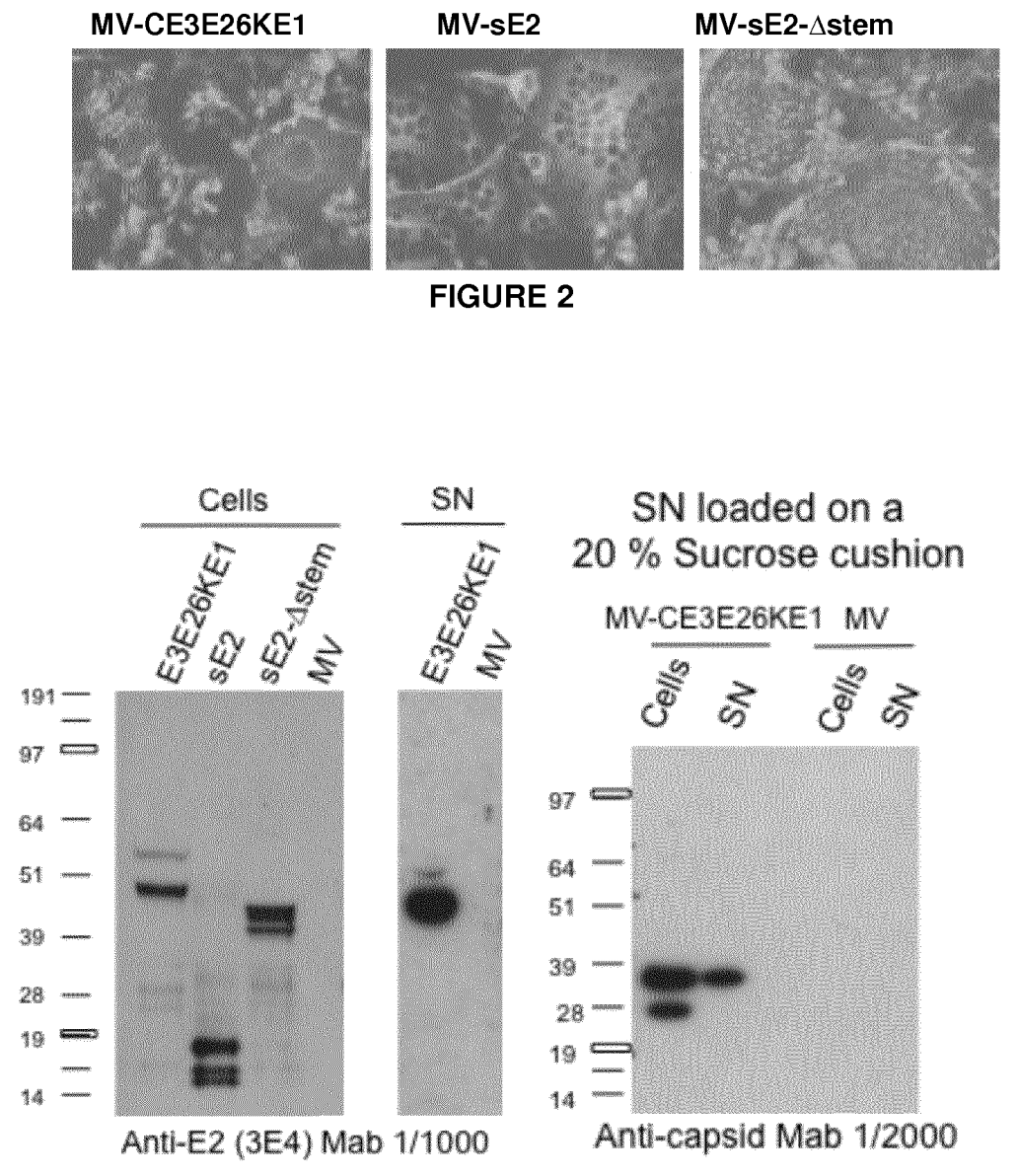

The expression of CHIKV E2 and capsid antigens was demonstrated in infected Vero cells by immunofluorescence using a specific antibody (Mab 3E4) directed against the E2 protein of CHIKV (FIG. 2). To look for the presence of secreted VLPs, the culture medium of infected cells was clarified by low-speed centrifugation, then layered onto a 20% sucrose cushion and concentrated by centrifugation at 41,000 rpm for 2 h in a SW41 rotor. Pellets were dissolved in PBS with 1% BSA. Proteins extracted from cell lysates and from concentrated culture media were fractionated by SDS-PAGE gel electrophoresis and transferred to cellulose membranes. The blots were probed with the 3E4 mouse Mab produced by hybridoma deposited at the CNCM (Collection Nationale de Cultures de Microorganismes, Paris, France) on Sep. 6, 2007 under number 1-3824, in the name of Institut Pasteur for the detection of E2 and an anti-capsid Mab (FIG. 3).

The E2 protein was found both in cell lysates and in concentrated supernatant of infected cells at the correct size (46 KDa), indicating the capacity of MV-CHIKV virus to induce the secretion of high-density particles containing the E2 protein. The capsid protein was also found in high-density particles, confirming the formation of CHIKV-VLPs. The presence of both C and E2 proteins in concentrated supernatant of infected cells suggests the formation of CHIKV VLPs. To observe their physical presence, the inventors analyzed by electron microscopy the pellets concentrated from supernatant of MV-CHIKV infected cells. The images revealed the presence of high amount of particles of size and morphology similar to those described after wild type CHIKV infection (Pletnev, S. V., et al., Locations of carbohydrate sites on alphavirus glycoproteins show that E1 forms an icosahedral scaffold. Cell, 2001. 105(1): p. 127-36; Zhang, W., et al., Placement of the structural proteins in Sindbis virus. J Virol, 2002. 76(22): p. 11645-58) (FIG. 4). The observed particles present an external diameter of 65 nm and a core diameter of 40 nm. The surface organization indicates the presence of spikes on the surface of the VLPs, similarly arranged than for other alphaviruses (Pletnev, S. V., et al., Locations of carbohydrate sites on alphavirus glycoproteins show that E1 forms an icosahedral scaffold. Cell, 2001. 105(1): p. 127-36; Zhang, W., et al., Placement of the structural proteins in Sindbis virus. J Virol, 2002. 76(22): p. 11645-58). This observation confirms that infection of Vero cells by recombinant MV-CHIKV virus enables the secretion of high amounts of CHIK VLPs that self assemble.

The E2 protein was also expressed and secreted at the correct size (46 KDa) by cells infected with Measles virus-sE2Δstem recombinant viruses, and Measles virus-CE3E26KE1 recombinant viruses.

Unfortunately, the analysis of MV-sE2 infected cells showed repeatedly the expression of a truncated form of the E2 protein. The inventors sequenced the E2 mRNA produced by MV-sE2 virus after RT-PCR amplification of infected cells. The analysis demonstrated the presence of a mutation generating a STOP codon, responsible for the truncation (FIG. 5).

The inventors then compared the replication rate of Measles Virus-sE2, Measles Virus-sE2Δstem, and Measles Virus-CE3E26KE1 recombinant viruses on Vero cells to standard Measles virus stock production, using a low MOI (0.01) (FIG. 6). The growth of MV-sE2 was similar to that of control MV. The growth of Measles virus-sE2Δstem and Measles virus-CE3E26KE1 recombinant viruses was slightly delayed, but their final titers were in the same range as that of empty Measles virus.

Immunogenicity of MV-sE2 and MV-CE3E26KE1 and Protection in CD46-IFNAR Mice.

CD46-IFNAR mice susceptible to MV infection were used to assess the immunogenicity of the recombinant MV-CHIKV viruses and their protective efficacy. These mice express the human CD46 gene with human-like tissue specificity and lack the type-I interferon receptors. Mice were housed under specific pathogen-free conditions at the Pasteur Institute animal facility and all experiments were approved and conducted in accordance with the guidelines of the Office of Laboratory Animal Care at Pasteur Institute. Six-week-old CD46-IFNAR mice were inoculated intraperitoneally (i.p.) with doses ranging from $10^3$ to $10^5$ TCID50 of MV-CHIKV recombinant viruses and boosted 1 month later with the same dose of recombinant viruses. Control mice were immunized with the same dose of empty MVSchw vector. For antibody determination, blood samples were collected via the periorbital route 1 month after the first inoculation, then at 2 or 4 weeks after boosting.

Previous studies have shown that IFNAR mice are susceptible to lethal Chikungunya virus infection, showing pathological manifestations of infection and providing a model to evaluate immune mechanisms of protection (Couderc et al; 2008).

CD46-IFNAR mice susceptible to Measles virus infection were used to assess the immunogenicity of the recombinant Measles-Chikungunya viruses and their protective efficacy. These mice express the human CD46 gene with human-like tissue specificity and lack the type-I interferon receptors. Mice were housed under specific pathogen-free conditions at the Pasteur Institute animal facility and all experiments were

Experiment 1

Analysis of the Immunogenicity and the Protective Efficacy of Measles Virus-CE3E26KE1 Recombinant Viruses in CD46-IFNAR Mice Six-week-old CD46-IFNAR mice susceptible to Measles virus infection were intraperitoneally inoculated with $2.10^4$ $TCID_{50}$ of Measles virus-Chikungunya virus recombinant viruses and boosted 1 month later with the same dose of recombinant viruses. Control mice were immunized with the same dose of empty Measles virus Schwarz vector (MV Schw). For antibody determination, blood samples were collected via the periorbital route 1 month after the first inoculation, then at 2 weeks after boosting. Mice were then challenged by i.p. injection of 100 pfu of Chikungunya virus 06-49 strain for evaluating protection (Immunization and challenge schedule is given in FIG. 7).

To evaluate the specific antibody responses, mice were bled at different time-points after inoculation. Sera were heat inactivated at 56° C. for 30 min and anti-Chikungunya virus antibodies were detected by ELISA. 96-well plates were coated with recombinant Chikungunya virus-E2 protein produced in *E. coli*. HRP-conjugated anti-mouse immunoglobulin was used as secondary antibody and mouse antibodies anti-Chikungunya virus was used as a positive control. Anti-Chikungunya virus neutralizing antibodies were detected by a plaque reduction neutralization test (PRNT) (Warter L et al. JIM 2011 (D4 enclosed) and Russell P K et al. JIM 1967) on Vero cells using 50 PFU of Chikungunya virus-06-49 (produced on Vero cells). The endpoint titer was calculated as the highest serum dilution tested that reduced the number of PFU by at least 50% (PRNT50) or 90% (PRNT90).

A single injection of Measles virus-CE3E26KE1 recombinant viruses induced high antibody titers, which were strongly boosted by a second injection (table1—FIG. 8). After two immunizations, high neutralizing titers were induced (PRNT50=450-4050 and PRNT90=50-450). All animals immunized with 104 or 105 TCID50 were protected from CHIKV lethal challenge with 100 PFU of CHIKV-06-49, whereas immunization with the lower dose (103 TCID50) protected 83% of the animals.

TABLE 1

Antibody response of CD46-IFNAR mice to immunization with MV-sE2 and MV-CE3E26KE1 (determined in pooled mice sera)

|  | Elisa 1 dose | Elisa 2 dose | PRNT50 | PRNT90 |
| --- | --- | --- | --- | --- |
| MV | <100 | <100 | <50 | <50 |
| MV-CHIK.SE2 | 450 | 4000 | <50 | <50 |
| MV-CHIK.CE3E26KE1 | 4000 | >12000 | 1350 | 150 |
| Anti-CHIKV HMAF | ND | ND | 4050 | 450 |

After two immunizations, high neutralizing titers were induced (PRNT50=1350 and PRNT90=150) that protected mice from a lethal challenge with 100 PFU of Chikungunya virus-06-49.

Experiment 2

Analysis of the Immunogenicity and the Protective Efficacy of a Single Dose of Measles Virus-CE3E26KE1 Recombinant Virus in CD46-IFNAR Mice Six-week-old CD46-IFNAR mice were i.p. inoculated with $10^5$ $TCID_{50}$ of Measles virus-CE3E26KE1 recombinant viruses. Control mice were immunized with the same dose of empty Measles virus Schw vector. Blood samples were collected via the periorbital route 2 weeks after immunization for antibody determination, and then mice were challenged by i.p. injection of 100 pfu of Chikungunya virus 06-49 (Immunization and challenge schedule is given in FIG. 9).

The Measles virus-CE3E26KE1 recombinant viruses induced high antibody titers after a single injection (table 2—FIG. 10), and neutralizing titers that were sufficient to confer protection against a lethal challenge with 100 PFU of Chikungunya virus-06-49 in IFNAR mice.

TABLE 2

Antibody response elicited in CD46-IFNAR mice after a single immunization with MV-CE3E26KE1 virus

|  | MV Elisa titer | CHIKV Elisa titer | CHIKV PRNT50 | CHIKV PRNT90 |
| --- | --- | --- | --- | --- |
| MV | 10 000 | <100 | <50 | <50 |
| MV-CHIKV | 10 000 | 4 050 | 150 | 50 |
| Anti-CHIKV HMAF | ND | ND | 12150 | 450 |

Experiment 3

Determination of the Protective Dose of Measles Virus-CE3E26KE1 Recombinant Virus in CD46-IFNAR Mice Six-week-old CD46-IFNAR mice were inoculated intraperitoneally (i.p.) with doses ranging from $10^3$ to $10^5$ TCID50 of MV-CHIKV recombinant virus and boosted one month later with the same dose. Control mice were immunized with the same dose of empty MVSchw vector. One month after the last immunization, mice were challenged by i.p. injection of 100 pfu of CHIKV 06-49 (Immunization and challenge schedule is given in FIG. 11). For antibody determination, blood samples were collected via the periorbital route 1 month after the first inoculation, then 1 month after boosting, just before challenge. Specific Elisa's were performed to detect anti-MV and anti-CHIKV binding antibodies. Anti-CHIKV neutralizing antibodies titers were determined by a plaque reduction neutralization test (PRNT) on Vero cells.

Figure 12:
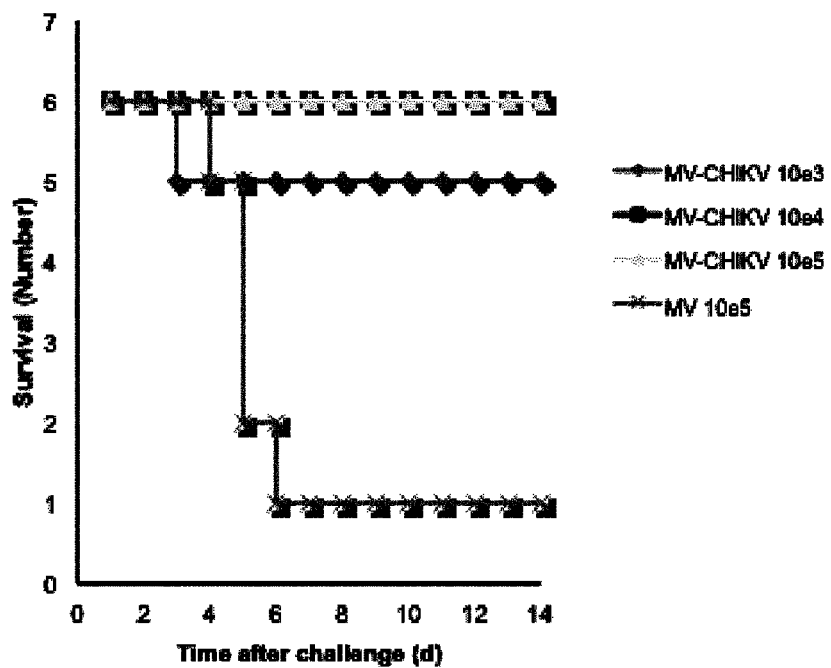
FIG. 12: Survival curve of mice lethally challenged with 100 PFU of CHIKV-06-49 after immunization with different doses of MV-CE3E26KE1 recombinant virus.

The results are given in table 3 and FIG. 12.

TABLE 3

Antibody response after immunization with different doses of MV-CE3E26KE1

| | 1st immunisation | | | | $2^{nd}$ immunisation | | | |
|---|---|---|---|---|---|---|---|---|
| | MV Elisa titer | CHIKV Elisa titer | CHIKV PRNT50 | CHIKV PRNT90 | MV Elisa titer | CHIKV Elisa titer | CHIKV PRNT50 | CHIKV PRNT90 |
| MV $10^5$ | 10 000 | <100 | <50 | <50 | 300 000 | <100 | <50 | <50 |
| MV-CHIKV $10^3$ | 1 000 | 1 350 | 50 | <50 | 3 000 | 2 700 | 450 | 50 |
| MV-CHIKV $10^4$ | 3 000 | 4 050 | 150 | 50 | 30 000 | 12 150 | 1 350 | 150 |
| MV-CHIKV-$10^5$ | 3 000 | 12 150 | 450 | 150 | 300 000 | 48 600 | 4 050 | 450 |

Both anti-MV and anti-CHIKV antibody titers increased when the dose of recombinant MV increased. A single immunization with MV-CE3E26KE1 virus induced high antibody titers, which were boosted by the second injection. After two immunizations, high neutralizing titers were induced (PRNT50=450-4050 and PRNT90=50-450). All animals immunized with $10^4$ or $10^5$ TCID$_{50}$ were protected from CHIKV lethal challenge with 100 PFU of CHIKV-06-49, whereas immunization with the lower dose ($10^3$ TCID50) protected 83% of the animals (FIG. 12).

Experiment 4

Evaluation of the Protection Conferred by Passive Transfer of Sera from Mice Immunized with Recombinant MV-CE3E26KE1 Virus Six-week-old CD46-IFNAR mice were i.p. inoculated with 20 µl of pooled sera from mice immunized with $10^5$ TCID50 of recombinant MV-CE3E26KE1. Control mice received either 20 µl of pooled sera from mice immunized with $10^5$ TCID50 of empty Measles virus Schwarz or 20 µl of anti-Chikungunya virus HMAF. The sera were diluted in a total volume of 100 µl PBS. The sera were transferred at 24 h and 16 h before challenge with 100 pfu of Chikungunya virus 06-49, and then 12 h post-challenge to mimic antibody persistence in infected animals. Mice mortality was analyzed for 2 weeks to determine protection (Immunization and challenge schedule is given in FIG. 13).

Passive transfer of immune sera of mice immunized with MV-CE3E26KE1 virus protected 83% of recipient mice from lethal Chikungunya virus challenge, while mice that received anti-Chikungunya virus HMAF were fully protected. In contrast, mice that received immune sera from mice immunized with empty Measles viruses all died. These results indicate that humoral immune responses induced by Measles virus-CE3E26KE1 recombinant viruses confer protection against Chikungunya virus infection in CD46-IFNAR mice (FIG. 14).

Experiment 5

Induction of Specific Cell-mediated Immune Responses

Figure 15:
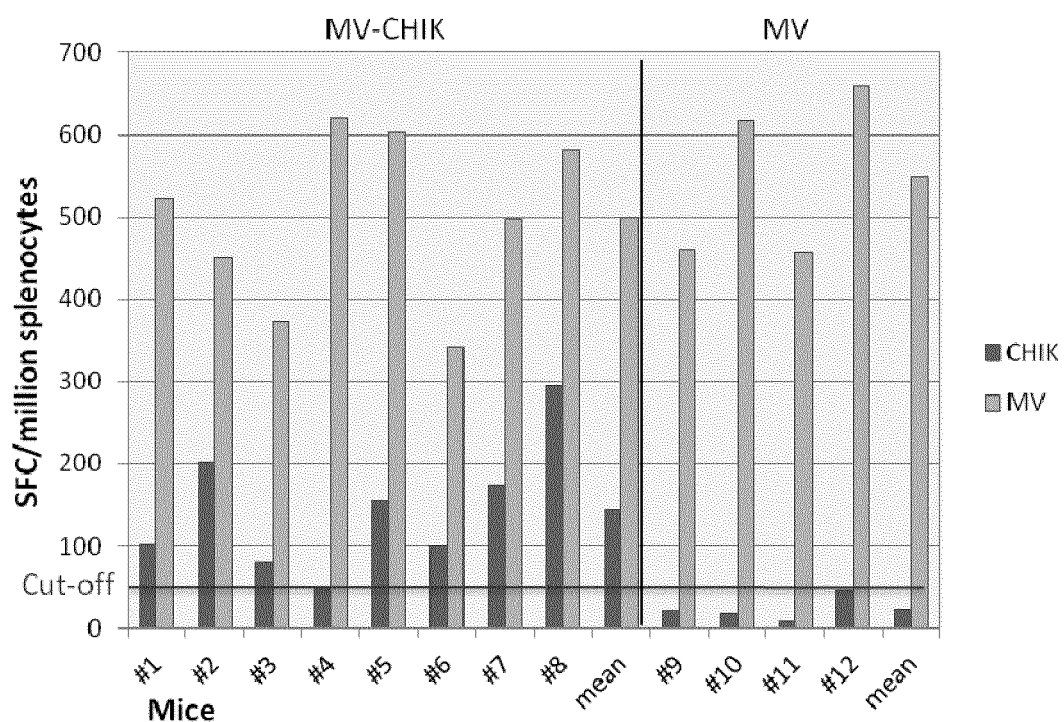
FIG. 15: Cell-mediated immune responses elicited in splenocytes of CD46-IFNAR mice immunized by a single injection of 106 TCID50 of MV-CHIKV.

To determine whether immunization with MV-CHIKV elicited cell-mediated immune responses, we measured by ELISPOT assay the capacity of splenocytes from immunized mice to secrete IFN-γ upon specific ex-vivo stimulation. Splenocytes were collected 7 days after a single immunization and both MV-specific and CHIKV-specific responses were evaluated. CHIKV and MV were used at an MOI of 1 for splenocytes stimulation. A significant number of CHIKV-specific cells (up to 300/106 splenocytes, mean 150/106) were detected (FIG. 15), which represents one third of MV-specific response in similar stimulation condition (up to 600/106 splenocytes, mean 500/106). All mice immunized with MV-CHKV, except one out of eight, had a significant CMI response to CHIKV. In contrast, control mice immunized with empty MVSchw had a similar MV-specific response but no CHIKV-specific response. These results show that a single inoculation of MV-CHIKV induced high levels of CHIKV- and MV-specific cellular immune response in the spleen of immunized mice.

Experiment 6

Analysis of Measles Virus Pre-immunity Impact on the Immunogenicity and Protective Efficacy of Recombinant MV-CE3E26KE1 Virus in CD46-IFNAR Mice Six-week-old CD46-IFNAR mice were i.p. inoculated with $5.10^3$ TCID$_{50}$ of empty Measles virus Schwarz (Group1 FIG. 16) to mimic pre-immunity. Three months later, these mice were injected twice with $10^5$ TCID$_{50}$ of Measles virus-CE3E26KE1 recombinant viruses at one month of interval. Control mice were immunized with $10^5$ TCID$_{50}$ of Measles virus-CE3E26KE1 recombinant viruses (Group 2) or $10^5$ TCID$_{50}$ of empty Measles virus Schw (Group 3). For antibody determination, blood samples were collected via the periorbital route as indicated in FIG. 16, and mice were then challenged by i.p. injection of 100 pfu of Chikungunya virus 06-49 strain for protection assays.

This experiment demonstrates that CD46-IFNAR mice previously immunized with $5.10^3$ TCID50 of empty Measles viruses are able to mount a protective Chikungunya virus immune response after immunization with Measles virus-CE3E26KE1 recombinant viruses. The ELISA and PRNT titers (Table 4—FIG. 17) remain high and in the same range of that induced in naive mice (ELISA titer unchanged and PRNT titers reduced by one-fold dilution). 100% of the vaccinated animals were protected from Chikungunya virus lethal challenge in both pre-immune and naive groups of animals immunized with Measles virus-CE3E26KE1 recombinant viruses.

TABLE 4

Antibody response of CD46-IFNAR mice to MV-CE3E26KE1 in the presence of pre-immunity to MV vector

| | Immunizations | | | | | | | | |
|---|---|---|---|---|---|---|---|---|---|
| | 1st | 2nd | | | | 3rd | | | |
| | MV Elisa | MV Elisa | CHIKV Elisa | CHIKV PRNT50 | CHIKV PRNT90 | MV Elisa | CHIKV Elisa | CHIKV PRNT50 | CHIKV PRNT90 |
| MV + MV-CHIKV | 3 000 | 30 000 | 12 150 | 150 | 50 | 30 000 | 150 000 | 12 150 | 150 |
| MV-CHIKV | ND | 10 000 | 12 150 | 450 | 150 | 100 000 | 150 000 | 12 150 | 450 |
| MV | ND | 10 000 | <50 | <50 | <50 | 100 000 | <50 | <50 | <50 |

Experience-7

Cross-reactivity of Abs Elicited by Vaccination

To determine whether immunization with MV-CHIKV elicited cross-reactive antibody response to different CHIKV primary isolates, sera obtained from animals of experiment 4 were tested for their ability to neutralize different CHIKV primary isolates. Four strains belonging to the ECSA genotype were chosen.

CHIKV strain India, clinical isolate no 3710 (NRC for Arbovirus, France), isolated in 2011. Passage 1 on Vero cells (December 2011), virus titer 6.3 log PFU/ml CHIKV strain Congo, clinical isolate no 525 (NRC for Arbovirus, France), isolated in 2011. Passage 1 on Vero cells (June 2011), virus titer 6.5 log PFU/ml CHIKV strain Thailand, clinical isolate no 1499 (NRC for Arbovirus, France), isolated in 2009. Passage on C6/36 cells (December, 2009), virus titer 6.3 log PFU/ml CHIKV strain La Reunion, clinical isolate 2006.49 (NRC for Arbovirus, France), isolated in 2006. Passage 3 on Vero cells (Apr. 4, 2011), virus titer 7.3 log PFU/ml Anti-CHIKV neutralizing antibodies were detected by use of a plaque reduction neutralization test (PRNT). Vero cells were seeded into 12 µwell plates for 24 h. Serum samples were serially diluted in DMEM Glutamax/2% FCS. Dilutions 100 µl were incubated for 2 h at 37° C., under gentle agitation, with an equal volume of CHIKV containing 100 pfu of 06-49 strain. Remaining infectivity was then assayed on Vero cell monolayers overlaid with DMEM GlutaMAX/2% FCS containing 0.8% final (wt/vol) carboxy methylcellulose. After 3 days of incubation, cells were fixed and stained with crystal violet for plaque count determination. The endpoint neutralization titer was calculated as the highest serum dilution tested that reduced the number of plaques by at least 50% ($PRNT_{50}$).

TABLE 5

Cross-reactivity of neutralizing Ab from mice immunized with MV-CHIKV

| | PRNT50 post 1st | | PRNT50 post 2nd | | PRNT50 post challenge | |
|---|---|---|---|---|---|---|
| | MV-CHIKV | MV | MV-CHIKV | MV | MV-CHIKV | MV |
| 06-49 | 50 | <50 | 1350 | <50 | 450 | ND |
| Inde | 150 | <50 | 1350 | <50 | 13250 | ND |
| Congo | <50 | <50 | 1350 | <50 | 1350 | ND |
| Thai | 150 | <50 | 4050 | <50 | 12150 | ND |

The result shows that immunization of mice with MV-CHIKV induces cross-reactive antibodies that are able to neutralize several primary isolates of CHIKV from different countries. Interestingly, the challenge of animals with the 06-49 La Reunion virus results in even broadening the response and boosts the neutralization of Indian and Thai isolates to very strong levels. Only ECSA genotype was tested because of its availability at Institut Pasteur.

Experience-8

Immunogenicity of MV-CHIKV in Cynomolgus Macaques

The immunogenicity of recombinant measles virus vaccine against Chikungunya was tested in non-human primates. Two groups of four cynomolgus macaques (*macaca fascicularis*) previously selected to be seronegative for flaviviruses and measles virus were vaccinated subcutaneously with $10^4$ or $10^5$ $TCID_{50}$ MV-CHIKV on day 0 then boosted on day 90 with the same dose. Serum and plasma were collected and stored at −20° C. for later analysis. Neutralizing antibodies to Chikungunya virus were detected by using a PRNT assay.

TABLE 6

| | | | | | Reciprocal CHIK-PRNT | | | |
|---|---|---|---|---|---|---|---|---|
| Group | Animal | Code | Vaccine | Dose | Day 0 | Day 21 | Day 90 | Day 111 |
| D | D1 | 12/9 | MV-CHIK | $10^4$ | <10 | 574 | <10 | 14 |
| | D2 | 12/4 | MV-CHIK | $10^4$ | <10 | 142 | 73 | 97 |
| | D3 | 12/5 | MV-CHIK | $10^4$ | <10 | 16 | 17 | 121 |
| | D4 | 12/10 | MV-CHIK | $10^4$ | <10 | 70 | 83 | 118 |
| E | E1 | 12/16 | MV-CHIK | $10^5$ | <10 | 247 | 101 | 382 |
| | E2 | 12/23 | MV-CHIK | $10^5$ | <10 | 103 | 178 | 355 |
| | E3 | 12/26 | MV-CHIK | $10^5$ | <10 | 6173 | 151 | 652 |
| | E4 | 12/22 | MV-CHIK | $10^5$ | <10 | 97 | 386 | 228 |

Figure 18:
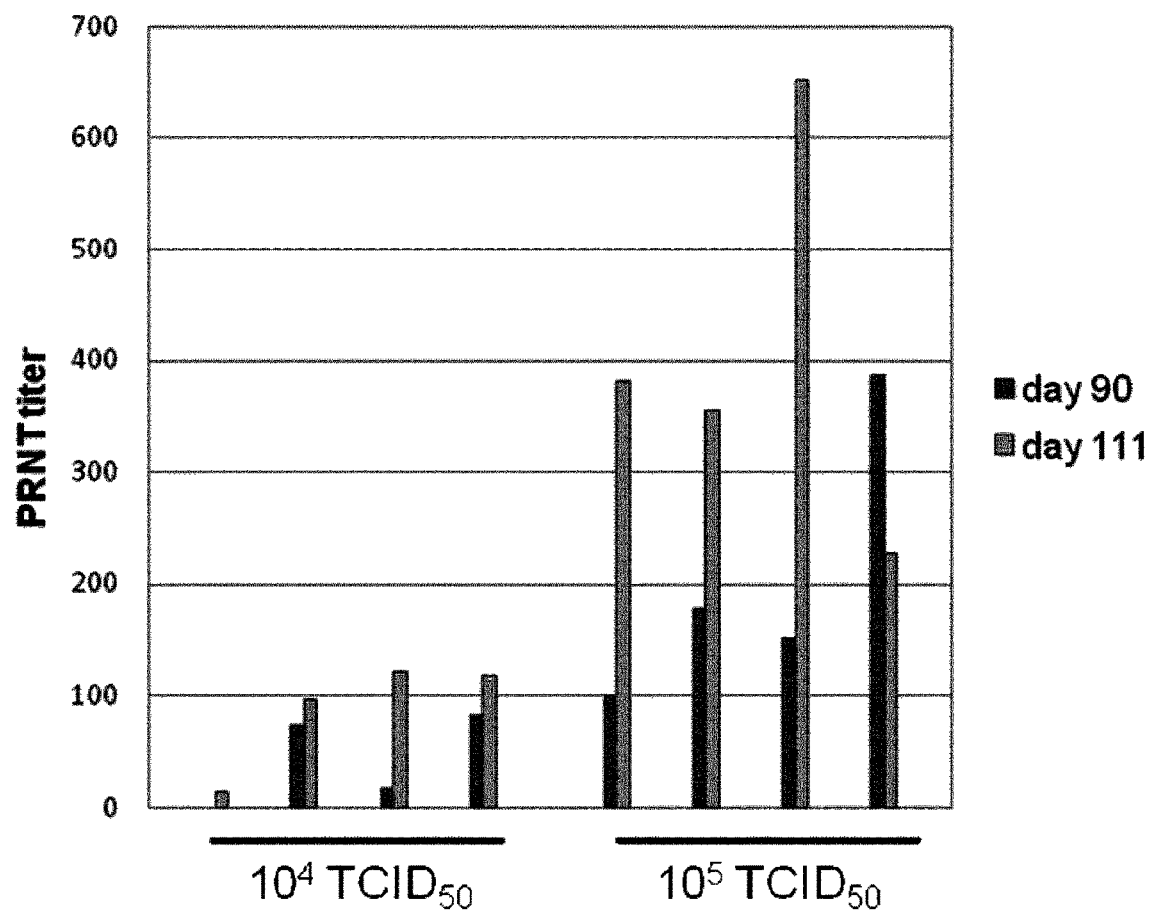
FIG. 18: PRNT assays performed against CHIK prior to first immunization on day 90 (prior to boost) and day 111 (21 days after boost).

Results presented in Table 6 show that all monkeys developed high titers of antibodies that neutralized CHIKV. The highest dose was more efficient than the lower dose. In most animals, boosting was efficient, as shown on FIG. 18 (day 90, the day of boost versus day 111, 21 days after boost). These results demonstrate the immunogenicity of MV-CHIKV vaccine candidate in non-human primates.

GENERAL CONCLUSION

The inventors have generated a recombinant MV-CHIK virus expressing stably the complete structural proteins CE3E26KE1 of CHIKV strain 06.49. Vero cells infected by this recombinant virus expressed high levels of CHIKV proteins and secreted high density VLPs. The recombinant virus was slightly delayed in growth kinetics but yielded similar titers that empty MV vector. Evaluated in CD46-

IFNAR mice susceptible to MV infection, this vaccine candidate induced high levels of neutralizing antibodies to CHIKV depending on the dose and number of administrations (PRNT50 =450-4050; PRNT90=150-450). All immunized mice were repeatedly protected, even after a single administration, demonstrating the strong immune capacity of this vaccine candidate. The passive transfer of immune sera in naïve animals conferred protection from lethal challenge, even in these highly susceptible mice. Lastly, the inventors demonstrated that the presence of pre-existing immunity to MV vector in CD46-IFNAR mice did not prevent the induction of protective immunity after immunization with MV-CE3E26KE1 vaccine candidate. In view of the results, the recombinant vector thus obtained deserves to be evaluated in a reliable non-human primate model of infection.

The invention claimed is:

1. A nucleic acid construct which comprises:
   (1) a polynucleotide encoding the C-E3-E2-6K-E1 structural proteins of a Chikungunya virus (CHIKV); and
   (2) a cDNA molecule which encodes a full-length, infectious antigenomic (+) RNA strand of a measles virus (MV);
   wherein the polynucleotide encoding the C-E3-E2-6K-E1 structural proteins and the cDNA molecule are operatively linked.

2. The nucleic acid construct according to claim 1, wherein said cDNA molecule consists of a number of nucleotides that is a multiple of six.

3. The nucleic acid construct according to claim 1, comprising the following polynucleotides from 5' to 3':
   (a) a polynucleotide encoding a full length of N protein of the MV,
   (b) a polynucleotide encoding a full length of P protein of the MV,
   (c) the polynucleotide encoding the C-E3-E2-6K-E1 structural proteins of CHIKV,
   (d) a polynucleotide encoding a full length of M protein of the MV,
   (e) a polynucleotide encoding a full length of F protein of the MV,
   (f) a polynucleotide encoding a full length of H protein of the MV, and
   (g) a polynucleotide encoding a full length of L protein of the MV,
   wherein said polynucleotides are operably linked in the nucleic acid construct and under a control of viral replication and transcription regulatory sequences.

4. The nucleic acid construct according to claim 1, wherein said Measles virus is an attenuated virus strain selected from the group consisting of the Schwarz strain, the Zagreb strain, the AIK-C strain and the Moraten strain.

5. The nucleic acid construct according to claim 1, wherein said polynucleotide encoding the C-E3-E2-6K-E1 structural proteins of CHIKV has been optimized for a Macacca codon usage or has been optimized for a human codon usage.

6. The nucleic acid construct according to claim 1, wherein said polynucleotide encoding the C-E3-E2-6K-E1 structural proteins comprises at least one measles editing-like sequence selected from AAAGGG, AAAAGG, GGGAAA, and GGGGAA that has been mutated.

7. The nucleic acid construct according to claim 1, wherein said Chikungunya virus is from the strain designated 06-49 strain.

8. The nucleic acid construct according to claim 1, wherein the encoded E2 structural protein comprises an amino acid sequence selected from the group consisting of SEQ ID NO: 11, SEQ ID NO: 13, and SEQ ID NO: 15.

9. The nucleic acid construct according to claim 1, wherein said nucleic acid construct encodes C-E3-E2-6K-E1 structural proteins having a sequence selected from the group consisting of SEQ ID NO: 21, SEQ ID NO: 22, SEQ ID NO: 23, SEQ ID NO: 24, SEQ ID NO: 25, SEQ ID NO: 26 and SEQ ID NO: 28.

10. The nucleic acid construct according to claim 1, wherein said nucleic acid construct comprises a sequence selected from the group consisting of SEQ ID NO: 20, SEQ ID NO: 27, and SEQ ID NO: 31.

11. A transfer vector plasmid, comprising the nucleic acid construct of claim 1.

12. The vector according to claim 11, wherein said vector is pMV-CHIKV.

13. Transformed eukaryotic cells comprising the nucleic acid construct according to claim 1.

14. Recombinant infectious replicating MV-CHIKV particles produced by a method comprising expressing the nucleic acid construct according to claim 1 in a host cell comprising an RNA polymerase recognized by said host cell, a nucleoprotein (N) of a MV, and a phosphoprotein (P) of a MV.

15. The recombinant infectious replicating MV-CHIKV particles of claim 14, wherein said virus particles are encoded by a polynucleotide sequence comprising a sequence selected from the group consisting of SEQ ID NO: 27 and SEQ ID NO: 31.

16. A composition comprising the recombinant infectious replicating MV-CHIKV particles according to claim 14, CHIKV-C-E3-E2-6K-E1 Virus Like Particles (VLPs) and a pharmaceutically acceptable vehicle.

17. A method of inducing a protective immune response against CHIKV in a host, comprising administering the composition according to claim 16 to the host.

18. A method of treating or preventing an infection by CHIKV in a host, comprising administering the composition according to claim 16 to the host.

19. A process to rescue recombinant measles virus (MV) expressing the C-E3-E2-6K-E1 structural proteins of a Chikungunya virus (CHIKV) and CHIKV-C-E3-E2-6K-E1 Virus Like Particles (VLPs), comprising:
 1) cotransfecting helper cells that stably express T7 RNA polymerase, and measles N and P proteins with (i) a transfer vector plasmid according to claim 14, and (ii) a vector, encoding the MV L polymerase;
 2) cultivating said cotransfected helper cells in conditions enabling the production of MV-CHIKV recombinant virus;
 3) propagating the thus produced recombinant virus by co-cultivating said helper cells of step 2) with cells enabling said propagation; and
 4) recovering replicating MV-CHIKV recombinant virus expressing the C-E3-E2-6K-E1 structural proteins of CHIKV and CHIKV-C-E3-E2-6K-E1 VLPs.

20. The process according to claim 19, wherein the transfer vector plasmid comprises a sequence selected from the group consisting of SEQ ID NO: 27 and SEQ ID NO: 31.

* * * * *

SEQUENCE LISTING

```
<160> NUMBER OF SEQ ID NOS: 33

<210> SEQ ID NO 1
<211> LENGTH: 18967
<212> TYPE: DNA
<213> ORGANISM: Artificial Sequence
<220> FEATURE:
<223> OTHER INFORMATION: pTM-MVSchw (GenBank: FW366202.1)

<400> SEQUENCE: 1
gcggccgcta atacgactca ctatagggcc aactttgttt ggtctgatga gtccgtgagg      60
acgaaacccg gagtcccggg tcaccaaaca aagttgggta aggatagttc aatcaatgat     120
catcttctag tgcacttagg attcaagatc ctattatcag gacaagagc aggattaggg      180 atatccgaga tggccacact tttaaggagc ttagcattgt tcaaaagaaa caaggacaaa     240
ccacccatta catcaggatc cggtggagcc atcagaggaa tcaaacacat tattatagta     300
ccaatccctg gagattcctc aattaccact cgatccagac ttctggaccg gttggtgagg     360
ttaattggaa acccggatgt gagcgggccc aaaactaacag gggcactaat aggtatatta     420
tccttatttg tggagtctcc aggtcaattg attcagagga tcaccgatga ccctgacgtt     480
agcataaggc tgttagaggt tgtccagagt gaccagtcac aatctggcct taccttcgca     540
tcaagaggta ccaacatgga ggatgaggcg gaccaatact tttcacatga tgatccaatt     600
agtagtgatc aatccaggtt cggatggttc gggaacaagg aaatctcaga tattgaagtg     660
caagaccctg agggattcaa catgattctg ggtaccatcc tagcccaaat ttgggtcttg     720
ctcgcaaagg cggttacggc cccagacacg gcagctgatt cggagctaag aaggtggata     780
aagtacaccc aacaaagaag ggtagttggt gaatttagat tggagagaaa atggttggat     840
gtggtgagga acaggattgc cgaggacctc tccttacgcc gattcatggt cgctctaatc     900
ctggatatca agagaacacc cggaaacaaa cccaggattc tgaaatgat atgtgacatt     960 gatacatata tcgtagaggc aggattagcc agttttatcc tgactattaa gtttgggata    1020
gaaactatgt atcctgctct tggactgcat gaatttgctg gtgagttatc cacacttgag    1080
tccttgatga acctttacca gcaaatgggg gaaactgcac cctacatggt aatcctggag    1140
aactcaattc agaacaagtt cagtgcagga tcatacccctc tgctctggag ctatgccatg    1200
ggagtaggag tggaacttga aaactccatg ggaggtttga cttttggccg atcttacttt    1260
gatccagcat attttagatt agggcaagag atggtaagga ggtcagctgg aaaggtcagt    1320
tccacattgg catctgaact cggtatcact gccgaggatg caaggcttgt ttcagagatt    1380
gcaatgcata ctactgagga caagatcagt agagcggttg gacccagaca agcccaagta    1440
tcatttctac acggtgatca aagtgagaat gagctaccga gattgggggg caaggaagat    1500
aggagggtca aacagagtcg aggagaagcc agggagagct acagagaaac cgggcccagc    1560
agagcaagtg atgcgagagc tgcccatctt ccaaccggca caccctaga cattgacact    1620 gcaacggagt ccagccaaga tccgcaggac agtcgaaggt cagctgacgc cctgcttagg    1680
```

```
ctgcaagcca tggcaggaat ctcggaagaa caaggctcag acacggacac ccctatagtg    1740
tacaatgaca gaaatcttct agactaggtg cgagaggccg agggccagaa caacatccgc    1800
ctaccatcca tcattgttat aaaaaactta ggaaccaggt ccacacagcc gccagcccat    1860
caaccatcca ctcccacgat tggagccaat ggcagaagag caggcacgcc atgtcaaaaa    1920
cggactggaa tgcatccggg ctctcaaggc cgagcccatc ggctcactgg ccatcgagga    1980
agctatggca gcatggtcag aaatatcaga aacccagga caggagcgag ccacctgcag    2040
ggaagagaag gcaggcagtt cgggtctcag caaaccatgc ctctcagcaa ttggatcaac    2100
tgaaggcggt gcacctcgca tccgcggtca gggacctgga gagagcgatg acgacgctga    2160
aactttggga atccccccaa gaaatctcca ggcatcaagc actgggttac agtgttatta    2220
cgtttatgat cacagcggtg aagcggttaa gggaatccaa gatgctgact ctatcatggt    2280
tcaatcaggc cttgatggtg atagcaccct ctcaggagga caatgaat ctgaaaacag     2340
cgatgtggat attggcgaac ctgataccga gggatatgct atcactgacc ggggatctgc    2400
tcccatctct atggggttca gggcttctga tgttgaaact gcagaaggag gggagatcca    2460
cgagctcctg agactccaat ccagaggcaa caactttccg aagcttggga aaactctcaa    2520
tgttcctccg cccccggacc ccgtagggc cagcacttcc gggacaccca ttaaaaaggg    2580
cacagacgcg agattagcct catttggaac ggagatcgcg tctttattga caggtggtgc    2640
aacccaatgt gctcgaaagt caccctcgga accatcaggg ccaggtgcac ctgcggggaa    2700
tgtccccgag tgtgtgagca atgccgcact gatacaggag tggacacccg aatctggtac    2760
cacaatctcc ccgagatccc agaataatga agaaggggga gactattatg atgatgagct    2820
gttctctgat gtccaagata ttaaaacagc cttggccaaa atacacgagg ataatcagaa    2880
gataatctcc aagctagaat cactgctgtt attgaaggga gaagttgagt caattaagaa    2940
gcagatcaac aggcaaaata tcagcatatc caccctggaa ggacacctct caagcatcat    3000
gatcgccatt cctggacttg gaaggatcc caacgacccc actgcagatg tcgaaatcaa    3060
tcccgacttg aaacccatca taggcagaga ttcaggccga gcactggccg aagttctcaa    3120
gaaacccgtt gccagccgac aactccaagg aatgacaaat ggacggacca gttccagagg    3180
acagctgctg aaggaatttc agctaaagcc gatcgggaaa aagatgagct cagccgtcgg    3240
gtttgttcct gacaccggcc ctgcatcacg cagtgtaatc cgctccatta taaaatccag    3300
ccggctagag gaggatcgga agcgttacct gatgactctc cttgatgata tcaaaggagc    3360
caatgatctt gccaagttcc accagatgct gatgaagata taatgaagt agctacagct    3420
caacttacct gccaacccca tgccagtcga cccaactagt acaacctaaa tccattataa    3480
aaaacttagg agcaaagtga ttgcctccca aggtccacaa tgacagagac ctacgacttc    3540
gacaagtcgg catgggacat caaagggtcg atcgctccga tacaacccac cacctacagt    3600
gatggcaggc tggtgcccca ggtcagagtc atagatcctg gtctaggcga caggaaggat    3660
gaatgctta tgtacatgtt tctgctgggg gttgttgagg cagcgattc cctagggcct    3720
ccaatcgggc gagcatttgg gttcctgccc ttaggtgttg gcagatccac agcaaagccc    3780
gaaaactcc tcaaagaggc cactgagctt gacatagttg ttagacgtac agcagggctc    3840
aatgaaaaac tggtgttcta caacaacacc ccactaactc tcctcacacc ttggagaaag    3900
gtcctaacaa cagggagtgt cttcaacgca aaccaagtgt gcaatgcggt taatctgata    3960
ccgctcgata ccccgcagag gttccgtgtt gtttatgatg catcacccg tctttcggat    4020
aacgggtatt acaccgttcc tagaagaatg ctggaattca gatcggtcaa tgcagtggcc    4080
```

```
ttcaacctgc tggtgaccct taggattgac aaggcgatag gccctgggaa gatcatcgac    4140
aatacagagc aacttcctga ggcaacattt atggtccaca tcgggaactt caggagaaag    4200
aagagtgaag tctactctgc cgattattgc aaaatgaaaa tcgaaaagat gggcctggtt    4260
tttgcacttg gtgggatagg gggcaccagt cttcacatta gaagcacagg caaaatgagc    4320
aagactctcc atgcacaact cgggttcaag aagaccttat gttacccgct gatggatatc    4380
aatgaagacc ttaatcgatt actctggagg agcagatgca agatagtaag aatccaggca    4440
gttttgcagc catcagttcc tcaagaattc cgcatttacg acgacgtgat cataaatgat    4500
gaccaaggac tattcaaagt tctgtagacc gtagtgccca gcaatgcccg aaaacgaccc    4560
ccctcacaat gacagccaga aggcccggac aaaaaagccc cctccgaaag actccacgga    4620
ccaagcgaga ggccagccag cagccgacgg caagcgcgaa caccaggcgg ccccagcaca    4680
gaacagccct gacacaaggc caccaccagc cacccccaatc tgcatcctcc tcgtgggacc    4740
cccgaggacc aaccccccaag gctgcccccg atccaaacca ccaaccgcat ccccaccacc    4800
cccgggaaag aaaccccccag caattggaag gcccctcccc ctcttcctca acacaagaac    4860
tccacaaccg aaccgcacaa gcgaccgagg tgacccaacc gcaggcatcc gactccctag    4920
acagatcctc tctccccggc aaactaaaca aaacttaggg ccaaggaaca tacacaccca    4980
acagaaccca gaccccggcc cacggcgccg cgccccaac ccccgacaac cagagggagc    5040
ccccaaccaa tcccgccggc tccccggtg cccacaggca gggacaccaa ccccgaaca    5100 gacccagcac ccaaccatcg acaatccaag acggggggc ccccaaaa aaaggccccc    5160 agggccgac agccagcacc gcgaggaagc ccacccaccc cacacacgac cacggcaacc    5220
aaaccgaaac ccagaccacc ctgggccacc agctcccaga ctcggccatc accccgcaga    5280
aaggaaaggc cacaacccgc gcaccccagc cccgatccgg cggggagcca cccaacccga    5340
accagcaccc aagagcgatc cccgaaggac ccccgaaccg caaaggacat cagtatccca    5400
cagcctctcc aagtcccccg gtctcctcct cttctcgaag ggaccaaaag atcaatccac    5460
cacacccgac gacactcaac tccccacccc taaaggagac accgggaatc ccagaatcaa    5520
gactcatcca atgtccatca tgggtctcaa ggtgaacgtc tctgccatat tcatggcagt    5580
actgttaact ctccaaacac ccaccggtca aatccattgg ggcaatctct ctaagatagg    5640
ggtggtagga ataggaagtg caagctacaa agttatgact cgttccagcc atcaatcatt    5700
agtcataaaa ttaatgccca atataactct cctcaataac tgcacgaggg tagagattgc    5760
agaatacagg agactactga gaacagtttt ggaaccaatt agagatgcac ttaatgcaat    5820
gacccagaat ataagaccgg ttcagagtgt agcttcaagt aggagacaca agagatttgc    5880
gggagtagtc ctggcaggtg cggccctagg cgttgccaca gctgctcaga taacagccgg    5940
cattgcactt caccagtcca tgctgaactc tcaagccatc gacaatctga gagcgagcct    6000
ggaaactact aatcaggcaa ttgagacaat cagacaagca gggcaggaga tgatattggc    6060
tgttcagggt gtccaagact acatcaataa tgagctgata ccgtctatga accaactatc    6120
ttgtgattta atcggccaga agctcgggct caaattgctc agatactata cagaaatcct    6180
gtcattattt ggccccagtt tacgggaccc catatctgcg gagatatcta tccaggcttt    6240
gagctatgcg cttggaggag acatcaataa ggtgttagaa aagctcggat acagtggagg    6300
tgatttactg ggcatcttag agagcggagg aataaaggcc cggataactc acgtcgacac    6360
agagtcctac ttcattgtcc tcagtatagc ctatccgacg ctgtccgaga ttaaggggt    6420
```

```
gattgtccac cggctagagg gggtctcgta caacataggc tctcaagagt ggtataccac    6480
tgtgcccaag tatgttgcaa cccaagggta ccttatctcg aattttgatg agtcatcgtg    6540
tactttcatg ccagagggga ctgtgtgcag ccaaaatgcc ttgtacccga tgagtcctct    6600
gctccaagaa tgcctccggg ggtacaccaa gtcctgtgct cgtacactcg tatccgggtc    6660
ttttgggaac cggttcattt tatcacaagg gaacctaata gccaattgtg catcaatcct    6720
ttgcaagtgt tacacaacag gaacgatcat taatcaagac cctgacaaga tcctaacata    6780
cattgctgcc gatcactgcc cggtagtcga ggtgaacggc gtgaccatcc aagtcgggag    6840
caggaggtat ccagacgctg tgtacttgca cagaattgac ctcggtcctc ccatatcatt    6900
ggagaggttg gacgtaggga caaatctggg gaatgcaatt gctaagttgg aggatgccaa    6960
ggaattgttg gagtcatcgg accagatatt gaggagtatg aaaggtttat cgagcactag    7020
catagtctac atcctgattg cagtgtgtct tggagggttg atagggatcc ccgctttaat    7080
atgttgctgc agggggcgtt gtaacaaaaa gggagaacaa gttggtatgt caagaccagg    7140
cctaaagcct gatcttacgg gaacatcaaa atcctatgta aggtcgctct gatcctctac    7200
aactcttgaa acacaaatgt cccacaagtc tcctcttcgt catcaagcaa ccaccgcacc    7260
cagcatcaag cccacctgaa attatctccg gcttccctct ggccgaacaa tatcggtagt    7320
taatcaaaac ttagggtgca agatcatcca caatgtcacc acaacgagac cggataaatg    7380
ccttctacaa agataacccc catcccaagg gaagtaggat agtcattaac agagaacatc    7440
ttatgattga tagaccttat gttttgctgg ctgttctgtt tgtcatgttt ctgagcttga    7500
tcgggttgct agccattgca ggcattagac ttcatcgggc agccatctac accgcagaga    7560
tccataaaag cctcagcacc aatctagatg taactaactc aatcgagcat caggtcaagg    7620
acgtgctgac accactcttc aaaatcatcg gtgatgaagt gggcctgagg acacctcaga    7680
gattcactga cctagtgaaa ttaatctctg acaagattaa attccttaat ccggataggg    7740
agtacgactt cagagatctc acttggtgta tcaacccgcc agagagaatc aaattggatt    7800
atgatcaata ctgtgcagat gtggctgctg aagagctcat gaatgcattg gtgaactcaa    7860
ctctactgga gaccagaaca accaatcagt tcctagctgt ctcaaaggga aactgctcag    7920
ggcccactac aatcagaggt caattctcaa acatgtcgct gtccctgtta gacttgtatt    7980
taggtcgagg ttacaatgtg tcatctatag tcactatgac atcccaggga atgtatgggg    8040
gaacttacct agtggaaaag cctaatctga gcagcaaaag gtcagagttg tcacaactga    8100
gcatgtaccg agtgtttgaa gtaggtgtta tcagaaatcc gggttttggg gctccggtgt    8160
tccatatgac aaactatctt gagcaaccag tcagtaatga tctcagcaac tgtatggtgg    8220
ctttggggga gctcaaactc gcagcccttt gtcacgggga agattctatc acaattccct    8280
atcagggatc agggaaaggt gtcagcttcc agctcgtcaa gctaggtgtc tggaaatccc    8340
caaccgacat gcaatcctgg gtccccttat caacggatga tccagtgata gacaggcttt    8400
acctctcatc tcacagaggt gttatcgctg acaatcaagc aaaatgggct gtcccgacaa    8460
cacgaacaga tgacaagttg cgaatggaga catgcttcca acaggcgtgt aagggtaaaa    8520
tccaagcact ctgcgagaat cccgagtggg caccattgaa ggataacagg attccttcat    8580
acggggtctt gtctgttgat ctgagtctga cagttgagct taaaatcaaa attgcttcgg    8640
gattcgggcc attgatcaca cacggttcag ggatggacct atacaaatcc aaccacaaca    8700
atgtgtattg gctgactatc ccgccaatga agaacctagc cttaggtgta atcaacacat    8760
tggagtggat accgagattc aaggttagtc cctacctctt cactgtccca attaaggaag    8820
```

```
caggcgaaga ctgccatgcc ccaacatacc tacctgcgga ggtggatggt gatgtcaaac    8880
tcagttccaa tctggtgatt ctacctggtc aagatctcca atatgttttg gcaacctacg    8940
atacttccag ggttgaacat gctgtggttt attacgttta cagcccaagc cgctcatttt    9000 cttacttttta tccttttagg ttgcctataa aggggggtccc catcgaatta caagtggaat    9060
gcttcacatg ggaccaaaaa ctctggtgcc gtcacttctg tgtgcttgcg gactcagaat    9120
ctggtggaca tatcactcac tctgggatgg tgggcatggg agtcagctgc acagtcaccc    9180
gggaagatgg aaccaatcgc atagggct gctagtgaac caatcacatg atgtcaccca    9240
gacatcaggc atacccacta gtgtgaaata gacatcagaa ttaagaaaaa cgtagggtcc    9300
aagtggttcc ccgttatgga ctcgctatct gtcaaccaga tcttataccc tgaagttcac    9360
ctagatagcc cgatagttac caataagata gtagccatcc tggagtatgc tcgagtccct    9420
cacgcttaca gcctggagga ccctacactg tgtcagaaca tcaagcaccg cctaaaaaac    9480
ggattttcca accaaatgat tataaacaat gtggaagttg gaatgtcat caagtccaag    9540 cttaggagtt atccggccca ctctcatatt ccatatccaa attgtaatca ggatttatttt   9600 aacatagaag acaaagagtc aacgaggaag atccgtgaac tcctcaaaaa ggggaattcg    9660
ctgtactcca aagtcagtga taaggttttc caatgcttaa gggacactaa ctcacggctt    9720
ggcctaggct ccgaattgag ggaggacatc aaggagaaag ttattaactt gggagtttac    9780
atgcacagct cccagtggtt tgagcccttt ctgttttggt ttacagtcaa gactgagatg    9840
aggtcagtga ttaaatcaca aacccatact tgccatagga ggagacacac acctgtattc    9900
ttcactggta gttcagttga gttgctaatc tctcgtgacc ttgttgctat aatcagtaaa    9960
gagtctcaac atgtatatta cctgacattt gaactggttt tgatgtattg tgatgtcata   10020
gaggggaggt taatgacaga daccgctatg actattgatg ctaggtatac agagcttcta   10080
ggaagagtca gatacatgtg gaaactgata gatggtttct tccctgcact cgggaatcca   10140
acttatcaaa ttgtagccat gctggagcct cttccacttg cttacctgca gctgagggat   10200
ataacagtag aactcagagg tgctttcctt aaccactgct ttactgaaat acatgatgtt   10260
cttgaccaaa acgggttttc tgatgaaggt acttatcatg agttaactga agctctagat   10320 tacatttttca taactgatga catacatctg acaggggaga ttttctcatt tttcagaagt   10380
ttcggccacc ccagacttga agcagtaacg gctgctgaaa atgttaggaa atacatgaat   10440
cagcctaaag tcattgtgta tgagactctg atgaaaggtc atgccatatt ttgtggaatc   10500
ataatcaacg gctatcgtga caggcacgga ggcagttggc caccgctgac cctcccctg    10560 catgctgcag acacaatccg gaatgctcaa gcttcaggtg aagggttaac acatgagcag   10620
tgcgttgata actggaaatc ttttgctgga gtgaaatttg gctgctttat gcctcttagc   10680
ctggatagtg atctgacaat gtacctaaag gacaaggcac ttgctgctct ccaaagggaa   10740
tgggattcag tttacccgaa agagttcctg cgttacgacc ctcccaaggg aaccgggtca   10800
cggaggcttg tagatgtttt cttaatgat tcgagctttg acccatatga tgtgataatg   10860
tatgttgtaa gtggagctta cctccatgac cctgagttca acctgtctta cagcctgaaa   10920
gaaaaggaga tcaaggaaac aggtagactt tttgctaaaa tgacttacaa aatgagggca   10980
tgccaagtga ttgctgaaaa tctaatctca aacgggattg gcaaatattt taaggacaat   11040
gggatggcca aggatgagca cgatttgact aaggcactcc acactctagc tgtctcagga   11100
gtccccaaag atctcaaaga aagtcacagg gggggccag tcttaaaaac ctactcccga   11160
```

```
agcccagtcc acacaagtac caggaacgtg agagcagcaa aagggtttat agggttccct   11220
caagtaattc ggcaggacca agacactgat catccggaga atatggaagc ttacgagaca   11280
gtcagtgcat ttatcacgac tgatctcaag aagtactgcc ttaattggag atatgagacc   11340
atcagcttgt ttgcacagag gctaaatgag atttacggat tgccctcatt tttccagtgg   11400
ctgcataaga ggcttgagac ctctgtcctg tatgtaagtg accctcattg ccccccccgac   11460 cttgacgccc atatcccgtt atataaagtc cccaatgatc aaatcttcat taagtaccct   11520
atgggaggta tagaagggta ttgtcagaag ctgtggacca tcagcaccat tccctatcta   11580
tacctggctg cttatgagag cggagtaagg attgcttcgt tagtgcaagg ggacaatcag   11640
accatagccg taacaaaaag ggtacccagc acatggccct acaaccttaa gaaacgggaa   11700
gctgctagag taactagaga ttactttgta attcttaggc aaaggctaca tgatattggc   11760
catcacctca aggcaaatga gacaattgtt tcatcacatt ttttgtcta ttcaaaagga   11820 atatattatg atgggctact tgtgtcccaa tcactcaaga gcatcgcaag atgtgtattc   11880
tggtcagaga ctatagttga tgaaacaagg gcagcatgca gtaatattgc tacaacaatg   11940
gctaaaagca tcgagagagg ttatgaccgt taccttgcat attccctgaa cgtcctaaaa   12000
gtgatacagc aaattctgat ctctcttggc ttcacaatca attcaaccat gacccgggat   12060
gtagtcatac ccctcctcac aaacaacgac ctcttaataa ggatggcact gttgcccgct   12120
cctattgggg ggatgaatta tctgaatatg agcaggctgt ttgtcagaaa catcggtgat   12180
ccagtaacat catcaattgc tgatctcaag agaatgattc tcgcctcact aatgcctgaa   12240
gagaccctcc atcaagtaat gacacaacaa ccggggact cttcattcct agactgggct   12300 agcgacccctt actcagcaaa tcttgtatgt gtccagagca tcactagact cctcaagaac   12360
ataactgcaa ggtttgtcct gatccatagt ccaaacccaa tgttaaaagg attattccat   12420
gatgacagta agaagagga cgagggactg gcggcattcc tcatggacag gcatattata   12480
gtacctaggg cagctcatga aatcctggat catagtgtca caggggcaag agagtctatt   12540
gcaggcatgc tggataccac aaaaggcttg attcgagcca gcatgaggaa ggggggggtta   12600 acctctcgag tgataaccag attgtccaat tatgactatg aacaattcag agcagggatg   12660
gtgctattga caggaagaaa gagaaatgtc ctcattgaca aagagtcatg ttcagtgcag   12720
ctggcgagag ctctaagaag ccatatgtgg gcgaggctag ctcgaggacg gcctatttac   12780
ggccttgagg tccctgatgt actagaatct atgcgaggcc accttattcg gcgtcatgag   12840
acatgtgtca tctgcgagtg tggatcagtc aactacggat ggttttttgt cccctcgggt   12900
tgccaactgg atgatattga caaggaaaca tcatccttga gagtcccata tattggttct   12960
accactgatg agagaacaga catgaagctt gccttcgtaa gagccccaag tcgatccttg   13020
cgatctgctg ttagaatagc aacagtgtac tcatgggctt acggtgatga tgatagctct   13080
tggaacgaag cctggttgtt ggctaggcaa agggccaatg tgagcctgga ggagctaagg   13140
gtgatcactc ccatctcaac ttcgactaat ttagcgcata ggttgaggga tcgtagcact   13200
caagtgaaat actcaggtac atcccttgtc cgagtggcga ggtataccac aatctccaac   13260
gacaatctct catttgtcat atcagataag aaggttgata ctaactttat ataccaacaa   13320
ggaatgcttc tagggttggg tgttttagaa acattgtttc gactcgagaa agataccgga   13380
tcatctaaca cggtattaca tcttcacgtc gaaacagatt gttgcgtgat cccgatgata   13440
gatcatccca ggatacccag ctcccgcaag ctagagctga gggcagagct atgtaccaac   13500
ccattgatat atgataatgc acctttaatt gacagagatg caacaaggct atacacccag   13560
```

```
agccatagga ggcaccttgt ggaatttgtt acatggtcca caccccaact atatcacatt    13620
ttagctaagt ccacagcact atctatgatt gacctggtaa caaaatttga gaaggaccat    13680
atgaatgaaa tttcagctct catagggggat gacgatatca atagtttcat aactgagttt    13740
ctgctcatag agccaagatt attcactatc tacttgggcc agtgtgcggc catcaattgg    13800
gcatttgatg tacattatca tagaccatca gggaaatatc agatgggtga gctgttgtca    13860
tcgttccttt ctagaatgag caaaggagtg tttaaggtgc ttgtcaatgc tctaagccac    13920
ccaaagatct acaagaaatt ctggcattgt ggtattatag agcctatcca tggtccttca    13980
cttgatgctc aaaacttgca cacaactgtg tgcaacatgg tttacacatg ctatatgacc    14040
tacctcgacc tgttgttgaa tgaagagtta aagagttca catttctctt gtgtgaaagc    14100
gacgaggatg tagtaccgga cagattcgac aacatccagg caaaacactt atgtgttctg    14160
gcagatttgt actgtcaacc agggacctgc ccaccaattc gaggtctaag accggtagag    14220
aaatgtgcag ttctaaccga ccatatcaag gcagaggcta tgttatctcc agcaggatct    14280
tcgtggaaca taaatccaat tattgtagac cattactcat gctctctgac ttatctccgg    14340
cgaggatcga tcaaacagat aagattgaga gttgatccag gattcatttt cgacgccctc    14400
gctgaggtaa atgtcagtca gccaaagatc ggcagcaaca acatctcaaa tatgagcatc    14460
aaggctttca gaccccccaca cgatgatgtt gcaaaattgc tcaaagatat caacacaagc    14520
aagcacaatc ttcccatttc aggggggcaat ctcgccaatt atgaaatcca tgctttccgc    14580
agaatcgggt tgaactcatc tgcttgctac aaagctgttg agatatcaac attaattagg    14640
agatgccttg agccagggga ggacggcttg ttcttgggtg agggatcggg ttctatgttg    14700
atcacttata aagagatact taaactaaac aagtgcttct ataatagtgg ggtttccgcc    14760
aattctagat ctggtcaaag ggaattagca ccctatccct ccgaagttgg ccttgtcgaa    14820
cacagaatgg gagtaggtaa tattgtcaaa gtgctcttta cgggaggcc cgaagtcacg    14880 tgggtaggca gtgtagattg cttcaatttc atagttagta atatccctac ctctagtgtg    14940
gggtttatcc attcagatat agagaccttg cctgacaaag atactataga gaagctagag    15000
gaattggcag ccatcttatc gatggctctg ctcctgggca aaataggatc aatactggtg    15060
attaagctta tgcctttcag cggggatttt gttcagggat ttataagtta tgtagggtct    15120
cattatagag aagtgaacct tgtatacccct agatacagca acttcatctc tactgaatct    15180
tatttggtta tgacagatct caaggctaac cggctaatga atcctgaaaa gattaagcag    15240
cagataattg aatcatctgt gaggacttca cctggactta taggtcacat cctatccatt    15300
aagcaactaa gctgcataca agcaattgtg ggagacgcag ttagtagagg tgatatcaat    15360
cctactctga aaaacttac acctatagag caggtgctga tcaattgcgg gttggcaatt    15420
aacggaccta gctgtgcaa agaattgatc caccatgatg ttgcctcagg gcaagatgga    15480
ttgcttaatt ctatactcat cctctacagg gagttggcaa gattcaaaga caaccaaaga    15540
agtcaacaag ggatgttcca cgcttacccc gtattggtaa gtagcaggca acgagaactt    15600
atatctagga tcacccgcaa attctggggg cacattcttc tttactccgg gaacaaaaag    15660
ttgataaata agttatcca gaatctcaag tccggctatc tgatactaga cttacaccag    15720
aatatcttcg ttaagaatct atccaagtca gagaaacaga ttattatgac gggggggtttg    15780 aaacgtgagt gggttttaa ggtaacagtc aaggagacca agaatggta taagttagtc    15840 ggatacagtg ccctgattaa ggactaattg gttgaactcc ggaaccctaa tcctgcccta    15900
```

-continued

```
ggtggttagg cattatttgc aatatattaa agaaaacttt gaaaatacga agtttctatt    15960
cccagctttg tctggtggcc ggcatggtcc cagcctcctc gctggcgccg gctgggcaac    16020
attccgaggg gaccgtcccc tcggtaatgg cgaatgggac gcggccgatc cggctgctaa    16080
caaagcccga aggaagctg  agttggctgc tgccaccgct gagcaataac tagcataacc    16140
ccttggggcc tctaaacggg tcttgagggg ttttttgctg aaaggaggaa ctatatccgg    16200
atgcggccgc gggccctatg gtacccagct tttgttccct ttagtgaggg ttaattccga    16260
gcttggcgta atcatggtca tagctgtttc ctgtgtgaaa ttgttatccg ctcacaattc    16320
cacacaacat aggagccgga agcataaagt gtaaagcctg gggtgcctaa tgagtgaggt    16380
aactcacatt aattgcgttg cgctcactgc ccgctttcca gtcgggaaac ctgtcgtgcc    16440
agctgcatta atgaatcggc caacgcgcgg ggagaggcgg tttgcgtatt gggcgctctt    16500
ccgcttcctc gctcactgac tcgctgcgct cggtcgttcg gctgcggcga gcggtatcag    16560
ctcactcaaa ggcggtaata cggttatcca cagaatcagg ggataacgca ggaaagaaca    16620
tgtgagcaaa aggccagcaa aaggccagga accgtaaaaa ggccgcgttg ctggcgtttt    16680
tccataggct cggcccccct gacgagcatc acaaaaatcg acgctcaagt cagaggtggc    16740
gaaacccgac aggactataa agataccagg cgttcccccc tggaagctcc ctcgtgcgct    16800
ctcctgttcc gaccctgccg cttaccggat acctgtccgc ctttctccct tcgggaagcg    16860
tggcgctttc tcaatgctca cgctgtaggt atctcagttc ggtgtaggtc gttcgctcca    16920
agctgggctg tgtgcacgaa ccccccgttc agcccgaccg ctgcgcctta tccggtaact    16980
atcgtcttga gtccaacccg gtaagacacg acttatcgcc actggcagca gccactggta    17040
acaggattag cagagcgagg tatgtaggcg gtgctacaga gttcttgaag tggtggccta    17100
actacggcta cactagaagg acagtatttg gtatctgcgc tctgctgaag ccagttacct    17160
tcggaaaaag agttggtagc tcttgatccg gcaaacaaac caccgctggt agcggtggtt    17220
tttttgtttg caagcagcag attacgcgca gaaaaaaagg atctcaagaa gatcctttga    17280
tcttttctac ggggtctgac gctcagtgga acgaaaactc acgttaaggg attttggtca    17340
tgagattatc aaaaaggatc ttcacctaga tccttttaaa ttaaaaatga agttttaaat    17400
caatctaaag tatatatgag taaacttggt ctgacagtta ccaatgctta atcagtgagg    17460
cacctatctc agcgatctgt ctatttcgtt catccatagt tgcctgactg cccgtcgtgt    17520
agataactac gatacgggag ggcttaccat ctggccccag tgctgcaatg ataccgcgag    17580
acccacgctc accggctcca gatttatcag caataaacca gccagccgga agggccgagc    17640
gcagaagtgg tcctgcaact ttatccgcct ccatccagtc tattaattgt tgccgggaag    17700
ctagagtaag tagttcgcca gttaatagtt tgcgcaacgt tgttgccatt gctacaggca    17760
tcgtggtgtc acgctcgtcg tttggtatgg cttcattcag ctccggttcc caacgatcaa    17820
ggcgagttac atgatccccc atgttgtgaa aaaagcggt  tagctccttc ggtcctccga    17880
tcgttgtcag aagtaagttg gccgcagtgt tatcactcat gcttatggca gcactgcata    17940
attctcttac tgtcatgcca tccgtaagat gcttttctgt gactggtgag tactcaacca    18000
agtcattctg agaatagtgt atgcggcgac cgagttgctc ttgcccggcg tcaatacggg    18060
ataataccgc gccacatagc agaactttaa aagtgctcat cattggaaaa cgttcttcgg    18120
ggcgaaaact ctcaaggatc ttaccgctgt tgagatccag ttcgatgtaa cccactcgtg    18180
cacccaactg atcttcagca tcttttactt tcaccagcgt ttctgggtga gcaaaaacag    18240
gaaggcaaaa tgccgcaaaa aagggaataa gggcgacacg gaaatgttga atactcatac    18300
```

-continued

```
tcttccttttt tcaatattat tgaagcattt atcagggtta ttgtctcatg agcggataca    18360
tatttgaatg tatttagaaa aataaacaaa tagggggttcc gcgcacattt ccccgaaaag    18420
tgccacctga aattgtaaac gttaatattt tgttaaaatt cgcgttaaat ttttgttaaa    18480
tcagctcatt ttttaaccaa taggccgaaa tcggcaaaat cccttataaa tcaaaagaat    18540
agaccgagat agggttgagt gttgttccag tttggaacaa gagtccacta ttaaagaacg    18600
tggactccaa cgtcaaaggg cgaaaaaccg tctatcaggg cgatggccca ctacgtgaac    18660
catcacccta atcaagtttt tgggggtcga ggtgccgtaa agcactaaat cggaacccta    18720
aagggagccc ccgatttaga gcttgacggg gaaagccggc gaacgtggcg agaaaggaag    18780
ggaagaaagc gaaaggagcg ggcgctaggg cgctggcaag tgtagcggtc acgctgcgcg    18840
taaccaccac acccgccgcg cttaatgcgc cgctacaggg cgcgtcccat tcgccattca    18900
ggctgcgcaa ctgttgggaa gggcgatcgg tgcgggcctc ttcgctatta cgccagccac    18960
cgcggtg                                                               18967

<210> SEQ ID NO 2
<211> LENGTH: 1797
<212> TYPE: DNA
<213> ORGANISM: Chikungunya virus
<220> FEATURE:
<221> NAME/KEY: misc_feature
<223> OTHER INFORMATION: soluble glycoprotein E2 strain 05.115
<220> FEATURE:
<221> NAME/KEY: CDS
<222> LOCATION: (1)..(1797)

<400> SEQUENCE: 2 ata ccc gtg cac atg aag tcc gac gct tcg aag ttc acc cat gag aaa        48
Ile Pro Val His Met Lys Ser Asp Ala Ser Lys Phe Thr His Glu Lys
1               5                   10                  15 ccg gag ggg tac tac aac tgg cac cac gga gca gta cag tac tca gga        96
Pro Glu Gly Tyr Tyr Asn Trp His His Gly Ala Val Gln Tyr Ser Gly
            20                  25                  30 ggc cgg ttc acc atc cct aca ggt gct ggc aaa cca ggg gac agc ggc       144
Gly Arg Phe Thr Ile Pro Thr Gly Ala Gly Lys Pro Gly Asp Ser Gly
        35                  40                  45 aga ccg atc ttc gac aac aag gga cgc gtg gtg gcc ata gtc tta gga       192
Arg Pro Ile Phe Asp Asn Lys Gly Arg Val Val Ala Ile Val Leu Gly
    50                  55                  60 gga gct aat gaa gga gcc cgt aca gcc ctc tcg gtg gtg acc tgg aat       240
Gly Ala Asn Glu Gly Ala Arg Thr Ala Leu Ser Val Val Thr Trp Asn
65                  70                  75                  80 aaa gac att gtc act aaa atc acc ccc gag ggg gcc gaa gag tgg agt       288
Lys Asp Ile Val Thr Lys Ile Thr Pro Glu Gly Ala Glu Glu Trp Ser
                85                  90                  95 ctt gcc atc cca gtt atg tgc ctg ttg gca aac acc acg ttc ccc tgc       336
Leu Ala Ile Pro Val Met Cys Leu Leu Ala Asn Thr Thr Phe Pro Cys
            100                 105                 110 tcc cag ccc cct tgc acg ccc tgc tgc tac gaa aag gaa ccg gag gaa       384
Ser Gln Pro Pro Cys Thr Pro Cys Cys Tyr Glu Lys Glu Pro Glu Glu
        115                 120                 125 acc cta cgc atg ctt gag gac aac gtc atg aga cct ggg tac tat cag       432
Thr Leu Arg Met Leu Glu Asp Asn Val Met Arg Pro Gly Tyr Tyr Gln
    130                 135                 140 ctg cta caa gca tcc tta aca tgt tct ccc cac cgc cag cga cgc agc       480
Leu Leu Gln Ala Ser Leu Thr Cys Ser Pro His Arg Gln Arg Arg Ser
145                 150                 155                 160
```

```
acc aag gac aac ttc aat gtc tat aaa gcc aca aga cca tac tta gct    528
Thr Lys Asp Asn Phe Asn Val Tyr Lys Ala Thr Arg Pro Tyr Leu Ala
                165                 170                 175 cac tgt ccc gac tgt gga gaa ggg cac tcg tgc cat agt ccc gta gca    576
His Cys Pro Asp Cys Gly Glu Gly His Ser Cys His Ser Pro Val Ala
            180                 185                 190 cta gaa cgc atc aga aat gaa gcg aca gac ggg acg ctg aaa atc cag    624
Leu Glu Arg Ile Arg Asn Glu Ala Thr Asp Gly Thr Leu Lys Ile Gln
        195                 200                 205 gtc tcc ttg caa atc gga ata aag acg gat gac agc cac gat tgg acc    672
Val Ser Leu Gln Ile Gly Ile Lys Thr Asp Asp Ser His Asp Trp Thr
    210                 215                 220 aag ctg cgt tat atg gac aac cac atg cca gca gac gca gag agg gcg    720
Lys Leu Arg Tyr Met Asp Asn His Met Pro Ala Asp Ala Glu Arg Ala
225                 230                 235                 240 ggg cta ttt gta aga aca tca gca ccg tgt acg att act gga aca atg    768
Gly Leu Phe Val Arg Thr Ser Ala Pro Cys Thr Ile Thr Gly Thr Met
                245                 250                 255 gga cac ttc atc ctg gcc cga tgt cca aaa ggg gaa act ctg acg gtg    816
Gly His Phe Ile Leu Ala Arg Cys Pro Lys Gly Glu Thr Leu Thr Val
            260                 265                 270 gga ttc act gac agt agg aag att agt cac tca tgt acg cac cca ttt    864
Gly Phe Thr Asp Ser Arg Lys Ile Ser His Ser Cys Thr His Pro Phe
        275                 280                 285 cac cac gac cct cct gtg ata ggt cgg gaa aaa ttc cat tcc cga ccg    912
His His Asp Pro Pro Val Ile Gly Arg Glu Lys Phe His Ser Arg Pro
    290                 295                 300 cag cac ggt aaa gag ata cct tgc agc acg tac gtg cag agc acc gcc    960
Gln His Gly Lys Glu Ile Pro Cys Ser Thr Tyr Val Gln Ser Thr Ala
305                 310                 315                 320 gca act acc gag gag ata gag gta cac atg ccc cca gac acc cct gat   1008
Ala Thr Thr Glu Glu Ile Glu Val His Met Pro Pro Asp Thr Pro Asp
                325                 330                 335 cgc aca tta atg tca caa cag tcc ggc aac gta aag atc aca gtc aat   1056
Arg Thr Leu Met Ser Gln Gln Ser Gly Asn Val Lys Ile Thr Val Asn
            340                 345                 350 ggc cag acg gtg cgg tac aag tgt aat tgc ggt ggc tca aat gaa gga   1104
Gly Gln Thr Val Arg Tyr Lys Cys Asn Cys Gly Gly Ser Asn Glu Gly
        355                 360                 365 cta aca act aca gac aaa gtg att aat aac tgc aag gtt gat caa tgt   1152
Leu Thr Thr Thr Asp Lys Val Ile Asn Asn Cys Lys Val Asp Gln Cys
    370                 375                 380 cat gcc gcg gtc acc aat cac aaa aag tgg cag tat aac tcc cct ctg   1200
His Ala Ala Val Thr Asn His Lys Lys Trp Gln Tyr Asn Ser Pro Leu
385                 390                 395                 400 gtc ccg cgt aat gct gaa ctt ggg gac cga aaa gga aaa att cac atc   1248
Val Pro Arg Asn Ala Glu Leu Gly Asp Arg Lys Gly Lys Ile His Ile
                405                 410                 415 ccg ttt ccg ctg gca aat gta aca tgc agg gtg cct aaa gca agg aac   1296
Pro Phe Pro Leu Ala Asn Val Thr Cys Arg Val Pro Lys Ala Arg Asn
            420                 425                 430 ccc acc gtg acg tac ggg aaa aac caa gtc atc atg cta ctg tat cct   1344
Pro Thr Val Thr Tyr Gly Lys Asn Gln Val Ile Met Leu Leu Tyr Pro
        435                 440                 445 gac cac cca aca ctc ctg tcc tac cgg aat atg gga gaa gaa cca aac   1392
Asp His Pro Thr Leu Leu Ser Tyr Arg Asn Met Gly Glu Glu Pro Asn
    450                 455                 460 tat caa gaa gag tgg gtg atg cat aag aag gaa gtc gtg cta acc gtg   1440
Tyr Gln Glu Glu Trp Val Met His Lys Lys Glu Val Val Leu Thr Val
465                 470                 475                 480
```

```
ccg act gaa ggg ctc gag gtc acg tgg ggc aac aac gag ccg tat aag      1488
Pro Thr Glu Gly Leu Glu Val Thr Trp Gly Asn Asn Glu Pro Tyr Lys
                485                 490                 495 tat tgg ccg cag tta tct aca aac ggt aca gcc cat ggc cac ccg cat      1536
Tyr Trp Pro Gln Leu Ser Thr Asn Gly Thr Ala His Gly His Pro His
            500                 505                 510 gag ata att ctg tat tat tat gag ctg tac ccc act atg act gta gta      1584
Glu Ile Ile Leu Tyr Tyr Tyr Glu Leu Tyr Pro Thr Met Thr Val Val
        515                 520                 525 gtt gtg tca gtg gcc acg ttc ata ctc ctg tcg atg gtg ggt atg gca      1632
Val Val Ser Val Ala Thr Phe Ile Leu Leu Ser Met Val Gly Met Ala
    530                 535                 540 gcg ggg atg tgc atg tgt gca cga cgc aga tgc atc aca ccg tat gaa      1680
Ala Gly Met Cys Met Cys Ala Arg Arg Arg Cys Ile Thr Pro Tyr Glu
545                 550                 555                 560 ctg aca cca gga gct acc gtc cct ttc ctg ctt agc cta ata tgc tgc      1728
Leu Thr Pro Gly Ala Thr Val Pro Phe Leu Leu Ser Leu Ile Cys Cys
                565                 570                 575 atc aga aca gct aaa gcg gcc aca tac caa gag gct gcg ata tac ctg      1776
Ile Arg Thr Ala Lys Ala Ala Thr Tyr Gln Glu Ala Ala Ile Tyr Leu
            580                 585                 590 tgg aac gag cag caa cct tta                                          1797
Trp Asn Glu Gln Gln Pro Leu
        595

<210> SEQ ID NO 3
<211> LENGTH: 599
<212> TYPE: PRT
<213> ORGANISM: Chikungunya virus

<400> SEQUENCE: 3

Ile Pro Val His Met Lys Ser Asp Ala Ser Lys Phe Thr His Glu Lys
1               5                   10                  15

Pro Glu Gly Tyr Tyr Asn Trp His His Gly Ala Val Gln Tyr Ser Gly
            20                  25                  30

Gly Arg Phe Thr Ile Pro Thr Gly Ala Gly Lys Pro Gly Asp Ser Gly
        35                  40                  45

Arg Pro Ile Phe Asp Asn Lys Gly Arg Val Val Ala Ile Val Leu Gly
    50                  55                  60

Gly Ala Asn Glu Gly Ala Arg Thr Ala Leu Ser Val Val Thr Trp Asn
65                  70                  75                  80

Lys Asp Ile Val Thr Lys Ile Thr Pro Glu Gly Ala Glu Glu Trp Ser
                85                  90                  95

Leu Ala Ile Pro Val Met Cys Leu Leu Ala Asn Thr Thr Phe Pro Cys
            100                 105                 110

Ser Gln Pro Pro Cys Thr Pro Cys Cys Tyr Glu Lys Glu Pro Glu Glu
        115                 120                 125

Thr Leu Arg Met Leu Glu Asp Asn Val Met Arg Pro Gly Tyr Tyr Gln
    130                 135                 140

Leu Leu Gln Ala Ser Leu Thr Cys Ser Pro His Arg Gln Arg Arg Ser
145                 150                 155                 160

Thr Lys Asp Asn Phe Asn Val Tyr Lys Ala Thr Arg Pro Tyr Leu Ala
                165                 170                 175

His Cys Pro Asp Cys Gly Glu Gly His Ser Cys His Ser Pro Val Ala
            180                 185                 190

Leu Glu Arg Ile Arg Asn Glu Ala Thr Asp Gly Thr Leu Lys Ile Gln
        195                 200                 205
```

Val Ser Leu Gln Ile Gly Ile Lys Thr Asp Asp Ser His Asp Trp Thr
210                 215                 220

Lys Leu Arg Tyr Met Asp Asn His Met Pro Ala Asp Ala Glu Arg Ala
225                 230                 235                 240

Gly Leu Phe Val Arg Thr Ser Ala Pro Cys Thr Ile Thr Gly Thr Met
            245                 250                 255

Gly His Phe Ile Leu Ala Arg Cys Pro Lys Gly Glu Thr Leu Thr Val
            260                 265                 270

Gly Phe Thr Asp Ser Arg Lys Ile Ser His Ser Cys Thr His Pro Phe
            275                 280                 285

His His Asp Pro Pro Val Ile Gly Arg Glu Lys Phe His Ser Arg Pro
290                 295                 300

Gln His Gly Lys Glu Ile Pro Cys Ser Thr Tyr Val Gln Ser Thr Ala
305                 310                 315                 320

Ala Thr Thr Glu Glu Ile Glu Val His Met Pro Pro Asp Thr Pro Asp
                325                 330                 335

Arg Thr Leu Met Ser Gln Gln Ser Gly Asn Val Lys Ile Thr Val Asn
                340                 345                 350

Gly Gln Thr Val Arg Tyr Lys Cys Asn Cys Gly Gly Ser Asn Glu Gly
            355                 360                 365

Leu Thr Thr Thr Asp Lys Val Ile Asn Cys Lys Val Asp Gln Cys
370                 375                 380

His Ala Ala Val Thr Asn His Lys Lys Trp Gln Tyr Asn Ser Pro Leu
385                 390                 395                 400

Val Pro Arg Asn Ala Glu Leu Gly Asp Arg Lys Gly Lys Ile His Ile
                405                 410                 415

Pro Phe Pro Leu Ala Asn Val Thr Cys Arg Val Pro Lys Ala Arg Asn
            420                 425                 430

Pro Thr Val Thr Tyr Gly Lys Asn Gln Val Ile Met Leu Leu Tyr Pro
            435                 440                 445

Asp His Pro Thr Leu Leu Ser Tyr Arg Asn Met Gly Glu Glu Pro Asn
450                 455                 460

Tyr Gln Glu Glu Trp Val Met His Lys Lys Glu Val Val Leu Thr Val
465                 470                 475                 480

Pro Thr Glu Gly Leu Glu Val Thr Trp Gly Asn Asn Glu Pro Tyr Lys
            485                 490                 495

Tyr Trp Pro Gln Leu Ser Thr Asn Gly Thr Ala His Gly His Pro His
            500                 505                 510

Glu Ile Ile Leu Tyr Tyr Tyr Glu Leu Tyr Pro Thr Met Thr Val Val
            515                 520                 525

Val Val Ser Val Ala Thr Phe Ile Leu Leu Ser Met Val Gly Met Ala
530                 535                 540

Ala Gly Met Cys Met Cys Ala Arg Arg Cys Ile Thr Pro Tyr Glu
545                 550                 555                 560

Leu Thr Pro Gly Ala Thr Val Pro Phe Leu Leu Ser Leu Ile Cys Cys
            565                 570                 575

Ile Arg Thr Ala Lys Ala Ala Thr Tyr Gln Glu Ala Ala Ile Tyr Leu
            580                 585                 590

Trp Asn Glu Gln Gln Pro Leu
            595

<210> SEQ ID NO 4
<211> LENGTH: 1797

```
<212> TYPE: DNA
<213> ORGANISM: Chikungunya virus
<220> FEATURE:
<221> NAME/KEY: misc_feature
<223> OTHER INFORMATION: soluble glycoprotein E2 strain 06.21
<220> FEATURE:
<221> NAME/KEY: CDS
<222> LOCATION: (1)..(1797)

<400> SEQUENCE: 4
```

| | | | | | | | | | | | | | | | | |
|---|---|---|---|---|---|---|---|---|---|---|---|---|---|---|---|---|
| ata | ccc | gtg | cac | atg | aag | tcc | gac | gct | tcg | aag | ttc | acc | cat | gag | aaa | 48 |
| Ile | Pro | Val | His | Met | Lys | Ser | Asp | Ala | Ser | Lys | Phe | Thr | His | Glu | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ccg | gag | ggg | tac | tac | aac | tgg | cac | cac | gga | gca | gta | cag | tac | tca | gga | 96 |
| Pro | Glu | Gly | Tyr | Tyr | Asn | Trp | His | His | Gly | Ala | Val | Gln | Tyr | Ser | Gly | |
| | | 20 | | | | | 25 | | | | | 30 | | | | |

| | | | | | | | | | | | | | | | | |
|---|---|---|---|---|---|---|---|---|---|---|---|---|---|---|---|---|
| ggc | cgg | ttc | acc | atc | cct | aca | ggt | gct | ggc | aaa | cca | ggg | gac | agc | ggc | 144 |
| Gly | Arg | Phe | Thr | Ile | Pro | Thr | Gly | Ala | Gly | Lys | Pro | Gly | Asp | Ser | Gly | |
| | | 35 | | | | | 40 | | | | | 45 | | | | |

| | | | | | | | | | | | | | | | | |
|---|---|---|---|---|---|---|---|---|---|---|---|---|---|---|---|---|
| aga | ccg | atc | ttc | gac | aac | aag | gga | cgc | gtg | gtg | gcc | ata | gtc | tta | gga | 192 |
| Arg | Pro | Ile | Phe | Asp | Asn | Lys | Gly | Arg | Val | Val | Ala | Ile | Val | Leu | Gly | |
| | 50 | | | | | 55 | | | | | 60 | | | | | |

| | | | | | | | | | | | | | | | | |
|---|---|---|---|---|---|---|---|---|---|---|---|---|---|---|---|---|
| gga | gct | aat | gaa | gga | gcc | cgt | aca | gcc | ctc | tcg | gtg | gtg | acc | tgg | aat | 240 |
| Gly | Ala | Asn | Glu | Gly | Ala | Arg | Thr | Ala | Leu | Ser | Val | Val | Thr | Trp | Asn | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aaa | gac | att | gtc | act | aaa | atc | acc | ccc | gag | ggg | gcc | gaa | gag | tgg | agt | 288 |
| Lys | Asp | Ile | Val | Thr | Lys | Ile | Thr | Pro | Glu | Gly | Ala | Glu | Glu | Trp | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| ctt | gcc | atc | cca | gtt | atg | tgc | ctg | ttg | gca | aac | acc | acg | ttc | ccc | tgc | 336 |
| Leu | Ala | Ile | Pro | Val | Met | Cys | Leu | Leu | Ala | Asn | Thr | Thr | Phe | Pro | Cys | |
| | | | 100 | | | | | 105 | | | | | 110 | | | |

| | | | | | | | | | | | | | | | | |
|---|---|---|---|---|---|---|---|---|---|---|---|---|---|---|---|---|
| tcc | cag | ccc | cct | tgc | acg | ccc | tgc | tgc | tac | gaa | aag | gaa | ccg | gag | gaa | 384 |
| Ser | Gln | Pro | Pro | Cys | Thr | Pro | Cys | Cys | Tyr | Glu | Lys | Glu | Pro | Glu | Glu | |
| | | | 115 | | | | | 120 | | | | | 125 | | | |

| | | | | | | | | | | | | | | | | |
|---|---|---|---|---|---|---|---|---|---|---|---|---|---|---|---|---|
| acc | cta | cgc | atg | ctt | gag | gac | aac | gtc | atg | aga | cct | ggg | tac | tat | cag | 432 |
| Thr | Leu | Arg | Met | Leu | Glu | Asp | Asn | Val | Met | Arg | Pro | Gly | Tyr | Tyr | Gln | |
| | 130 | | | | | 135 | | | | | 140 | | | | | |

| | | | | | | | | | | | | | | | | |
|---|---|---|---|---|---|---|---|---|---|---|---|---|---|---|---|---|
| ctg | cta | caa | gca | tcc | tta | aca | tgt | tct | ccc | cac | cgc | cag | cga | cgc | agc | 480 |
| Leu | Leu | Gln | Ala | Ser | Leu | Thr | Cys | Ser | Pro | His | Arg | Gln | Arg | Arg | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| acc | aag | gac | aac | ttc | aat | gtc | tat | aaa | gcc | aca | aga | cca | tac | tta | gct | 528 |
| Thr | Lys | Asp | Asn | Phe | Asn | Val | Tyr | Lys | Ala | Thr | Arg | Pro | Tyr | Leu | Ala | |
| | | | | 165 | | | | | 170 | | | | | 175 | | |

| | | | | | | | | | | | | | | | | |
|---|---|---|---|---|---|---|---|---|---|---|---|---|---|---|---|---|
| cac | tgt | ccc | gac | tgt | gga | gaa | ggg | cac | tcg | tgc | cat | agt | ccc | gta | gca | 576 |
| His | Cys | Pro | Asp | Cys | Gly | Glu | Gly | His | Ser | Cys | His | Ser | Pro | Val | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| cta | gaa | cgc | atc | aga | aat | gaa | gcg | aca | gac | ggg | acg | ctg | aaa | atc | cag | 624 |
| Leu | Glu | Arg | Ile | Arg | Asn | Glu | Ala | Thr | Asp | Gly | Thr | Leu | Lys | Ile | Gln | |
| | | 195 | | | | | 200 | | | | | 205 | | | | |

| | | | | | | | | | | | | | | | | |
|---|---|---|---|---|---|---|---|---|---|---|---|---|---|---|---|---|
| gtc | tcc | ttg | caa | atc | gga | ata | aag | acg | gat | gac | agc | cac | gat | tgg | acc | 672 |
| Val | Ser | Leu | Gln | Ile | Gly | Ile | Lys | Thr | Asp | Asp | Ser | His | Asp | Trp | Thr | |
| | 210 | | | | | 215 | | | | | 220 | | | | | |

| | | | | | | | | | | | | | | | | |
|---|---|---|---|---|---|---|---|---|---|---|---|---|---|---|---|---|
| aag | ctg | cgt | tat | atg | gac | aac | cac | atg | cca | gca | gac | gca | gag | agg | gcg | 720 |
| Lys | Leu | Arg | Tyr | Met | Asp | Asn | His | Met | Pro | Ala | Asp | Ala | Glu | Arg | Ala | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ggg | cta | ttt | gta | aga | aca | tca | gca | ccg | tgt | acg | att | act | gga | aca | atg | 768 |
| Gly | Leu | Phe | Val | Arg | Thr | Ser | Ala | Pro | Cys | Thr | Ile | Thr | Gly | Thr | Met | |
| | | | | 245 | | | | | 250 | | | | | 255 | | |

| | | | | | | | | | | | | | | | | |
|---|---|---|---|---|---|---|---|---|---|---|---|---|---|---|---|---|
| gga | cac | ttc | atc | ctg | gcc | cga | tgt | cca | aaa | ggg | gaa | act | ctg | acg | gtg | 816 |
| Gly | His | Phe | Ile | Leu | Ala | Arg | Cys | Pro | Lys | Gly | Glu | Thr | Leu | Thr | Val | |
| | | | | 260 | | | | | 265 | | | | | 270 | | |

```
gga ttc act gac agt agg aag att agt cac tca tgt acg cac cca ttt      864
Gly Phe Thr Asp Ser Arg Lys Ile Ser His Ser Cys Thr His Pro Phe
        275                 280                 285 cac cac gac cct cct gtg ata ggt cgg gaa aaa ttc cat tcc cga ccg      912
His His Asp Pro Pro Val Ile Gly Arg Glu Lys Phe His Ser Arg Pro
290                 295                 300 cag cac ggt aaa gag cta cct tgc agc acg tac gtg cag agc acc gcc      960
Gln His Gly Lys Glu Leu Pro Cys Ser Thr Tyr Val Gln Ser Thr Ala
305                 310                 315                 320 gca act acc gag gag ata gag gta cac atg ccc cca gac acc cct gat     1008
Ala Thr Thr Glu Glu Ile Glu Val His Met Pro Pro Asp Thr Pro Asp
                325                 330                 335 cgc aca tta atg tca caa cag tcc ggc aac gta aag atc aca gtc aat     1056
Arg Thr Leu Met Ser Gln Gln Ser Gly Asn Val Lys Ile Thr Val Asn
            340                 345                 350 ggc cag acg gtg cgg tac aag tgt aat tgc ggt ggc tca aat gaa gga     1104
Gly Gln Thr Val Arg Tyr Lys Cys Asn Cys Gly Gly Ser Asn Glu Gly
        355                 360                 365 cta aca act aca gac aaa gtg att aat aac tgc aag gtt gat caa tgt     1152
Leu Thr Thr Thr Asp Lys Val Ile Asn Asn Cys Lys Val Asp Gln Cys
370                 375                 380 cat gcc gcg gtc acc aat cac aaa aag tgg cag tat aac tcc cct ctg     1200
His Ala Ala Val Thr Asn His Lys Lys Trp Gln Tyr Asn Ser Pro Leu
385                 390                 395                 400 gtc ccg cgt aat gct gaa ctt ggg gac cga aaa gga aaa att cac atc     1248
Val Pro Arg Asn Ala Glu Leu Gly Asp Arg Lys Gly Lys Ile His Ile
                405                 410                 415 ccg ttt ccg ctg gca aat gta aca tgc agg gtg cct aaa gca agg aac     1296
Pro Phe Pro Leu Ala Asn Val Thr Cys Arg Val Pro Lys Ala Arg Asn
            420                 425                 430 ccc acc gtg acg tac ggg aaa aac caa gtc atc atg cta ctg tat cct     1344
Pro Thr Val Thr Tyr Gly Lys Asn Gln Val Ile Met Leu Leu Tyr Pro
        435                 440                 445 gac cac cca aca ctc ctg tcc tac cgg aat atg gga gaa gaa cca aac     1392
Asp His Pro Thr Leu Leu Ser Tyr Arg Asn Met Gly Glu Glu Pro Asn
450                 455                 460 tat caa gaa gag tgg gtg atg cat aag aag gaa gtc gtg cta acc gtg     1440
Tyr Gln Glu Glu Trp Val Met His Lys Lys Glu Val Val Leu Thr Val
465                 470                 475                 480 ccg act gaa ggg ctc gag gtc acg tgg ggc aac aac gag ccg tat aag     1488
Pro Thr Glu Gly Leu Glu Val Thr Trp Gly Asn Asn Glu Pro Tyr Lys
                485                 490                 495 tat tgg ccg cag tta tct aca aac ggt aca gcc cat ggc cac ccg cat     1536
Tyr Trp Pro Gln Leu Ser Thr Asn Gly Thr Ala His Gly His Pro His
            500                 505                 510 gag ata att ctg tat tat tat gag ctg tac ccc act atg act gta gta     1584
Glu Ile Ile Leu Tyr Tyr Tyr Glu Leu Tyr Pro Thr Met Thr Val Val
        515                 520                 525 gtt gtg tca gtg gcc acg ttc ata ctc ctg tcg atg gtg ggt atg gca     1632
Val Val Ser Val Ala Thr Phe Ile Leu Leu Ser Met Val Gly Met Ala
530                 535                 540 gcg ggg atg tgc atg cgt gca cga cgc aga tgc atc aca ccg tat gaa     1680
Ala Gly Met Cys Met Arg Ala Arg Arg Arg Cys Ile Thr Pro Tyr Glu
545                 550                 555                 560 ctg aca cca gga gct acc gtc cct ttc ctg ctt agc cta ata tgc tgc     1728
Leu Thr Pro Gly Ala Thr Val Pro Phe Leu Leu Ser Leu Ile Cys Cys
                565                 570                 575 atc aga aca gct aaa gcg gcc aca tac caa gag gct gcg ata tac ctg     1776
Ile Arg Thr Ala Lys Ala Ala Thr Tyr Gln Glu Ala Ala Ile Tyr Leu
            580                 585                 590
```

-continued

```
tgg aac gag cag caa cct tta                                    1797
Trp Asn Glu Gln Gln Pro Leu
        595
```

<210> SEQ ID NO 5
<211> LENGTH: 599
<212> TYPE: PRT
<213> ORGANISM: Chikungunya virus

<400> SEQUENCE: 5

```
Ile Pro Val His Met Lys Ser Asp Ala Ser Lys Phe Thr His Glu Lys
1               5                   10                  15

Pro Glu Gly Tyr Tyr Asn Trp His His Gly Ala Val Gln Tyr Ser Gly
            20                  25                  30

Gly Arg Phe Thr Ile Pro Thr Gly Ala Gly Lys Pro Gly Asp Ser Gly
        35                  40                  45

Arg Pro Ile Phe Asp Asn Lys Gly Arg Val Val Ala Ile Val Leu Gly
    50                  55                  60

Gly Ala Asn Glu Gly Ala Arg Thr Ala Leu Ser Val Val Thr Trp Asn
65                  70                  75                  80

Lys Asp Ile Val Thr Lys Ile Thr Pro Glu Gly Ala Glu Glu Trp Ser
                85                  90                  95

Leu Ala Ile Pro Val Met Cys Leu Leu Ala Asn Thr Thr Phe Pro Cys
            100                 105                 110

Ser Gln Pro Pro Cys Thr Pro Cys Cys Tyr Glu Lys Glu Pro Glu Glu
        115                 120                 125

Thr Leu Arg Met Leu Glu Asp Asn Val Met Arg Pro Gly Tyr Tyr Gln
    130                 135                 140

Leu Leu Gln Ala Ser Leu Thr Cys Ser Pro His Arg Gln Arg Arg Ser
145                 150                 155                 160

Thr Lys Asp Asn Phe Asn Val Tyr Lys Ala Thr Arg Pro Tyr Leu Ala
                165                 170                 175

His Cys Pro Asp Cys Gly Glu Gly His Ser Cys His Ser Pro Val Ala
            180                 185                 190

Leu Glu Arg Ile Arg Asn Glu Ala Thr Asp Gly Thr Leu Lys Ile Gln
        195                 200                 205

Val Ser Leu Gln Ile Gly Ile Lys Thr Asp Asp Ser His Asp Trp Thr
    210                 215                 220

Lys Leu Arg Tyr Met Asp Asn His Met Pro Ala Asp Ala Glu Arg Ala
225                 230                 235                 240

Gly Leu Phe Val Arg Thr Ser Ala Pro Cys Thr Ile Thr Gly Thr Met
                245                 250                 255

Gly His Phe Ile Leu Ala Arg Cys Pro Lys Gly Glu Thr Leu Thr Val
            260                 265                 270

Gly Phe Thr Asp Ser Arg Lys Ile Ser His Ser Cys Thr His Pro Phe
        275                 280                 285

His His Asp Pro Pro Val Ile Gly Arg Glu Lys Phe His Ser Arg Pro
    290                 295                 300

Gln His Gly Lys Glu Leu Pro Cys Ser Thr Tyr Val Gln Ser Thr Ala
305                 310                 315                 320

Ala Thr Thr Glu Glu Ile Glu Val His Met Pro Pro Asp Thr Pro Asp
                325                 330                 335

Arg Thr Leu Met Ser Gln Gln Ser Gly Asn Val Lys Ile Thr Val Asn
            340                 345                 350
```

```
Gly Gln Thr Val Arg Tyr Lys Cys Asn Cys Gly Gly Ser Asn Glu Gly
            355                 360                 365

Leu Thr Thr Thr Asp Lys Val Ile Asn Cys Lys Val Asp Gln Cys
370                 375                 380

His Ala Ala Val Thr Asn His Lys Lys Trp Gln Tyr Asn Ser Pro Leu
385                 390                 395                 400

Val Pro Arg Asn Ala Glu Leu Gly Asp Arg Lys Gly Lys Ile His Ile
                405                 410                 415

Pro Phe Pro Leu Ala Asn Val Thr Cys Arg Val Pro Lys Ala Arg Asn
            420                 425                 430

Pro Thr Val Thr Tyr Gly Lys Asn Gln Val Ile Met Leu Leu Tyr Pro
            435                 440                 445

Asp His Pro Thr Leu Leu Ser Tyr Arg Asn Met Gly Glu Glu Pro Asn
450                 455                 460

Tyr Gln Glu Glu Trp Val Met His Lys Lys Glu Val Val Leu Thr Val
465                 470                 475                 480

Pro Thr Glu Gly Leu Glu Val Thr Trp Gly Asn Asn Glu Pro Tyr Lys
                485                 490                 495

Tyr Trp Pro Gln Leu Ser Thr Asn Gly Thr Ala His Gly His Pro His
            500                 505                 510

Glu Ile Ile Leu Tyr Tyr Tyr Glu Leu Tyr Pro Thr Met Thr Val Val
            515                 520                 525

Val Val Ser Val Ala Thr Phe Ile Leu Leu Ser Met Val Gly Met Ala
            530                 535                 540

Ala Gly Met Cys Met Arg Ala Arg Arg Cys Ile Thr Pro Tyr Glu
545                 550                 555                 560

Leu Thr Pro Gly Ala Thr Val Pro Phe Leu Leu Ser Leu Ile Cys Cys
                565                 570                 575

Ile Arg Thr Ala Lys Ala Ala Thr Tyr Gln Glu Ala Ala Ile Tyr Leu
            580                 585                 590

Trp Asn Glu Gln Gln Pro Leu
            595

<210> SEQ ID NO 6
<211> LENGTH: 1797
<212> TYPE: DNA
<213> ORGANISM: Chikungunya virus
<220> FEATURE:
<221> NAME/KEY: misc_feature
<223> OTHER INFORMATION: soluble glycoprotein E2 strain 06.27
<220> FEATURE:
<221> NAME/KEY: CDS
<222> LOCATION: (1)..(1797)

<400> SEQUENCE: 6 ata ccc gtg cac atg aag tcc gac gct tcg aag ttc acc cat gag aaa    48
Ile Pro Val His Met Lys Ser Asp Ala Ser Lys Phe Thr His Glu Lys
1               5                   10                  15 ccg gag ggg tac tac aac tgg cac cac gga gca gta cag tac tca gga    96
Pro Glu Gly Tyr Tyr Asn Trp His His Gly Ala Val Gln Tyr Ser Gly
            20                  25                  30 ggc cgg ttc acc atc cct aca ggt gct ggc aaa cca ggg gac agc ggc    144
Gly Arg Phe Thr Ile Pro Thr Gly Ala Gly Lys Pro Gly Asp Ser Gly
        35                  40                  45 aga ccg atc ttc gac aac aag gga cgc gtg gtg gcc ata gtc tta gga    192
Arg Pro Ile Phe Asp Asn Lys Gly Arg Val Val Ala Ile Val Leu Gly
    50                  55                  60 gga gct aat gaa gga gcc cgt aca gcc ctc tcg gtg gtg acc tgg aat    240
```

```
            Gly Ala Asn Glu Gly Ala Arg Thr Ala Leu Ser Val Val Thr Trp Asn
            65              70                  75                  80 aaa gac att gtc act aaa atc acc ccc gag ggg gcc gaa gag tgg agt          288
Lys Asp Ile Val Thr Lys Ile Thr Pro Glu Gly Ala Glu Glu Trp Ser
                85                  90                  95 ctt gcc atc cca gtt atg tgc ctg ttg gca aac acc acg ttc ccc tgc          336
Leu Ala Ile Pro Val Met Cys Leu Leu Ala Asn Thr Thr Phe Pro Cys
                100                 105                 110 tcc cag ccc cct tgc acg ccc tgc tgc tac gaa aag gaa ccg gag gaa          384
Ser Gln Pro Pro Cys Thr Pro Cys Cys Tyr Glu Lys Glu Pro Glu Glu
            115                 120                 125 acc cta cgc atg ctt gag gac aac gtc atg aga cct ggg tac tat cag          432
Thr Leu Arg Met Leu Glu Asp Asn Val Met Arg Pro Gly Tyr Tyr Gln
            130                 135                 140 ctg cta caa gca tcc tta aca tgt tct ccc cac cgc cag cga cgc agc          480
Leu Leu Gln Ala Ser Leu Thr Cys Ser Pro His Arg Gln Arg Arg Ser
145                 150                 155                 160 acc aag gac aac ttc aat gtc tat aaa gcc aca aga cca tac tta gct          528
Thr Lys Asp Asn Phe Asn Val Tyr Lys Ala Thr Arg Pro Tyr Leu Ala
                165                 170                 175 cac tgt ccc gac tgt gga gaa ggg cac tcg tgc cat agt ccc gta gca          576
His Cys Pro Asp Cys Gly Glu Gly His Ser Cys His Ser Pro Val Ala
                180                 185                 190 cta gaa cgc atc aga aat gaa gcg aca gac ggg acg ctg aaa atc cag          624
Leu Glu Arg Ile Arg Asn Glu Ala Thr Asp Gly Thr Leu Lys Ile Gln
            195                 200                 205 gtc tcc ttg caa atc gga ata aag acg gat gac agc cac gat tgg acc          672
Val Ser Leu Gln Ile Gly Ile Lys Thr Asp Asp Ser His Asp Trp Thr
210                 215                 220 aag ctg cgt tat atg gac aac cac atg cca gca gac gca gag agg gcg          720
Lys Leu Arg Tyr Met Asp Asn His Met Pro Ala Asp Ala Glu Arg Ala
225                 230                 235                 240 ggg cta ttt gta aga aca tca gca ccg tgt acg att act gga aca atg          768
Gly Leu Phe Val Arg Thr Ser Ala Pro Cys Thr Ile Thr Gly Thr Met
                245                 250                 255 gga cac ttc atc ctg gcc cga tgt cca aaa ggg gaa act ctg acg gtg          816
Gly His Phe Ile Leu Ala Arg Cys Pro Lys Gly Glu Thr Leu Thr Val
                260                 265                 270 gga ttc act gac agt agg aag att agt cac tca tgt acg cac cca ttt          864
Gly Phe Thr Asp Ser Arg Lys Ile Ser His Ser Cys Thr His Pro Phe
            275                 280                 285 cac cac gac cct cct gtg ata ggt cgg gaa aaa ttc cat tcc cga ccg          912
His His Asp Pro Pro Val Ile Gly Arg Glu Lys Phe His Ser Arg Pro
            290                 295                 300 cag cac ggt aaa gag cta cct tgc agc acg tac gtg cag agc acc gcc          960
Gln His Gly Lys Glu Leu Pro Cys Ser Thr Tyr Val Gln Ser Thr Ala
305                 310                 315                 320 gca act acc gag gag ata gag gta cac atg ccc cca gac acc cct gat         1008
Ala Thr Thr Glu Glu Ile Glu Val His Met Pro Pro Asp Thr Pro Asp
                325                 330                 335 cgc aca tta atg tca caa cag tcc ggc aac gta aag atc aca gtc aat         1056
Arg Thr Leu Met Ser Gln Gln Ser Gly Asn Val Lys Ile Thr Val Asn
                340                 345                 350 ggc cag acg gtg cgg tac aag tgt aat tgc ggt ggc tca aat gaa gga         1104
Gly Gln Thr Val Arg Tyr Lys Cys Asn Cys Gly Gly Ser Asn Glu Gly
            355                 360                 365 cta aca act aca gac aaa gtg att aat aac tgc aag gtt gat caa tgt         1152
Leu Thr Thr Thr Asp Lys Val Ile Asn Asn Cys Lys Val Asp Gln Cys
370                 375                 380
```

| | | | | | | | | | | | | | | | |
|---|---|---|---|---|---|---|---|---|---|---|---|---|---|---|---|
| cat | gcc | gcg | gtc | acc | aat | cac | aaa | aag | tgg | cag | tat | aac | tcc | cct | ctg | 1200
| His | Ala | Ala | Val | Thr | Asn | His | Lys | Lys | Trp | Gln | Tyr | Asn | Ser | Pro | Leu |
| 385 | | | | 390 | | | | | 395 | | | | | 400 | | gtc ccg cgt aat gct gaa ctt ggg gac cga aaa gga aaa att cac atc   1248
Val Pro Arg Asn Ala Glu Leu Gly Asp Arg Lys Gly Lys Ile His Ile
         405                 410                 415 ccg ttt ccg ctg gca aat gta aca tgc agg gtg cct aaa gca agg aac   1296
Pro Phe Pro Leu Ala Asn Val Thr Cys Arg Val Pro Lys Ala Arg Asn
             420                 425                 430 ccc acc gtg acg tac ggg aaa aac caa gtc atc atg cta ctg tat cct   1344
Pro Thr Val Thr Tyr Gly Lys Asn Gln Val Ile Met Leu Leu Tyr Pro
                 435                 440                 445 gac cac cca aca ctc ctg tcc tac cgg aat atg gga gaa gaa cca aac   1392
Asp His Pro Thr Leu Leu Ser Tyr Arg Asn Met Gly Glu Glu Pro Asn
     450                 455                 460 tat caa gaa gag tgg gtg atg cat aag aag gaa gtc gtg cta acc gtg   1440
Tyr Gln Glu Glu Trp Val Met His Lys Lys Glu Val Val Leu Thr Val
465                 470                 475                 480 ccg act gaa ggg ctc gag gtc acg tgg ggc aac aac gag ccg tat aag   1488
Pro Thr Glu Gly Leu Glu Val Thr Trp Gly Asn Asn Glu Pro Tyr Lys
                485                 490                 495 tat tgg ccg cag tta tct aca aac ggt aca gcc cat ggc cac ccg cat   1536
Tyr Trp Pro Gln Leu Ser Thr Asn Gly Thr Ala His Gly His Pro His
            500                 505                 510 gag ata att ctg tat tat tat gag ctg tac ccc act atg act gta gta   1584
Glu Ile Ile Leu Tyr Tyr Tyr Glu Leu Tyr Pro Thr Met Thr Val Val
        515                 520                 525 gtt gtg tca gtg gcc acg ttc ata ctc ctg tcg atg gtg ggt atg gca   1632
Val Val Ser Val Ala Thr Phe Ile Leu Leu Ser Met Val Gly Met Ala
    530                 535                 540 gcg ggg atg tgc atg tgt gca cga cga aga tgc atc aca ccg tat gaa   1680
Ala Gly Met Cys Met Cys Ala Arg Arg Arg Cys Ile Thr Pro Tyr Glu
545                 550                 555                 560 ctg aca cca gga gct acc gtc cct ttc ctg ctt agc cta ata tgc tgc   1728
Leu Thr Pro Gly Ala Thr Val Pro Phe Leu Leu Ser Leu Ile Cys Cys
                565                 570                 575 atc aga aca gct aaa gcg gcc aca tac caa gag gct gcg ata tac ctg   1776
Ile Arg Thr Ala Lys Ala Ala Thr Tyr Gln Glu Ala Ala Ile Tyr Leu
            580                 585                 590 tgg aac gag cag caa cct tta                                       1797
Trp Asn Glu Gln Gln Pro Leu
        595

<210> SEQ ID NO 7
<211> LENGTH: 599
<212> TYPE: PRT
<213> ORGANISM: Chikungunya virus

<400> SEQUENCE: 7

Ile Pro Val His Met Lys Ser Asp Ala Ser Lys Phe Thr His Glu Lys
1               5                   10                  15

Pro Glu Gly Tyr Tyr Asn Trp His His Gly Ala Val Gln Tyr Ser Gly
            20                  25                  30

Gly Arg Phe Thr Ile Pro Thr Gly Ala Gly Lys Pro Gly Asp Ser Gly
        35                  40                  45

Arg Pro Ile Phe Asp Asn Lys Gly Arg Val Val Ala Ile Val Leu Gly
    50                  55                  60

Gly Ala Asn Glu Gly Ala Arg Thr Ala Leu Ser Val Val Thr Trp Asn
65                  70                  75                  80

```
Lys Asp Ile Val Thr Lys Ile Thr Pro Glu Gly Ala Glu Glu Trp Ser
                85                  90                  95
Leu Ala Ile Pro Val Met Cys Leu Leu Ala Asn Thr Thr Phe Pro Cys
            100                 105                 110
Ser Gln Pro Pro Cys Thr Pro Cys Cys Tyr Glu Lys Glu Pro Glu Glu
        115                 120                 125
Thr Leu Arg Met Leu Glu Asp Asn Val Met Arg Pro Gly Tyr Tyr Gln
    130                 135                 140
Leu Leu Gln Ala Ser Leu Thr Cys Ser Pro His Arg Gln Arg Arg Ser
145                 150                 155                 160
Thr Lys Asp Asn Phe Asn Val Tyr Lys Ala Thr Arg Pro Tyr Leu Ala
                165                 170                 175
His Cys Pro Asp Cys Gly Glu Gly His Ser Cys His Ser Pro Val Ala
            180                 185                 190
Leu Glu Arg Ile Arg Asn Glu Ala Thr Asp Gly Thr Leu Lys Ile Gln
        195                 200                 205
Val Ser Leu Gln Ile Gly Ile Lys Thr Asp Asp Ser His Asp Trp Thr
    210                 215                 220
Lys Leu Arg Tyr Met Asp Asn His Met Pro Ala Asp Ala Glu Arg Ala
225                 230                 235                 240
Gly Leu Phe Val Arg Thr Ser Ala Pro Cys Thr Ile Thr Gly Thr Met
                245                 250                 255
Gly His Phe Ile Leu Ala Arg Cys Pro Lys Gly Glu Thr Leu Thr Val
            260                 265                 270
Gly Phe Thr Asp Ser Arg Lys Ile Ser His Ser Cys Thr His Pro Phe
        275                 280                 285
His His Asp Pro Pro Val Ile Gly Arg Glu Lys Phe His Ser Arg Pro
    290                 295                 300
Gln His Gly Lys Glu Leu Pro Cys Ser Thr Tyr Val Gln Ser Thr Ala
305                 310                 315                 320
Ala Thr Thr Glu Glu Ile Glu Val His Met Pro Pro Asp Thr Pro Asp
                325                 330                 335
Arg Thr Leu Met Ser Gln Gln Ser Gly Asn Val Lys Ile Thr Val Asn
            340                 345                 350
Gly Gln Thr Val Arg Tyr Lys Cys Asn Cys Gly Gly Ser Asn Glu Gly
        355                 360                 365
Leu Thr Thr Thr Asp Lys Val Ile Asn Asn Cys Lys Val Asp Gln Cys
    370                 375                 380
His Ala Ala Val Thr Asn His Lys Lys Trp Gln Tyr Asn Ser Pro Leu
385                 390                 395                 400
Val Pro Arg Asn Ala Glu Leu Gly Asp Arg Lys Gly Lys Ile His Ile
                405                 410                 415
Pro Phe Pro Leu Ala Asn Val Thr Cys Arg Val Pro Lys Ala Arg Asn
            420                 425                 430
Pro Thr Val Thr Tyr Gly Lys Asn Gln Val Ile Met Leu Leu Tyr Pro
        435                 440                 445
Asp His Pro Thr Leu Leu Ser Tyr Arg Asn Met Gly Glu Glu Pro Asn
    450                 455                 460
Tyr Gln Glu Glu Trp Val Met His Lys Lys Glu Val Val Leu Thr Val
465                 470                 475                 480
Pro Thr Glu Gly Leu Glu Val Thr Trp Gly Asn Asn Glu Pro Tyr Lys
                485                 490                 495
Tyr Trp Pro Gln Leu Ser Thr Asn Gly Thr Ala His Gly His Pro His
```

```
                    500                 505                 510
Glu Ile Ile Leu Tyr Tyr Tyr Glu Leu Tyr Pro Thr Met Thr Val Val
            515                 520                 525

Val Val Ser Val Ala Thr Phe Ile Leu Leu Ser Met Val Gly Met Ala
530                 535                 540

Ala Gly Met Cys Met Cys Ala Arg Arg Arg Cys Ile Thr Pro Tyr Glu
545                 550                 555                 560

Leu Thr Pro Gly Ala Thr Val Pro Phe Leu Leu Ser Leu Ile Cys Cys
                565                 570                 575

Ile Arg Thr Ala Lys Ala Ala Thr Tyr Gln Glu Ala Ala Ile Tyr Leu
            580                 585                 590

Trp Asn Glu Gln Gln Pro Leu
        595

<210> SEQ ID NO 8
<211> LENGTH: 1797
<212> TYPE: DNA
<213> ORGANISM: Chikungunya virus
<220> FEATURE:
<221> NAME/KEY: misc_feature
<223> OTHER INFORMATION: soluble glycoprotein E2 strain 06.49
<220> FEATURE:
<221> NAME/KEY: CDS
<222> LOCATION: (1)..(1797)

<400> SEQUENCE: 8 ata ccc gtg cac atg aag tcc gac gct tcg aag ttc acc cat gag aaa      48
Ile Pro Val His Met Lys Ser Asp Ala Ser Lys Phe Thr His Glu Lys
1               5                   10                  15 ccg gag ggg tac tac aac tgg cac cac gga gca gta cag tac tca gga      96
Pro Glu Gly Tyr Tyr Asn Trp His His Gly Ala Val Gln Tyr Ser Gly
            20                  25                  30 ggc cgg ttc acc atc cct aca ggt gct ggc aaa cca ggg gac agc ggc     144
Gly Arg Phe Thr Ile Pro Thr Gly Ala Gly Lys Pro Gly Asp Ser Gly
        35                  40                  45 aga ccg atc ttc gac aac aag gga cgc gtg gtg gcc ata gtc tta gga     192
Arg Pro Ile Phe Asp Asn Lys Gly Arg Val Val Ala Ile Val Leu Gly
    50                  55                  60 gga gct aat gaa gga gcc cgt aca gcc ctc tcg gtg gtg acc tgg aat     240
Gly Ala Asn Glu Gly Ala Arg Thr Ala Leu Ser Val Val Thr Trp Asn
65                  70                  75                  80 aaa gac att gtc act aaa atc acc ccc gag ggg gcc gaa gag tgg agt     288
Lys Asp Ile Val Thr Lys Ile Thr Pro Glu Gly Ala Glu Glu Trp Ser
                85                  90                  95 ctt gcc atc cca gtt atg tgc ctg ttg gca aac acc acg ttc ccc tgc     336
Leu Ala Ile Pro Val Met Cys Leu Leu Ala Asn Thr Thr Phe Pro Cys
            100                 105                 110 tcc cag ccc cct tgc acg ccc tgc tgc tac gaa aag gaa ccg gag gaa     384
Ser Gln Pro Pro Cys Thr Pro Cys Cys Tyr Glu Lys Glu Pro Glu Glu
        115                 120                 125 acc cta cgc atg ctt gag gac aac gtc atg aga cct ggg tac tat cag     432
Thr Leu Arg Met Leu Glu Asp Asn Val Met Arg Pro Gly Tyr Tyr Gln
    130                 135                 140 ctg cta caa gca tcc tta aca tgt tct ccc cac cgc cag cga cgc agc     480
Leu Leu Gln Ala Ser Leu Thr Cys Ser Pro His Arg Gln Arg Arg Ser
145                 150                 155                 160 acc aag gac aac ttc aat gtc tat aaa gcc aca aga cca tac tta gct     528
Thr Lys Asp Asn Phe Asn Val Tyr Lys Ala Thr Arg Pro Tyr Leu Ala
                165                 170                 175 cac tgt ccc gac tgt gga gaa ggg cac tcg tgc cat agt ccc gta gca     576
```

```
His Cys Pro Asp Cys Gly Glu Gly His Ser Cys His Ser Pro Val Ala
            180                 185                 190 cta gaa cgc atc aga aat gaa gcg aca gac ggg acg ctg aaa atc cag          624
Leu Glu Arg Ile Arg Asn Glu Ala Thr Asp Gly Thr Leu Lys Ile Gln
            195                 200                 205 gtc tcc ttg caa atc gga ata aag acg gat gac agc cac gat tgg acc          672
Val Ser Leu Gln Ile Gly Ile Lys Thr Asp Asp Ser His Asp Trp Thr
210                 215                 220 aag ctg cgt tat atg gac aac cac atg cca gca gac gca gag agg gcg          720
Lys Leu Arg Tyr Met Asp Asn His Met Pro Ala Asp Ala Glu Arg Ala
225                 230                 235                 240 ggg cta ttt gta aga aca tca gca ccg tgt acg att act gga aca atg          768
Gly Leu Phe Val Arg Thr Ser Ala Pro Cys Thr Ile Thr Gly Thr Met
                245                 250                 255 gga cac ttc atc ctg gcc cga tgt cca aaa ggg gaa act ctg acg gtg          816
Gly His Phe Ile Leu Ala Arg Cys Pro Lys Gly Glu Thr Leu Thr Val
                260                 265                 270 gga ttc act gac agt agg aag att agt cac tca tgt acg cac cca ttt          864
Gly Phe Thr Asp Ser Arg Lys Ile Ser His Ser Cys Thr His Pro Phe
                275                 280                 285 cac cac gac cct cct gtg ata ggt cgg gaa aaa ttc cat tcc cga ccg          912
His His Asp Pro Pro Val Ile Gly Arg Glu Lys Phe His Ser Arg Pro
            290                 295                 300 cag cac ggt aaa gag cta cct tgc agc acg tac gtg cag agc acc gcc          960
Gln His Gly Lys Glu Leu Pro Cys Ser Thr Tyr Val Gln Ser Thr Ala
305                 310                 315                 320 gca act acc gag gag ata gag gta cac atg ccc cca gac acc cct gat         1008
Ala Thr Thr Glu Glu Ile Glu Val His Met Pro Pro Asp Thr Pro Asp
                325                 330                 335 cgc aca tta atg tca caa cag tcc ggc aac gta aag atc aca gtc aat         1056
Arg Thr Leu Met Ser Gln Gln Ser Gly Asn Val Lys Ile Thr Val Asn
                340                 345                 350 ggc cag acg gtg cgg tac aag tgt aat tgc ggt ggc tca aat gaa gga         1104
Gly Gln Thr Val Arg Tyr Lys Cys Asn Cys Gly Gly Ser Asn Glu Gly
                355                 360                 365 cta aca act aca gac aaa gtg att aat aac tgc aag gtt gat caa tgt         1152
Leu Thr Thr Thr Asp Lys Val Ile Asn Asn Cys Lys Val Asp Gln Cys
370                 375                 380 cat gcc gcg gtc acc aat cac aaa aag tgg cag tat aac tcc cct ctg         1200
His Ala Ala Val Thr Asn His Lys Lys Trp Gln Tyr Asn Ser Pro Leu
385                 390                 395                 400 gtc ccg cgt aat gct gaa ctt ggg gac cga aaa gga aaa att cac atc         1248
Val Pro Arg Asn Ala Glu Leu Gly Asp Arg Lys Gly Lys Ile His Ile
                405                 410                 415 ccg ttt ccg ctg gca aat gta aca tgc agg gtg cct aaa gca agg aac         1296
Pro Phe Pro Leu Ala Asn Val Thr Cys Arg Val Pro Lys Ala Arg Asn
                420                 425                 430 ccc acc gtg acg tac ggg aaa aac caa gtc atc atg cta ctg tat cct         1344
Pro Thr Val Thr Tyr Gly Lys Asn Gln Val Ile Met Leu Leu Tyr Pro
                435                 440                 445 gac cac cca aca ctc ctg tcc tac cgg aat atg gga gaa gaa cca aac         1392
Asp His Pro Thr Leu Leu Ser Tyr Arg Asn Met Gly Glu Glu Pro Asn
450                 455                 460 tat caa gaa gag tgg gtg atg cat aag aag gaa gtc gtg cta acc gtg         1440
Tyr Gln Glu Glu Trp Val Met His Lys Lys Glu Val Val Leu Thr Val
465                 470                 475                 480 ccg act gaa ggg ctc gag gtc acg tgg ggc aac aac gag ccg tat aag         1488
Pro Thr Glu Gly Leu Glu Val Thr Trp Gly Asn Asn Glu Pro Tyr Lys
                485                 490                 495
```

```
tat tgg ccg cag tta tct aca aac ggt aca gcc cat ggc cac ccg cac    1536
Tyr Trp Pro Gln Leu Ser Thr Asn Gly Thr Ala His Gly His Pro His
            500                 505                 510 gag ata att ctg tat tat tat gag ctg tac ccc act atg act gta gta    1584
Glu Ile Ile Leu Tyr Tyr Tyr Glu Leu Tyr Pro Thr Met Thr Val Val
        515                 520                 525 gtt gtg tca gtg gcc acg ttc ata ctc ctg tcg atg gtg ggt atg gca    1632
Val Val Ser Val Ala Thr Phe Ile Leu Leu Ser Met Val Gly Met Ala
530                 535                 540 gcg ggg atg tgc atg tgt gca cga cgc aga tgc atc aca ccg tat gaa    1680
Ala Gly Met Cys Met Cys Ala Arg Arg Arg Cys Ile Thr Pro Tyr Glu
545                 550                 555                 560 ctg aca cca gga gct acc gtc cct ttc ctg ctt agc cta ata tgc tgc    1728
Leu Thr Pro Gly Ala Thr Val Pro Phe Leu Leu Ser Leu Ile Cys Cys
                565                 570                 575 atc aga aca gct aaa gcg gcc aca tac caa gag gct gcg ata tac ctg    1776
Ile Arg Thr Ala Lys Ala Ala Thr Tyr Gln Glu Ala Ala Ile Tyr Leu
            580                 585                 590 tgg aac gag cag caa cct tta                                        1797
Trp Asn Glu Gln Gln Pro Leu
        595

<210> SEQ ID NO 9
<211> LENGTH: 599
<212> TYPE: PRT
<213> ORGANISM: Chikungunya virus

<400> SEQUENCE: 9

Ile Pro Val His Met Lys Ser Asp Ala Ser Lys Phe Thr His Glu Lys
1               5                   10                  15

Pro Glu Gly Tyr Tyr Asn Trp His His Gly Ala Val Gln Tyr Ser Gly
            20                  25                  30

Gly Arg Phe Thr Ile Pro Thr Gly Ala Gly Lys Pro Gly Asp Ser Gly
        35                  40                  45

Arg Pro Ile Phe Asp Asn Lys Gly Arg Val Val Ala Ile Val Leu Gly
    50                  55                  60

Gly Ala Asn Glu Gly Ala Arg Thr Ala Leu Ser Val Val Thr Trp Asn
65                  70                  75                  80

Lys Asp Ile Val Thr Lys Ile Thr Pro Glu Gly Ala Glu Glu Trp Ser
                85                  90                  95

Leu Ala Ile Pro Val Met Cys Leu Leu Ala Asn Thr Thr Phe Pro Cys
            100                 105                 110

Ser Gln Pro Pro Cys Thr Pro Cys Cys Tyr Glu Lys Glu Pro Glu Glu
        115                 120                 125

Thr Leu Arg Met Leu Glu Asp Asn Val Met Arg Pro Gly Tyr Tyr Gln
    130                 135                 140

Leu Leu Gln Ala Ser Leu Thr Cys Ser Pro His Arg Gln Arg Arg Ser
145                 150                 155                 160

Thr Lys Asp Asn Phe Asn Val Tyr Lys Ala Thr Arg Pro Tyr Leu Ala
                165                 170                 175

His Cys Pro Asp Cys Gly Glu Gly His Ser Cys His Ser Pro Val Ala
            180                 185                 190

Leu Glu Arg Ile Arg Asn Glu Ala Thr Asp Gly Thr Leu Lys Ile Gln
        195                 200                 205

Val Ser Leu Gln Ile Gly Ile Lys Thr Asp Asp Ser His Asp Trp Thr
    210                 215                 220

Lys Leu Arg Tyr Met Asp Asn His Met Pro Ala Asp Ala Glu Arg Ala
```

```
            225                 230                 235                 240
        Gly Leu Phe Val Arg Thr Ser Ala Pro Cys Thr Ile Thr Gly Thr Met
                        245                 250                 255

Gly His Phe Ile Leu Ala Arg Cys Pro Lys Gly Glu Thr Leu Thr Val
                        260                 265                 270

Gly Phe Thr Asp Ser Arg Lys Ile Ser His Ser Cys Thr His Pro Phe
                        275                 280                 285

His His Asp Pro Pro Val Ile Gly Arg Glu Lys Phe His Ser Arg Pro
                        290                 295                 300

Gln His Gly Lys Glu Leu Pro Cys Ser Thr Tyr Val Gln Ser Thr Ala
        305                 310                 315                 320

Ala Thr Thr Glu Glu Ile Glu Val His Met Pro Pro Asp Thr Pro Asp
                        325                 330                 335

Arg Thr Leu Met Ser Gln Gln Ser Gly Asn Val Lys Ile Thr Val Asn
                        340                 345                 350

Gly Gln Thr Val Arg Tyr Lys Cys Asn Cys Gly Gly Ser Asn Glu Gly
                        355                 360                 365

Leu Thr Thr Thr Asp Lys Val Ile Asn Asn Cys Lys Val Asp Gln Cys
                        370                 375                 380

His Ala Ala Val Thr Asn His Lys Lys Trp Gln Tyr Asn Ser Pro Leu
        385                 390                 395                 400

Val Pro Arg Asn Ala Glu Leu Gly Asp Arg Lys Gly Lys Ile His Ile
                        405                 410                 415

Pro Phe Pro Leu Ala Asn Val Thr Cys Arg Val Pro Lys Ala Arg Asn
                        420                 425                 430

Pro Thr Val Thr Tyr Gly Lys Asn Gln Val Ile Met Leu Leu Tyr Pro
                        435                 440                 445

Asp His Pro Thr Leu Leu Ser Tyr Arg Asn Met Gly Glu Glu Pro Asn
                        450                 455                 460

Tyr Gln Glu Glu Trp Val Met His Lys Lys Glu Val Val Leu Thr Val
        465                 470                 475                 480

Pro Thr Glu Gly Leu Glu Val Thr Trp Gly Asn Asn Glu Pro Tyr Lys
                        485                 490                 495

Tyr Trp Pro Gln Leu Ser Thr Asn Gly Thr Ala His Gly His Pro His
                        500                 505                 510

Glu Ile Ile Leu Tyr Tyr Tyr Glu Leu Tyr Pro Thr Met Thr Val Val
                        515                 520                 525

Val Val Ser Val Ala Thr Phe Ile Leu Leu Ser Met Val Gly Met Ala
                        530                 535                 540

Ala Gly Met Cys Met Cys Ala Arg Arg Arg Cys Ile Thr Pro Tyr Glu
        545                 550                 555                 560

Leu Thr Pro Gly Ala Thr Val Pro Phe Leu Leu Ser Leu Ile Cys Cys
                        565                 570                 575

Ile Arg Thr Ala Lys Ala Ala Thr Tyr Gln Glu Ala Ala Ile Tyr Leu
                        580                 585                 590

Trp Asn Glu Gln Gln Pro Leu
                595

<210> SEQ ID NO 10
<211> LENGTH: 1092
<212> TYPE: DNA
<213> ORGANISM: Chikungunya virus
<220> FEATURE:
<221> NAME/KEY: misc_feature
<223> OTHER INFORMATION: ectodomain glycoprotein E2 strain 05.115
```

<220> FEATURE:
<221> NAME/KEY: CDS
<222> LOCATION: (1)..(1092)

<400> SEQUENCE: 10

```
gac aac ttc aat gtc tat aaa gcc aca aga cca tac tta gct cac tgt      48
Asp Asn Phe Asn Val Tyr Lys Ala Thr Arg Pro Tyr Leu Ala His Cys
1               5                   10                  15 ccc gac tgt gga gaa ggg cac tcg tgc cat agt ccc gta gca cta gaa      96
Pro Asp Cys Gly Glu Gly His Ser Cys His Ser Pro Val Ala Leu Glu
            20                  25                  30 cgc atc aga aat gaa gcg aca gac ggg acg ctg aaa atc cag gtc tcc     144
Arg Ile Arg Asn Glu Ala Thr Asp Gly Thr Leu Lys Ile Gln Val Ser
        35                  40                  45 ttg caa atc gga ata aag acg gat gac agc cac gat tgg acc aag ctg     192
Leu Gln Ile Gly Ile Lys Thr Asp Asp Ser His Asp Trp Thr Lys Leu
    50                  55                  60 cgt tat atg gac aac cac atg cca gca gac gca gag agg gcg ggg cta     240
Arg Tyr Met Asp Asn His Met Pro Ala Asp Ala Glu Arg Ala Gly Leu
65                  70                  75                  80 ttt gta aga aca tca gca ccg tgt acg att act gga aca atg gga cac     288
Phe Val Arg Thr Ser Ala Pro Cys Thr Ile Thr Gly Thr Met Gly His
                85                  90                  95 ttc atc ctg gcc cga tgt cca aaa ggg gaa act ctg acg gtg gga ttc     336
Phe Ile Leu Ala Arg Cys Pro Lys Gly Glu Thr Leu Thr Val Gly Phe
            100                 105                 110 act gac agt agg aag att agt cac tca tgt acg cac cca ttt cac cac     384
Thr Asp Ser Arg Lys Ile Ser His Ser Cys Thr His Pro Phe His His
        115                 120                 125 gac cct cct gtg ata ggt cgg gaa aaa ttc cat tcc cga ccg cag cac     432
Asp Pro Pro Val Ile Gly Arg Glu Lys Phe His Ser Arg Pro Gln His
    130                 135                 140 ggt aaa gag ata cct tgc agc acg tac gtg cag agc acc gcc gca act     480
Gly Lys Glu Ile Pro Cys Ser Thr Tyr Val Gln Ser Thr Ala Ala Thr
145                 150                 155                 160 acc gag gag ata gag gta cac atg ccc cca gac acc cct gat cgc aca     528
Thr Glu Glu Ile Glu Val His Met Pro Pro Asp Thr Pro Asp Arg Thr
                165                 170                 175 tta atg tca caa cag tcc ggc aac gta aag atc aca gtc aat ggc cag     576
Leu Met Ser Gln Gln Ser Gly Asn Val Lys Ile Thr Val Asn Gly Gln
            180                 185                 190 acg gtg cgg tac aag tgt aat tgc ggt ggc tca aat gaa gga cta aca     624
Thr Val Arg Tyr Lys Cys Asn Cys Gly Gly Ser Asn Glu Gly Leu Thr
        195                 200                 205 act aca gac aaa gtg att aat aac tgc aag gtt gat caa tgt cat gcc     672
Thr Thr Asp Lys Val Ile Asn Asn Cys Lys Val Asp Gln Cys His Ala
    210                 215                 220 gcg gtc acc aat cac aaa aag tgg cag tat aac tcc cct ctg gtc ccg     720
Ala Val Thr Asn His Lys Lys Trp Gln Tyr Asn Ser Pro Leu Val Pro
225                 230                 235                 240 cgt aat gct gaa ctt ggg gac cga aaa gga aaa att cac atc ccg ttt     768
Arg Asn Ala Glu Leu Gly Asp Arg Lys Gly Lys Ile His Ile Pro Phe
                245                 250                 255 ccg ctg gca aat gta aca tgc agg gtg cct aaa gca agg aac ccc acc     816
Pro Leu Ala Asn Val Thr Cys Arg Val Pro Lys Ala Arg Asn Pro Thr
            260                 265                 270 gtg acg tac ggg aaa aac caa gtc atc atg cta ctg tat cct gac cac     864
Val Thr Tyr Gly Lys Asn Gln Val Ile Met Leu Leu Tyr Pro Asp His
        275                 280                 285 cca aca ctc ctg tcc tac cgg aat atg gga gaa gaa cca aac tat caa     912
```

```
Pro Thr Leu Leu Ser Tyr Arg Asn Met Gly Glu Glu Pro Asn Tyr Gln
    290                 295                 300 gaa gag tgg gtg atg cat aag aag gaa gtc gtg cta acc gtg ccg act      960
Glu Glu Trp Val Met His Lys Lys Glu Val Val Leu Thr Val Pro Thr
305                 310                 315                 320 gaa ggg ctc gag gtc acg tgg ggc aac aac gag ccg tat aag tat tgg     1008
Glu Gly Leu Glu Val Thr Trp Gly Asn Asn Glu Pro Tyr Lys Tyr Trp
                325                 330                 335 ccg cag tta tct aca aac ggt aca gcc cat ggc cac ccg cat gag ata     1056
Pro Gln Leu Ser Thr Asn Gly Thr Ala His Gly His Pro His Glu Ile
            340                 345                 350 att ctg tat tat tat gag ctg tac ccc act atg act                     1092
Ile Leu Tyr Tyr Tyr Glu Leu Tyr Pro Thr Met Thr
        355                 360

<210> SEQ ID NO 11
<211> LENGTH: 364
<212> TYPE: PRT
<213> ORGANISM: Chikungunya virus

<400> SEQUENCE: 11

Asp Asn Phe Asn Val Tyr Lys Ala Thr Arg Pro Tyr Leu Ala His Cys
1               5                   10                  15

Pro Asp Cys Gly Glu Gly His Ser Cys His Ser Pro Val Ala Leu Glu
            20                  25                  30

Arg Ile Arg Asn Glu Ala Thr Asp Gly Thr Leu Lys Ile Gln Val Ser
        35                  40                  45

Leu Gln Ile Gly Ile Lys Thr Asp Asp Ser His Asp Trp Thr Lys Leu
    50                  55                  60

Arg Tyr Met Asp Asn His Met Pro Ala Asp Ala Glu Arg Ala Gly Leu
65                  70                  75                  80

Phe Val Arg Thr Ser Ala Pro Cys Thr Ile Thr Gly Thr Met Gly His
                85                  90                  95

Phe Ile Leu Ala Arg Cys Pro Lys Gly Glu Thr Leu Thr Val Gly Phe
            100                 105                 110

Thr Asp Ser Arg Lys Ile Ser His Ser Cys Thr His Pro Phe His His
        115                 120                 125

Asp Pro Pro Val Ile Gly Arg Glu Lys Phe His Ser Arg Pro Gln His
    130                 135                 140

Gly Lys Glu Ile Pro Cys Ser Thr Tyr Val Gln Ser Thr Ala Ala Thr
145                 150                 155                 160

Thr Glu Glu Ile Glu Val His Met Pro Pro Asp Thr Pro Asp Arg Thr
                165                 170                 175

Leu Met Ser Gln Gln Ser Gly Asn Val Lys Ile Thr Val Asn Gly Gln
            180                 185                 190

Thr Val Arg Tyr Lys Cys Asn Cys Gly Gly Ser Asn Glu Gly Leu Thr
        195                 200                 205

Thr Thr Asp Lys Val Ile Asn Asn Cys Lys Val Asp Gln Cys His Ala
    210                 215                 220

Ala Val Thr Asn His Lys Lys Trp Gln Tyr Asn Ser Pro Leu Val Pro
225                 230                 235                 240

Arg Asn Ala Glu Leu Gly Asp Arg Lys Gly Lys Ile His Ile Pro Phe
                245                 250                 255

Pro Leu Ala Asn Val Thr Cys Arg Val Pro Lys Ala Arg Asn Pro Thr
            260                 265                 270

Val Thr Tyr Gly Lys Asn Gln Val Ile Met Leu Leu Tyr Pro Asp His
```

```
                275                 280                 285
Pro Thr Leu Leu Ser Tyr Arg Asn Met Gly Glu Glu Pro Asn Tyr Gln
        290                 295                 300
Glu Glu Trp Val Met His Lys Lys Glu Val Val Leu Thr Val Pro Thr
305                 310                 315                 320
Glu Gly Leu Glu Val Thr Trp Gly Asn Asn Glu Pro Tyr Lys Tyr Trp
                325                 330                 335
Pro Gln Leu Ser Thr Asn Gly Thr Ala His Gly His Pro His Glu Ile
        340                 345                 350
Ile Leu Tyr Tyr Tyr Glu Leu Tyr Pro Thr Met Thr
                355                 360

<210> SEQ ID NO 12
<211> LENGTH: 1092
<212> TYPE: DNA
<213> ORGANISM: Chikungunya virus
<220> FEATURE:
<221> NAME/KEY: misc_feature
<223> OTHER INFORMATION: ectodomain glycoprotein E2 strain 06.21
<220> FEATURE:
<221> NAME/KEY: CDS
<222> LOCATION: (1)..(1092)

<400> SEQUENCE: 12 gac aac ttc aat gtc tat aaa gcc aca aga cca tac tta gct cac tgt      48
Asp Asn Phe Asn Val Tyr Lys Ala Thr Arg Pro Tyr Leu Ala His Cys
1               5                   10                  15 ccc gac tgt gga gaa ggg cac tcg tgc cat agt ccc gta gca cta gaa      96
Pro Asp Cys Gly Glu Gly His Ser Cys His Ser Pro Val Ala Leu Glu
                20                  25                  30 cgc atc aga aat gaa gcg aca gac ggg acg ctg aaa atc cag gtc tcc     144
Arg Ile Arg Asn Glu Ala Thr Asp Gly Thr Leu Lys Ile Gln Val Ser
            35                  40                  45 ttg caa atc gga ata aag acg gat gac agc cac gat tgg acc aag ctg     192
Leu Gln Ile Gly Ile Lys Thr Asp Asp Ser His Asp Trp Thr Lys Leu
        50                  55                  60 cgt tat atg gac aac cac atg cca gca gac gca gag agg gcg ggg cta     240
Arg Tyr Met Asp Asn His Met Pro Ala Asp Ala Glu Arg Ala Gly Leu
65                  70                  75                  80 ttt gta aga aca tca gca ccg tgt acg att act gga aca atg gga cac     288
Phe Val Arg Thr Ser Ala Pro Cys Thr Ile Thr Gly Thr Met Gly His
                85                  90                  95 ttc atc ctg gcc cga tgt cca aaa ggg gaa act ctg acg gtg gga ttc     336
Phe Ile Leu Ala Arg Cys Pro Lys Gly Glu Thr Leu Thr Val Gly Phe
                100                 105                 110 act gac agt agg aag att agt cac tca tgt acg cac cca ttt cac cac     384
Thr Asp Ser Arg Lys Ile Ser His Ser Cys Thr His Pro Phe His His
            115                 120                 125 gac cct cct gtg ata ggt cgg gaa aaa ttc cat tcc cga ccg cag cac     432
Asp Pro Pro Val Ile Gly Arg Glu Lys Phe His Ser Arg Pro Gln His
        130                 135                 140 ggt aaa gag cta cct tgc agc acg tac gtg cag agc acc gcc gca act     480
Gly Lys Glu Leu Pro Cys Ser Thr Tyr Val Gln Ser Thr Ala Ala Thr
145                 150                 155                 160 acc gag gag ata gag gta cac atg ccc cca gac acc cct gat cgc aca     528
Thr Glu Glu Ile Glu Val His Met Pro Pro Asp Thr Pro Asp Arg Thr
                165                 170                 175 tta atg tca caa cag tcc ggc aac gta aag atc aca gtc aat ggc cag     576
Leu Met Ser Gln Gln Ser Gly Asn Val Lys Ile Thr Val Asn Gly Gln
            180                 185                 190
```

| | |
|---|---|
| acg gtg cgg tac aag tgt aat tgc ggt ggc tca aat gaa gga cta aca<br>Thr Val Arg Tyr Lys Cys Asn Cys Gly Gly Ser Asn Glu Gly Leu Thr<br>     195                    200                 205 | 624 |
| act aca gac aaa gtg att aat aac tgc aag gtt gat caa tgt cat gcc<br>Thr Thr Asp Lys Val Ile Asn Asn Cys Lys Val Asp Gln Cys His Ala<br>210                    215                    220 | 672 |
| gcg gtc acc aat cac aaa aag tgg cag tat aac tcc cct ctg gtc ccg<br>Ala Val Thr Asn His Lys Lys Trp Gln Tyr Asn Ser Pro Leu Val Pro<br>225                    230                    235                240 | 720 |
| cgt aat gct gaa ctt ggg gac cga aaa gga aaa att cac atc ccg ttt<br>Arg Asn Ala Glu Leu Gly Asp Arg Lys Gly Lys Ile His Ile Pro Phe<br>               245                    250                    255 | 768 |
| ccg ctg gca aat gta aca tgc agg gtg cct aaa gca agg aac ccc acc<br>Pro Leu Ala Asn Val Thr Cys Arg Val Pro Lys Ala Arg Asn Pro Thr<br>               260                    265                    270 | 816 |
| gtg acg tac ggg aaa aac caa gtc atc atg cta ctg tat cct gac cac<br>Val Thr Tyr Gly Lys Asn Gln Val Ile Met Leu Leu Tyr Pro Asp His<br>     275                    280                    285 | 864 |
| cca aca ctc ctg tcc tac cgg aat atg gga gaa gaa cca aac tat caa<br>Pro Thr Leu Leu Ser Tyr Arg Asn Met Gly Glu Glu Pro Asn Tyr Gln<br>290                    295                    300 | 912 |
| gaa gag tgg gtg atg cat aag aag gaa gtc gtg cta acc gtg ccg act<br>Glu Glu Trp Val Met His Lys Lys Glu Val Val Leu Thr Val Pro Thr<br>305                    310                    315                320 | 960 |
| gaa ggg ctc gag gtc acg tgg ggc aac aac gag ccg tat aag tat tgg<br>Glu Gly Leu Glu Val Thr Trp Gly Asn Asn Glu Pro Tyr Lys Tyr Trp<br>               325                    330                    335 | 1008 |
| ccg cag tta tct aca aac ggt aca gcc cat ggc cac ccg cat gag ata<br>Pro Gln Leu Ser Thr Asn Gly Thr Ala His Gly His Pro His Glu Ile<br>               340                    345                    350 | 1056 |
| att ctg tat tat tat gag ctg tac ccc act atg act<br>Ile Leu Tyr Tyr Tyr Glu Leu Tyr Pro Thr Met Thr<br>     355                    360 | 1092 |

```
<210> SEQ ID NO 13
<211> LENGTH: 364
<212> TYPE: PRT
<213> ORGANISM: Chikungunya virus

<400> SEQUENCE: 13
```

Asp Asn Phe Asn Val Tyr Lys Ala Thr Arg Pro Tyr Leu Ala His Cys
1                 5                    10                  15

Pro Asp Cys Gly Glu Gly His Ser Cys His Ser Pro Val Ala Leu Glu
              20                    25                    30

Arg Ile Arg Asn Glu Ala Thr Asp Gly Thr Leu Lys Ile Gln Val Ser
          35                    40                    45

Leu Gln Ile Gly Ile Lys Thr Asp Asp Ser His Asp Trp Thr Lys Leu
   50                    55                    60

Arg Tyr Met Asp Asn His Met Pro Ala Asp Ala Glu Arg Ala Gly Leu
65                70                    75                    80

Phe Val Arg Thr Ser Ala Pro Cys Thr Ile Thr Gly Thr Met Gly His
              85                    90                    95

Phe Ile Leu Ala Arg Cys Pro Lys Gly Glu Thr Leu Thr Val Gly Phe
          100                   105                 110

Thr Asp Ser Arg Lys Ile Ser His Ser Cys Thr His Pro Phe His His
        115                    120                   125

Asp Pro Pro Val Ile Gly Arg Glu Lys Phe His Ser Arg Pro Gln His
     130                    135                    140

```
Gly Lys Glu Leu Pro Cys Ser Thr Tyr Val Gln Ser Thr Ala Ala Thr
145                 150                 155                 160

Thr Glu Glu Ile Glu Val His Met Pro Pro Asp Thr Pro Asp Arg Thr
                165                 170                 175

Leu Met Ser Gln Gln Ser Gly Asn Val Lys Ile Thr Val Asn Gly Gln
            180                 185                 190

Thr Val Arg Tyr Lys Cys Asn Cys Gly Gly Ser Asn Glu Gly Leu Thr
        195                 200                 205

Thr Thr Asp Lys Val Ile Asn Asn Cys Lys Val Asp Gln Cys His Ala
    210                 215                 220

Ala Val Thr Asn His Lys Lys Trp Gln Tyr Asn Ser Pro Leu Val Pro
225                 230                 235                 240

Arg Asn Ala Glu Leu Gly Asp Arg Lys Gly Lys Ile His Ile Pro Phe
                245                 250                 255

Pro Leu Ala Asn Val Thr Cys Arg Val Pro Lys Ala Arg Asn Pro Thr
            260                 265                 270

Val Thr Tyr Gly Lys Asn Gln Val Ile Met Leu Leu Tyr Pro Asp His
        275                 280                 285

Pro Thr Leu Leu Ser Tyr Arg Asn Met Gly Glu Glu Pro Asn Tyr Gln
    290                 295                 300

Glu Glu Trp Val Met His Lys Lys Glu Val Val Leu Thr Val Pro Thr
305                 310                 315                 320

Glu Gly Leu Glu Val Thr Trp Gly Asn Asn Glu Pro Tyr Lys Tyr Trp
                325                 330                 335

Pro Gln Leu Ser Thr Asn Gly Thr Ala His Gly His Pro His Glu Ile
            340                 345                 350

Ile Leu Tyr Tyr Tyr Glu Leu Tyr Pro Thr Met Thr
        355                 360

<210> SEQ ID NO 14
<211> LENGTH: 1092
<212> TYPE: DNA
<213> ORGANISM: Chikungunya virus
<220> FEATURE:
<221> NAME/KEY: misc_feature
<223> OTHER INFORMATION: ectodomain glycoprotein E2 strain 06.27
<220> FEATURE:
<221> NAME/KEY: CDS
<222> LOCATION: (1)..(1092)

<400> SEQUENCE: 14 gac aac ttc aat gtc tat aaa gcc aca aga cca tac tta gct cac tgt      48
Asp Asn Phe Asn Val Tyr Lys Ala Thr Arg Pro Tyr Leu Ala His Cys
1               5                   10                  15 ccc gac tgt gga gaa ggg cac tcg tgc cat agt ccc gta gca cta gaa     96
Pro Asp Cys Gly Glu Gly His Ser Cys His Ser Pro Val Ala Leu Glu
            20                  25                  30 cgc atc aga aat gaa gcg aca gac ggg acg ctg aaa atc cag gtc tcc    144
Arg Ile Arg Asn Glu Ala Thr Asp Gly Thr Leu Lys Ile Gln Val Ser
        35                  40                  45 ttg caa atc gga ata aag acg gat gac agc cac gat tgg acc aag ctg    192
Leu Gln Ile Gly Ile Lys Thr Asp Asp Ser His Asp Trp Thr Lys Leu
    50                  55                  60 cgt tat atg gac aac cac atg cca gca gac gca gag agg gcg ggg cta    240
Arg Tyr Met Asp Asn His Met Pro Ala Asp Ala Glu Arg Ala Gly Leu
65                  70                  75                  80 ttt gta aga aca tca gca ccg tgt acg att act gga aca atg gga cac    288
Phe Val Arg Thr Ser Ala Pro Cys Thr Ile Thr Gly Thr Met Gly His
                85                  90                  95
```

```
ttc atc ctg gcc cga tgt cca aaa ggg gaa act ctg acg gtg gga ttc      336
Phe Ile Leu Ala Arg Cys Pro Lys Gly Glu Thr Leu Thr Val Gly Phe
        100                 105                 110 act gac agt agg aag att agt cac tca tgt acg cac cca ttt cac cac      384
Thr Asp Ser Arg Lys Ile Ser His Ser Cys Thr His Pro Phe His His
    115                 120                 125 gac cct cct gtg ata ggt cgg gaa aaa ttc cat tcc cga ccg cag cac      432
Asp Pro Pro Val Ile Gly Arg Glu Lys Phe His Ser Arg Pro Gln His
130                 135                 140 ggt aaa gag cta cct tgc agc acg tac gtg cag agc acc gcc gca act      480
Gly Lys Glu Leu Pro Cys Ser Thr Tyr Val Gln Ser Thr Ala Ala Thr
145                 150                 155                 160 acc gag gag ata gag gta cac atg ccc cca gac acc cct gat cgc aca      528
Thr Glu Glu Ile Glu Val His Met Pro Pro Asp Thr Pro Asp Arg Thr
                165                 170                 175 tta atg tca caa cag tcc ggc aac gta aag atc aca gtc aat ggc cag      576
Leu Met Ser Gln Gln Ser Gly Asn Val Lys Ile Thr Val Asn Gly Gln
            180                 185                 190 acg gtg cgg tac aag tgt aat tgc ggt ggc tca aat gaa gga cta aca      624
Thr Val Arg Tyr Lys Cys Asn Cys Gly Gly Ser Asn Glu Gly Leu Thr
        195                 200                 205 act aca gac aaa gtg att aat aac tgc aag gtt gat caa tgt cat gcc      672
Thr Thr Asp Lys Val Ile Asn Asn Cys Lys Val Asp Gln Cys His Ala
    210                 215                 220 gcg gtc acc aat cac aaa aag tgg cag tat aac tcc cct ctg gtc ccg      720
Ala Val Thr Asn His Lys Lys Trp Gln Tyr Asn Ser Pro Leu Val Pro
225                 230                 235                 240 cgt aat gct gaa ctt ggg gac cga aaa gga aaa att cac atc ccg ttt      768
Arg Asn Ala Glu Leu Gly Asp Arg Lys Gly Lys Ile His Ile Pro Phe
                245                 250                 255 ccg ctg gca aat gta aca tgc agg gtg cct aaa gca agg aac ccc acc      816
Pro Leu Ala Asn Val Thr Cys Arg Val Pro Lys Ala Arg Asn Pro Thr
            260                 265                 270 gtg acg tac ggg aaa aac caa gtc atc atg cta ctg tat cct gac cac      864
Val Thr Tyr Gly Lys Asn Gln Val Ile Met Leu Leu Tyr Pro Asp His
        275                 280                 285 cca aca ctc ctg tcc tac cgg aat atg gga gaa gaa cca aac tat caa      912
Pro Thr Leu Leu Ser Tyr Arg Asn Met Gly Glu Glu Pro Asn Tyr Gln
    290                 295                 300 gaa gag tgg gtg atg cat aag aag gaa gtc gtg cta acc gtg ccg act      960
Glu Glu Trp Val Met His Lys Lys Glu Val Val Leu Thr Val Pro Thr
305                 310                 315                 320 gaa ggg ctc gag gtc acg tgg ggc aac aac gag ccg tat aag tat tgg     1008
Glu Gly Leu Glu Val Thr Trp Gly Asn Asn Glu Pro Tyr Lys Tyr Trp
                325                 330                 335 ccg cag tta tct aca aac ggt aca gcc cat ggc cac ccg cat gag ata     1056
Pro Gln Leu Ser Thr Asn Gly Thr Ala His Gly His Pro His Glu Ile
            340                 345                 350 att ctg tat tat tat gag ctg tac ccc act atg act                     1092
Ile Leu Tyr Tyr Tyr Glu Leu Tyr Pro Thr Met Thr
        355                 360

<210> SEQ ID NO 15
<211> LENGTH: 364
<212> TYPE: PRT
<213> ORGANISM: Chikungunya virus

<400> SEQUENCE: 15

Asp Asn Phe Asn Val Tyr Lys Ala Thr Arg Pro Tyr Leu Ala His Cys
1               5                   10                  15
```

```
Pro Asp Cys Gly Glu Gly His Ser Cys His Ser Pro Val Ala Leu Glu
            20                  25                  30

Arg Ile Arg Asn Glu Ala Thr Asp Gly Thr Leu Lys Ile Gln Val Ser
        35                  40                  45

Leu Gln Ile Gly Ile Lys Thr Asp Ser His Asp Trp Thr Lys Leu
50                  55                  60

Arg Tyr Met Asp Asn His Met Pro Ala Asp Ala Glu Arg Ala Gly Leu
65                  70                  75                  80

Phe Val Arg Thr Ser Ala Pro Cys Thr Ile Thr Gly Thr Met Gly His
                85                  90                  95

Phe Ile Leu Ala Arg Cys Pro Lys Gly Glu Thr Leu Thr Val Gly Phe
            100                 105                 110

Thr Asp Ser Arg Lys Ile Ser His Ser Cys Thr His Pro Phe His His
        115                 120                 125

Asp Pro Pro Val Ile Gly Arg Glu Lys Phe His Ser Arg Pro Gln His
130                 135                 140

Gly Lys Glu Leu Pro Cys Ser Thr Tyr Val Gln Ser Thr Ala Ala Thr
145                 150                 155                 160

Thr Glu Glu Ile Glu Val His Met Pro Pro Asp Thr Pro Asp Arg Thr
                165                 170                 175

Leu Met Ser Gln Gln Ser Gly Asn Val Lys Ile Thr Val Asn Gly Gln
            180                 185                 190

Thr Val Arg Tyr Lys Cys Asn Cys Gly Gly Ser Asn Glu Gly Leu Thr
        195                 200                 205

Thr Thr Asp Lys Val Ile Asn Asn Cys Lys Val Asp Gln Cys His Ala
210                 215                 220

Ala Val Thr Asn His Lys Lys Trp Gln Tyr Asn Ser Pro Leu Val Pro
225                 230                 235                 240

Arg Asn Ala Glu Leu Gly Asp Arg Lys Gly Lys Ile His Ile Pro Phe
                245                 250                 255

Pro Leu Ala Asn Val Thr Cys Arg Val Pro Lys Ala Arg Asn Pro Thr
            260                 265                 270

Val Thr Tyr Gly Lys Asn Gln Val Ile Met Leu Leu Tyr Pro Asp His
        275                 280                 285

Pro Thr Leu Leu Ser Tyr Arg Asn Met Gly Glu Glu Pro Asn Tyr Gln
290                 295                 300

Glu Glu Trp Val Met His Lys Lys Glu Val Val Leu Thr Val Pro Thr
305                 310                 315                 320

Glu Gly Leu Glu Val Thr Trp Gly Asn Asn Glu Pro Tyr Lys Tyr Trp
                325                 330                 335

Pro Gln Leu Ser Thr Asn Gly Thr Ala His Gly His Pro His Glu Ile
            340                 345                 350

Ile Leu Tyr Tyr Tyr Glu Leu Tyr Pro Thr Met Thr
        355                 360

<210> SEQ ID NO 16
<211> LENGTH: 2772
<212> TYPE: DNA
<213> ORGANISM: Artificial Sequence
<220> FEATURE:
<223> OTHER INFORMATION: polyprotein E2-6K-E1 France/2010 CHIKV strains
      (GenBank: CCA61130.1)
<220> FEATURE:
<221> NAME/KEY: CDS
<222> LOCATION: (1)..(2772)
```

-continued

<400> SEQUENCE: 16

| | | | | | | | | | | | | | | | | |
|---|---|---|---|---|---|---|---|---|---|---|---|---|---|---|---|---|
| agc | acc | aag | gac | aac | ttc | aat | gtc | tat | aaa | gcc | aca | aga | cca | tac | tta | 48 |
| Ser | Thr | Lys | Asp | Asn | Phe | Asn | Val | Tyr | Lys | Ala | Thr | Arg | Pro | Tyr | Leu | |
| 1 | | | | 5 | | | | | 10 | | | | | 15 | | |
| gct | cac | tgt | ccc | gac | tgt | gga | gaa | ggg | cac | tcg | tgc | cat | agt | ccc | gta | 96 |
| Ala | His | Cys | Pro | Asp | Cys | Gly | Glu | Gly | His | Ser | Cys | His | Ser | Pro | Val | |
| | | | 20 | | | | | 25 | | | | | 30 | | | |
| gca | cta | gaa | cgc | atc | aga | aat | gaa | gcg | aca | gac | ggg | acg | ctg | aaa | atc | 144 |
| Ala | Leu | Glu | Arg | Ile | Arg | Asn | Glu | Ala | Thr | Asp | Gly | Thr | Leu | Lys | Ile | |
| | | 35 | | | | | 40 | | | | | 45 | | | | |
| cag | gtc | tcc | ttg | caa | atc | gga | ata | aag | acg | gat | gac | agc | cac | gat | tgg | 192 |
| Gln | Val | Ser | Leu | Gln | Ile | Gly | Ile | Lys | Thr | Asp | Asp | Ser | His | Asp | Trp | |
| 50 | | | | | 55 | | | | | 60 | | | | | | |
| acc | aag | ctg | cgt | tat | atg | gac | aac | cac | atg | cca | gca | gac | gca | gag | agg | 240 |
| Thr | Lys | Leu | Arg | Tyr | Met | Asp | Asn | His | Met | Pro | Ala | Asp | Ala | Glu | Arg | |
| 65 | | | | | 70 | | | | | 75 | | | | | 80 | |
| gcg | ggg | cta | ttt | gta | aga | aca | tca | gca | ccg | tgt | acg | att | act | gga | aca | 288 |
| Ala | Gly | Leu | Phe | Val | Arg | Thr | Ser | Ala | Pro | Cys | Thr | Ile | Thr | Gly | Thr | |
| | | | | 85 | | | | | 90 | | | | | 95 | | |
| atg | gga | cac | ttc | atc | ctg | gcc | cga | tgt | cca | aaa | ggg | gaa | act | ctg | acg | 336 |
| Met | Gly | His | Phe | Ile | Leu | Ala | Arg | Cys | Pro | Lys | Gly | Glu | Thr | Leu | Thr | |
| | | | 100 | | | | | 105 | | | | | 110 | | | |
| gtg | gga | ttc | act | gac | agt | agg | aag | att | agt | cat | tca | tgt | acg | cac | cca | 384 |
| Val | Gly | Phe | Thr | Asp | Ser | Arg | Lys | Ile | Ser | His | Ser | Cys | Thr | His | Pro | |
| | | 115 | | | | | 120 | | | | | 125 | | | | |
| ttt | cac | cac | gac | cct | cct | gtg | ata | ggt | cgg | gaa | aaa | ttc | cat | tcc | cga | 432 |
| Phe | His | His | Asp | Pro | Pro | Val | Ile | Gly | Arg | Glu | Lys | Phe | His | Ser | Arg | |
| 130 | | | | | 135 | | | | | 140 | | | | | | |
| ccg | cag | cac | ggt | aaa | gag | cta | cct | tgc | agc | acg | tac | gtg | cag | agc | acc | 480 |
| Pro | Gln | His | Gly | Lys | Glu | Leu | Pro | Cys | Ser | Thr | Tyr | Val | Gln | Ser | Thr | |
| 145 | | | | | 150 | | | | | 155 | | | | | 160 | |
| gcc | gca | act | acc | gag | gag | ata | gag | gta | cac | atg | ccc | cca | gac | acc | cct | 528 |
| Ala | Ala | Thr | Thr | Glu | Glu | Ile | Glu | Val | His | Met | Pro | Pro | Asp | Thr | Pro | |
| | | | | 165 | | | | | 170 | | | | | 175 | | |
| gat | cgc | aca | tta | atg | tca | caa | cag | tcc | ggc | aac | gta | aag | atc | aca | gtc | 576 |
| Asp | Arg | Thr | Leu | Met | Ser | Gln | Gln | Ser | Gly | Asn | Val | Lys | Ile | Thr | Val | |
| | | | 180 | | | | | 185 | | | | | 190 | | | |
| aat | ggc | cag | acg | gtg | cgg | tat | aag | tgt | aat | tgc | ggt | ggc | tca | aat | gaa | 624 |
| Asn | Gly | Gln | Thr | Val | Arg | Tyr | Lys | Cys | Asn | Cys | Gly | Gly | Ser | Asn | Glu | |
| | | 195 | | | | | 200 | | | | | 205 | | | | |
| gga | cta | aca | act | aca | gac | aaa | gtg | att | aat | aac | tgc | aag | gtt | gat | caa | 672 |
| Gly | Leu | Thr | Thr | Thr | Asp | Lys | Val | Ile | Asn | Asn | Cys | Lys | Val | Asp | Gln | |
| | 210 | | | | | 215 | | | | | 220 | | | | | |
| tgt | cat | gcc | gcg | gtc | acc | aat | cac | aaa | aag | tgg | cag | tat | aac | tcc | cct | 720 |
| Cys | His | Ala | Ala | Val | Thr | Asn | His | Lys | Lys | Trp | Gln | Tyr | Asn | Ser | Pro | |
| 225 | | | | | 230 | | | | | 235 | | | | | 240 | |
| ctg | gtc | ccg | cgt | aat | gct | gaa | ctt | ggg | gac | cga | caa | gga | aaa | att | cac | 768 |
| Leu | Val | Pro | Arg | Asn | Ala | Glu | Leu | Gly | Asp | Arg | Gln | Gly | Lys | Ile | His | |
| | | | | 245 | | | | | 250 | | | | | 255 | | |
| atc | ccg | ttt | ccg | ctg | gca | aat | gta | aca | tgc | agg | gtg | cct | aaa | gca | agg | 816 |
| Ile | Pro | Phe | Pro | Leu | Ala | Asn | Val | Thr | Cys | Arg | Val | Pro | Lys | Ala | Arg | |
| | | | 260 | | | | | 265 | | | | | 270 | | | |
| aac | ccc | acc | gtg | acg | tac | ggg | aaa | aac | caa | gtc | atc | atg | cta | ctg | tat | 864 |
| Asn | Pro | Thr | Val | Thr | Tyr | Gly | Lys | Asn | Gln | Val | Ile | Met | Leu | Leu | Tyr | |
| | | 275 | | | | | 280 | | | | | 285 | | | | |
| cct | gac | cac | cca | aca | ctc | ctg | tcc | tac | cgg | aat | atg | gga | gaa | gaa | cca | 912 |
| Pro | Asp | His | Pro | Thr | Leu | Leu | Ser | Tyr | Arg | Asn | Met | Gly | Glu | Glu | Pro | |
| | 290 | | | | | 295 | | | | | 300 | | | | | |
| aac | tat | caa | gaa | gag | tgg | gtg | atg | cat | aag | aag | gaa | gtc | gtg | cta | acc | 960 |

```
Asn Tyr Gln Glu Glu Trp Val Met His Lys Lys Glu Val Val Leu Thr
305                 310                 315                 320 gtg ccg act gaa ggg ctc gag gtc acg tgg ggc aac aac gag ccg tat       1008
Val Pro Thr Glu Gly Leu Glu Val Thr Trp Gly Asn Asn Glu Pro Tyr
                325                 330                 335 aag tat tgg ccg cag tta tct aca aac ggt aca gcc cat ggc cac ccg       1056
Lys Tyr Trp Pro Gln Leu Ser Thr Asn Gly Thr Ala His Gly His Pro
            340                 345                 350 cat gag ata att ctg tat tat tat gag ctg tac cct act atg act gta       1104
His Glu Ile Ile Leu Tyr Tyr Tyr Glu Leu Tyr Pro Thr Met Thr Val
        355                 360                 365 gta gtt gta tca gtg gcc acg ttc ata ctc ctg tca atg gtg ggt atg       1152
Val Val Val Ser Val Ala Thr Phe Ile Leu Leu Ser Met Val Gly Met
370                 375                 380 gca gcg ggg atg tgc atg tgt gca cga cgc aga tgc atc aca ccg tat       1200
Ala Ala Gly Met Cys Met Cys Ala Arg Arg Arg Cys Ile Thr Pro Tyr
385                 390                 395                 400 gaa ctg aca cca gga gct acc gtc cct ttc ctg ctt agc cta ata tgc       1248
Glu Leu Thr Pro Gly Ala Thr Val Pro Phe Leu Leu Ser Leu Ile Cys
                405                 410                 415 tgc atc aga aca gct aaa gcg gcc aca tac caa gag gct gcg ata tac       1296
Cys Ile Arg Thr Ala Lys Ala Ala Thr Tyr Gln Glu Ala Ala Ile Tyr
            420                 425                 430 ctg tgg aac gag cag caa cct ttg ttt tgg cta caa gcc ctt att ccg       1344
Leu Trp Asn Glu Gln Gln Pro Leu Phe Trp Leu Gln Ala Leu Ile Pro
        435                 440                 445 ctg gca gcc ctg att gtt cta tgc aac tgt ctg aga ctc tta cca tgc       1392
Leu Ala Ala Leu Ile Val Leu Cys Asn Cys Leu Arg Leu Leu Pro Cys
450                 455                 460 tgc tgt aaa acg ttg gct ttt tta gcc gta atg agc gtc ggt gcc cac       1440
Cys Cys Lys Thr Leu Ala Phe Leu Ala Val Met Ser Val Gly Ala His
465                 470                 475                 480 act gtg agc gcg tac gaa cac gta aca gtg atc ccg aac acg gtg gga       1488
Thr Val Ser Ala Tyr Glu His Val Thr Val Ile Pro Asn Thr Val Gly
                485                 490                 495 gta ccg tat aag act cta gtc aat aga cct ggc tac agc ccc atg gta       1536
Val Pro Tyr Lys Thr Leu Val Asn Arg Pro Gly Tyr Ser Pro Met Val
            500                 505                 510 ttg gag atg gaa cta ctg tca gtc act ttg gag cca aca cta tcg ctt       1584
Leu Glu Met Glu Leu Leu Ser Val Thr Leu Glu Pro Thr Leu Ser Leu
        515                 520                 525 gat tac atc acg tgc gag tac aaa acc gtc atc ccg tct ccg tac gtg       1632
Asp Tyr Ile Thr Cys Glu Tyr Lys Thr Val Ile Pro Ser Pro Tyr Val
530                 535                 540 aag tgc tgc ggt aca gca gag tgc aag gac aaa aac cta cct gac tac       1680
Lys Cys Cys Gly Thr Ala Glu Cys Lys Asp Lys Asn Leu Pro Asp Tyr
545                 550                 555                 560 agc tgt aag gtc ttc acc ggc gtc tac cca ttt atg tgg ggc ggc gcc       1728
Ser Cys Lys Val Phe Thr Gly Val Tyr Pro Phe Met Trp Gly Gly Ala
                565                 570                 575 tac tgc ttc tgc gac gct gaa aat acg cag ttg agc gaa gca cat gtg       1776
Tyr Cys Phe Cys Asp Ala Glu Asn Thr Gln Leu Ser Glu Ala His Val
            580                 585                 590 gag aag tcc gaa tca tgc aaa aca gaa ttt gca tca gcg tac agg gct       1824
Glu Lys Ser Glu Ser Cys Lys Thr Glu Phe Ala Ser Ala Tyr Arg Ala
        595                 600                 605 cat acc gca tct gca tca gct aag ctc cgc gtc ctt tac caa gga aat       1872
His Thr Ala Ser Ala Ser Ala Lys Leu Arg Val Leu Tyr Gln Gly Asn
610                 615                 620
```

```
aac atc act gta act gcc tat gca aac ggc gac cat gcc gtc aca gtt    1920
Asn Ile Thr Val Thr Ala Tyr Ala Asn Gly Asp His Ala Val Thr Val
625                 630                 635                 640 aag gac gcc aaa ttc att gtg ggg cca atg tct tca gcc tgg aca cct    1968
Lys Asp Ala Lys Phe Ile Val Gly Pro Met Ser Ser Ala Trp Thr Pro
            645                 650                 655 ttc gac aac aaa att gtg gtg tac aaa ggt gac gtc tat aac atg gac    2016
Phe Asp Asn Lys Ile Val Val Tyr Lys Gly Asp Val Tyr Asn Met Asp
                660                 665                 670 tac ccg ccc ttt ggc gca gga aga cca gga caa ttt ggc gat atc caa    2064
Tyr Pro Pro Phe Gly Ala Gly Arg Pro Gly Gln Phe Gly Asp Ile Gln
            675                 680                 685 agt cgc aca cct gag agt aaa gac gtc tat gct aat aca caa ctg gta    2112
Ser Arg Thr Pro Glu Ser Lys Asp Val Tyr Ala Asn Thr Gln Leu Val
690                 695                 700 ctg cag aga ccg gct gtg ggt acg gta cac gtg cca tac tct cag gca    2160
Leu Gln Arg Pro Ala Val Gly Thr Val His Val Pro Tyr Ser Gln Ala
705                 710                 715                 720 cca tct ggc ttt aag tat tgg cta aaa gaa cgc ggg gcg tca ctg cag    2208
Pro Ser Gly Phe Lys Tyr Trp Leu Lys Glu Arg Gly Ala Ser Leu Gln
            725                 730                 735 cac aca gca cca ttt ggc tgc caa ata gca aca aac ccg gta aga gcg    2256
His Thr Ala Pro Phe Gly Cys Gln Ile Ala Thr Asn Pro Val Arg Ala
                740                 745                 750 gtg aac tgc gcc gta ggg aac atg ccc atc tcc atc gac ata ccg gaa    2304
Val Asn Cys Ala Val Gly Asn Met Pro Ile Ser Ile Asp Ile Pro Glu
            755                 760                 765 gcg gcc ttc act agg gtc gtc gac gcg ccc tct tta acg gac atg tcg    2352
Ala Ala Phe Thr Arg Val Val Asp Ala Pro Ser Leu Thr Asp Met Ser
770                 775                 780 tgc gag gta cca gcc tgc acc cat tcc tca gac ttt ggg ggc gtc gcc    2400
Cys Glu Val Pro Ala Cys Thr His Ser Ser Asp Phe Gly Gly Val Ala
785                 790                 795                 800 att att aaa tat gca gcc agc aag aaa ggc aag tgt gcg gtg cat tcg    2448
Ile Ile Lys Tyr Ala Ala Ser Lys Lys Gly Lys Cys Ala Val His Ser
            805                 810                 815 atg act aac gcc gtc act att cgg gaa gct gag ata gaa gtt gaa ggg    2496
Met Thr Asn Ala Val Thr Ile Arg Glu Ala Glu Ile Glu Val Glu Gly
                820                 825                 830 aat tct cag ctg caa atc tct ttc tcg acg gcc tta gcc agc gcc gaa    2544
Asn Ser Gln Leu Gln Ile Ser Phe Ser Thr Ala Leu Ala Ser Ala Glu
            835                 840                 845 ttc cgc gta caa gtc tgt tct aca caa gta cac tgt gca gct gag tgc    2592
Phe Arg Val Gln Val Cys Ser Thr Gln Val His Cys Ala Ala Glu Cys
850                 855                 860 cac ccc ccg aag gac cac ata gtc aac tac ccg gcg tca cat acc acc    2640
His Pro Pro Lys Asp His Ile Val Asn Tyr Pro Ala Ser His Thr Thr
865                 870                 875                 880 ctc ggg gtc cag gac atc tcc gct acg gcg atg tca tgg gtg cag aag    2688
Leu Gly Val Gln Asp Ile Ser Ala Thr Ala Met Ser Trp Val Gln Lys
            885                 890                 895 atc acg gga ggt gtg gga ctg gtt gtt gct gtt gcc gca ctg att cta    2736
Ile Thr Gly Gly Val Gly Leu Val Val Ala Val Ala Ala Leu Ile Leu
                900                 905                 910 atc gtg gtg cta tgc gtg tcg ttc agc agg cac taa                    2772
Ile Val Val Leu Cys Val Ser Phe Ser Arg His
            915                 920

<210> SEQ ID NO 17
<211> LENGTH: 923
```

```
<212> TYPE: PRT
<213> ORGANISM: Artificial Sequence
<220> FEATURE:
<223> OTHER INFORMATION: Synthetic Construct

<400> SEQUENCE: 17
```

| | | | | | | | | | | | | | | | |
|---|---|---|---|---|---|---|---|---|---|---|---|---|---|---|---|
| Ser | Thr | Lys | Asp | Asn | Phe | Asn | Val | Tyr | Lys | Ala | Thr | Arg | Pro | Tyr | Leu |
| 1 | | | | 5 | | | | | 10 | | | | | 15 | |
| Ala | His | Cys | Pro | Asp | Cys | Gly | Glu | Gly | His | Ser | Cys | His | Ser | Pro | Val |
| | | | 20 | | | | | 25 | | | | | 30 | | |
| Ala | Leu | Glu | Arg | Ile | Arg | Asn | Glu | Ala | Thr | Asp | Gly | Thr | Leu | Lys | Ile |
| | | 35 | | | | | 40 | | | | | 45 | | | |
| Gln | Val | Ser | Leu | Gln | Ile | Gly | Ile | Lys | Thr | Asp | Ser | His | Asp | Trp | |
| | 50 | | | | | 55 | | | | | 60 | | | | |
| Thr | Lys | Leu | Arg | Tyr | Met | Asp | Asn | His | Met | Pro | Ala | Asp | Ala | Glu | Arg |
| 65 | | | | | 70 | | | | | 75 | | | | | 80 |
| Ala | Gly | Leu | Phe | Val | Arg | Thr | Ser | Ala | Pro | Cys | Thr | Ile | Thr | Gly | Thr |
| | | | | 85 | | | | | 90 | | | | | 95 | |
| Met | Gly | His | Phe | Ile | Leu | Ala | Arg | Cys | Pro | Lys | Gly | Glu | Thr | Leu | Thr |
| | | | 100 | | | | | 105 | | | | | 110 | | |
| Val | Gly | Phe | Thr | Asp | Ser | Arg | Lys | Ile | Ser | His | Ser | Cys | Thr | His | Pro |
| | | 115 | | | | | 120 | | | | | 125 | | | |
| Phe | His | His | Asp | Pro | Pro | Val | Ile | Gly | Arg | Glu | Lys | Phe | His | Ser | Arg |
| | 130 | | | | | 135 | | | | | 140 | | | | |
| Pro | Gln | His | Gly | Lys | Glu | Leu | Pro | Cys | Ser | Thr | Tyr | Val | Gln | Ser | Thr |
| 145 | | | | | 150 | | | | | 155 | | | | | 160 |
| Ala | Ala | Thr | Thr | Glu | Glu | Ile | Glu | Val | His | Met | Pro | Pro | Asp | Thr | Pro |
| | | | | 165 | | | | | 170 | | | | | 175 | |
| Asp | Arg | Thr | Leu | Met | Ser | Gln | Gln | Ser | Gly | Asn | Val | Lys | Ile | Thr | Val |
| | | | 180 | | | | | 185 | | | | | 190 | | |
| Asn | Gly | Gln | Thr | Val | Arg | Tyr | Lys | Cys | Asn | Cys | Gly | Gly | Ser | Asn | Glu |
| | | 195 | | | | | 200 | | | | | 205 | | | |
| Gly | Leu | Thr | Thr | Thr | Asp | Lys | Val | Ile | Asn | Asn | Cys | Lys | Val | Asp | Gln |
| | 210 | | | | | 215 | | | | | 220 | | | | |
| Cys | His | Ala | Ala | Val | Thr | Asn | His | Lys | Lys | Trp | Gln | Tyr | Asn | Ser | Pro |
| 225 | | | | | 230 | | | | | 235 | | | | | 240 |
| Leu | Val | Pro | Arg | Asn | Ala | Glu | Leu | Gly | Asp | Arg | Gln | Gly | Lys | Ile | His |
| | | | | 245 | | | | | 250 | | | | | 255 | |
| Ile | Pro | Phe | Pro | Leu | Ala | Asn | Val | Thr | Cys | Arg | Val | Pro | Lys | Ala | Arg |
| | | | 260 | | | | | 265 | | | | | 270 | | |
| Asn | Pro | Thr | Val | Thr | Tyr | Gly | Lys | Asn | Gln | Val | Ile | Met | Leu | Leu | Tyr |
| | | 275 | | | | | 280 | | | | | 285 | | | |
| Pro | Asp | His | Pro | Thr | Leu | Leu | Ser | Tyr | Arg | Asn | Met | Gly | Glu | Glu | Pro |
| | 290 | | | | | 295 | | | | | 300 | | | | |
| Asn | Tyr | Gln | Glu | Glu | Trp | Val | Met | His | Lys | Lys | Glu | Val | Val | Leu | Thr |
| 305 | | | | | 310 | | | | | 315 | | | | | 320 |
| Val | Pro | Thr | Glu | Gly | Leu | Glu | Val | Thr | Trp | Gly | Asn | Asn | Glu | Pro | Tyr |
| | | | | 325 | | | | | 330 | | | | | 335 | |
| Lys | Tyr | Trp | Pro | Gln | Leu | Ser | Thr | Asn | Gly | Thr | Ala | His | Gly | His | Pro |
| | | | 340 | | | | | 345 | | | | | 350 | | |
| His | Glu | Ile | Ile | Leu | Tyr | Tyr | Tyr | Glu | Leu | Tyr | Pro | Thr | Met | Thr | Val |
| | | 355 | | | | | 360 | | | | | 365 | | | |
| Val | Val | Val | Ser | Val | Ala | Thr | Phe | Ile | Leu | Leu | Ser | Met | Val | Gly | Met |
| | 370 | | | | | 375 | | | | | 380 | | | | |

```
Ala Ala Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
            405                 410                 415

Cys Ile Arg Thr Ala Lys Ala Ala Thr Tyr Gln Glu Ala Ala Ile Tyr
        420                 425                 430

Leu Trp Asn Glu Gln Gln Pro Leu Phe Trp Leu Gln Ala Leu Ile Pro
    435                 440                 445

Leu Ala Ala Leu Ile Val Leu Cys Asn Cys Leu Arg Leu Leu Pro Cys
450                 455                 460

Cys Cys Lys Thr Leu Ala Phe Leu Ala Val Met Ser Val Gly Ala His
465                 470                 475                 480

Thr Val Ser Ala Tyr Glu His Val Thr Val Ile Pro Asn Thr Val Gly
            485                 490                 495

Val Pro Tyr Lys Thr Leu Val Asn Arg Pro Gly Tyr Ser Pro Met Val
        500                 505                 510

Leu Glu Met Glu Leu Leu Ser Val Thr Leu Pro Thr Leu Ser Leu
    515                 520                 525

Asp Tyr Ile Thr Cys Glu Tyr Lys Thr Val Ile Pro Ser Pro Tyr Val
530                 535                 540

Lys Cys Cys Gly Thr Ala Glu Cys Lys Asp Lys Asn Leu Pro Asp Tyr
545                 550                 555                 560

Ser Cys Lys Val Phe Thr Gly Val Tyr Pro Phe Met Trp Gly Gly Ala
            565                 570                 575

Tyr Cys Phe Cys Asp Ala Glu Asn Thr Gln Leu Ser Glu Ala His Val
        580                 585                 590

Glu Lys Ser Glu Ser Cys Lys Thr Glu Phe Ala Ser Ala Tyr Arg Ala
    595                 600                 605

His Thr Ala Ser Ala Ser Ala Lys Leu Arg Val Leu Tyr Gln Gly Asn
610                 615                 620

Asn Ile Thr Val Thr Ala Tyr Ala Asn Gly Asp His Ala Val Thr Val
625                 630                 635                 640

Lys Asp Ala Lys Phe Ile Val Gly Pro Met Ser Ser Ala Trp Thr Pro
            645                 650                 655

Phe Asp Asn Lys Ile Val Val Tyr Lys Gly Asp Val Tyr Asn Met Asp
        660                 665                 670

Tyr Pro Pro Phe Gly Ala Gly Arg Pro Gly Gln Phe Gly Asp Ile Gln
    675                 680                 685

Ser Arg Thr Pro Glu Ser Lys Asp Val Tyr Ala Asn Thr Gln Leu Val
690                 695                 700

Leu Gln Arg Pro Ala Val Gly Thr Val His Val Pro Tyr Ser Gln Ala
705                 710                 715                 720

Pro Ser Gly Phe Lys Tyr Trp Leu Lys Glu Arg Gly Ala Ser Leu Gln
            725                 730                 735

His Thr Ala Pro Phe Gly Cys Gln Ile Ala Thr Asn Pro Val Arg Ala
        740                 745                 750

Val Asn Cys Ala Val Gly Asn Met Pro Ile Ser Ile Asp Ile Pro Glu
    755                 760                 765

Ala Ala Phe Thr Arg Val Val Asp Ala Pro Ser Leu Thr Asp Met Ser
770                 775                 780

Cys Glu Val Pro Ala Cys Thr His Ser Ser Asp Phe Gly Gly Val Ala
785                 790                 795                 800

Ile Ile Lys Tyr Ala Ala Ser Lys Lys Gly Lys Cys Ala Val His Ser
```

```
                            805                 810                 815
Met Thr Asn Ala Val Thr Ile Arg Glu Ala Glu Ile Glu Val Glu Gly
                820                 825                 830

Asn Ser Gln Leu Gln Ile Ser Phe Ser Thr Ala Leu Ala Ser Ala Glu
            835                 840                 845

Phe Arg Val Gln Val Cys Ser Thr Gln Val His Cys Ala Ala Glu Cys
        850                 855                 860

His Pro Pro Lys Asp His Ile Val Asn Tyr Pro Ala Ser His Thr Thr
865                 870                 875                 880

Leu Gly Val Gln Asp Ile Ser Ala Thr Ala Met Ser Trp Val Gln Lys
                885                 890                 895

Ile Thr Gly Gly Val Gly Leu Val Val Ala Val Ala Ala Leu Ile Leu
            900                 905                 910

Ile Val Val Leu Cys Val Ser Phe Ser Arg His
        915                 920

<210> SEQ ID NO 18
<211> LENGTH: 2772
<212> TYPE: DNA
<213> ORGANISM: Artificial Sequence
<220> FEATURE:
<223> OTHER INFORMATION: polyprotein E2-6K-E1 France/2010 CHIKV strains
      (GenBank: CCA61131.1)
<220> FEATURE:
<221> NAME/KEY: CDS
<222> LOCATION: (1)..(2772)

<400> SEQUENCE: 18 agt att aag gac cac ttc aat gtc tat aaa gcc aca aga ccg tac cta      48
Ser Ile Lys Asp His Phe Asn Val Tyr Lys Ala Thr Arg Pro Tyr Leu
1               5                   10                  15 gct cac tgt ccc gac tgt gga gaa ggg cac tcg tgc cat agt ccc gta      96
Ala His Cys Pro Asp Cys Gly Glu Gly His Ser Cys His Ser Pro Val
                20                  25                  30 gcg cta gaa cgc atc aga aac gaa gcg aca gac ggg acg ttg aaa atc     144
Ala Leu Glu Arg Ile Arg Asn Glu Ala Thr Asp Gly Thr Leu Lys Ile
            35                  40                  45 cag gtt tcc ttg caa atc gga ata aag acg gat gat agc cat gat tgg     192
Gln Val Ser Leu Gln Ile Gly Ile Lys Thr Asp Asp Ser His Asp Trp
        50                  55                  60 acc aag ctg cgt tat atg gac aat cac atg cca gca gac gca gag cgg     240
Thr Lys Leu Arg Tyr Met Asp Asn His Met Pro Ala Asp Ala Glu Arg
65                  70                  75                  80 gcc ggg cta ttt gta aga acg tca gca ccg tgc acg att act gga aca     288
Ala Gly Leu Phe Val Arg Thr Ser Ala Pro Cys Thr Ile Thr Gly Thr
                85                  90                  95 atg gga cac ttc att ctg gcc cga tgt ccg aaa gga gaa act ctg aca     336
Met Gly His Phe Ile Leu Ala Arg Cys Pro Lys Gly Glu Thr Leu Thr
                100                 105                 110 gtg ggg ttc act gac ggt agg aag atc agt cac tca tgt acg cac cca     384
Val Gly Phe Thr Asp Gly Arg Lys Ile Ser His Ser Cys Thr His Pro
            115                 120                 125 ttt cac cat gac cct cct gtg ata ggc cgg gaa aaa ttc cat tcc cga     432
Phe His His Asp Pro Pro Val Ile Gly Arg Glu Lys Phe His Ser Arg
        130                 135                 140 ccg cag cac ggt agg gaa cta cct tgc agc acg tac gcg cag agc acc     480
Pro Gln His Gly Arg Glu Leu Pro Cys Ser Thr Tyr Ala Gln Ser Thr
145                 150                 155                 160 gct gca act gcc gag gag ata gag gta cat atg ccc cca gac act cca     528
Ala Ala Thr Ala Glu Glu Ile Glu Val His Met Pro Pro Asp Thr Pro
```

```
             165                 170                 175
gat cgc aca tta atg tca caa cag tcc ggc aat gta aag atc aca gtc     576
Asp Arg Thr Leu Met Ser Gln Gln Ser Gly Asn Val Lys Ile Thr Val
            180                 185                 190 aat agt cag acg gtg cgg tac aag tgc aat tgt ggt gac tca agt gaa     624
Asn Ser Gln Thr Val Arg Tyr Lys Cys Asn Cys Gly Asp Ser Ser Glu
        195                 200                 205 gga tta acc act aca gat aaa gtg att aat aac tgc aag gtt gat caa     672
Gly Leu Thr Thr Thr Asp Lys Val Ile Asn Asn Cys Lys Val Asp Gln
    210                 215                 220 tgc cat gcc gcg gtc acc aat cac aaa aaa tgg cag tat aat tcc cct     720
Cys His Ala Ala Val Thr Asn His Lys Lys Trp Gln Tyr Asn Ser Pro
225                 230                 235                 240 ctg gtc ccg cgc aat gct gaa ttc ggg gac cgg aaa gga aaa gtt cac     768
Leu Val Pro Arg Asn Ala Glu Phe Gly Asp Arg Lys Gly Lys Val His
                245                 250                 255 att cca ttt cct ctg gca aat gtg aca tgc agg gtg cct aaa gca aga     816
Ile Pro Phe Pro Leu Ala Asn Val Thr Cys Arg Val Pro Lys Ala Arg
            260                 265                 270 aac ccc acc gtg acg tac gga aaa aac caa gtc atc atg ttg ctg tat     864
Asn Pro Thr Val Thr Tyr Gly Lys Asn Gln Val Ile Met Leu Leu Tyr
        275                 280                 285 ccg gac cac cca acg ctc ctg tcc tac agg aat atg gga gaa gaa cca     912
Pro Asp His Pro Thr Leu Leu Ser Tyr Arg Asn Met Gly Glu Glu Pro
    290                 295                 300 aac tat caa gaa gag tgg gtg acg cat aag aag gag atc agg tta acc     960
Asn Tyr Gln Glu Glu Trp Val Thr His Lys Lys Glu Ile Arg Leu Thr
305                 310                 315                 320 gta ccg act gaa ggg ctc gag gtc acg tgg ggt aac aat gag ccg tac    1008
Val Pro Thr Glu Gly Leu Glu Val Thr Trp Gly Asn Asn Glu Pro Tyr
                325                 330                 335 aag tat tgg ccg cag tta tcc aca aac ggt aca gcc cac ggc cac ccg    1056
Lys Tyr Trp Pro Gln Leu Ser Thr Asn Gly Thr Ala His Gly His Pro
            340                 345                 350 cat gag ata att ttg tat tat tat gag ctg tac cca act atg act gtg    1104
His Glu Ile Ile Leu Tyr Tyr Tyr Glu Leu Tyr Pro Thr Met Thr Val
        355                 360                 365 gta gtt ttg tca gtg gcc tcg ttc ata ctc ctg tcg atg gtg ggt gtg    1152
Val Val Leu Ser Val Ala Ser Phe Ile Leu Leu Ser Met Val Gly Val
    370                 375                 380 gca gtg ggg atg tgc atg tgt gca cga cgc aga tgc att aca ccg tac    1200
Ala Val Gly Met Cys Met Cys Ala Arg Arg Arg Cys Ile Thr Pro Tyr
385                 390                 395                 400 gaa ctg aca cca gga gct acc gtc cct ttc ctg ctt agc cta ata tgc    1248
Glu Leu Thr Pro Gly Ala Thr Val Pro Phe Leu Leu Ser Leu Ile Cys
                405                 410                 415 tgc att aga aca gct aaa gcg gcc aca tac cag gag gcc gcg gta tac    1296
Cys Ile Arg Thr Ala Lys Ala Ala Thr Tyr Gln Glu Ala Ala Val Tyr
            420                 425                 430 ctg tgg aac gag cag cag cct tta ttt tgg ctg caa gcc ctt att ccg    1344
Leu Trp Asn Glu Gln Gln Pro Leu Phe Trp Leu Gln Ala Leu Ile Pro
        435                 440                 445 ctg gca gcc ctg att gtc cta tgt aac tgt ctg aga ctc tta cca tgc    1392
Leu Ala Ala Leu Ile Val Leu Cys Asn Cys Leu Arg Leu Leu Pro Cys
    450                 455                 460 tgt tgt aaa atg ttg act ttt tta gcc gta ctg agc gtc ggt gcc cac    1440
Cys Cys Lys Met Leu Thr Phe Leu Ala Val Leu Ser Val Gly Ala His
465                 470                 475                 480 act gtg agc gcg tac gaa cac gta aca gtg atc ccg aac acg gtg gga    1488
```

-continued

```
Thr Val Ser Ala Tyr Glu His Val Thr Val Ile Pro Asn Thr Val Gly
                485                 490                 495 gta ccg tat aag act cta gtc aac aga ccg ggc tac agc ccc atg gta    1536
Val Pro Tyr Lys Thr Leu Val Asn Arg Pro Gly Tyr Ser Pro Met Val
        500                 505                 510 ctg gag atg gag ctt ctg tct gtc acc ttg gaa cca acg cta tcg ctt    1584
Leu Glu Met Glu Leu Leu Ser Val Thr Leu Glu Pro Thr Leu Ser Leu
            515                 520                 525 gat tac atc acg tgc gag tat aaa acc gtt atc ccg tct ccg tac gtg    1632
Asp Tyr Ile Thr Cys Glu Tyr Lys Thr Val Ile Pro Ser Pro Tyr Val
530                 535                 540 aaa tgc tgc ggt aca gca gag tgt aag gac aag agc cta cct gat tac    1680
Lys Cys Cys Gly Thr Ala Glu Cys Lys Asp Lys Ser Leu Pro Asp Tyr
545                 550                 555                 560 agc tgt aag gtc ttc acc ggc gtc tac cca ttc atg tgg ggc ggc gcc    1728
Ser Cys Lys Val Phe Thr Gly Val Tyr Pro Phe Met Trp Gly Gly Ala
                565                 570                 575 tac tgc ttc tgc gac acc gaa aat acg caa ttg agc gaa gca cat gtg    1776
Tyr Cys Phe Cys Asp Thr Glu Asn Thr Gln Leu Ser Glu Ala His Val
            580                 585                 590 gag aag tcc gaa tca tgc aaa aca gaa ttt gca tca gca tac agg gct    1824
Glu Lys Ser Glu Ser Cys Lys Thr Glu Phe Ala Ser Ala Tyr Arg Ala
            595                 600                 605 cat acc gca tcc gca tca gct aag ctc cgc gtc ctt tac caa gga aat    1872
His Thr Ala Ser Ala Ser Ala Lys Leu Arg Val Leu Tyr Gln Gly Asn
        610                 615                 620 aat atc act gta gct gct tat gca aac ggc gac cat gcc gtc aca gtt    1920
Asn Ile Thr Val Ala Ala Tyr Ala Asn Gly Asp His Ala Val Thr Val
625                 630                 635                 640 aag gac gct aaa ttc ata gtg ggg cca atg tct tca gcc tgg aca cct    1968
Lys Asp Ala Lys Phe Ile Val Gly Pro Met Ser Ser Ala Trp Thr Pro
                645                 650                 655 ttc gac aat aaa atc gtg gtg tac aaa ggc gac gtc tac aac atg gac    2016
Phe Asp Asn Lys Ile Val Val Tyr Lys Gly Asp Val Tyr Asn Met Asp
            660                 665                 670 tac ccg ccc ttc ggc gca gga aga cca gga caa ttt ggc gac atc caa    2064
Tyr Pro Pro Phe Gly Ala Gly Arg Pro Gly Gln Phe Gly Asp Ile Gln
        675                 680                 685 agt cgc acg cct gag agc gaa gac gtc tat gct aac aca caa ctg gta    2112
Ser Arg Thr Pro Glu Ser Glu Asp Val Tyr Ala Asn Thr Gln Leu Val
        690                 695                 700 ctg cag aga ccg tcc gcg ggt acg gtg cac gtg ccg tac tct cag gca    2160
Leu Gln Arg Pro Ser Ala Gly Thr Val His Val Pro Tyr Ser Gln Ala
705                 710                 715                 720 cca tct ggc ttc aag tat tgg cta aaa gaa cga ggg gcg tcg ctg cag    2208
Pro Ser Gly Phe Lys Tyr Trp Leu Lys Glu Arg Gly Ala Ser Leu Gln
                725                 730                 735 cac aca gca cca ttt ggc tgt caa ata gca aca aac ccg gta aga gcg    2256
His Thr Ala Pro Phe Gly Cys Gln Ile Ala Thr Asn Pro Val Arg Ala
            740                 745                 750 atg aac tgc gcc gta ggg aac atg cct atc tcc atc gac ata ccg gac    2304
Met Asn Cys Ala Val Gly Asn Met Pro Ile Ser Ile Asp Ile Pro Asp
        755                 760                 765 gcg gcc ttt acc agg gtc gtc gac gcc cca tct tta acg gac atg tcg    2352
Ala Ala Phe Thr Arg Val Val Asp Ala Pro Ser Leu Thr Asp Met Ser
        770                 775                 780 tgt gag gta tca gcc tgc acc cat tcc tca gac ttt ggg ggc gtt gcc    2400
Cys Glu Val Ser Ala Cys Thr His Ser Ser Asp Phe Gly Gly Val Ala
785                 790                 795                 800
```

|  |  |
|---|---|
| atc att aaa tat gca gcc agt aag aaa ggc aag tgt gca gtg cac tcg<br>Ile Ile Lys Tyr Ala Ala Ser Lys Lys Gly Lys Cys Ala Val His Ser<br>805                                 810                        815 | 2448 |
| atg act aac gcc gtc act att cgg gaa gct gaa ata gaa gta gaa ggg<br>Met Thr Asn Ala Val Thr Ile Arg Glu Ala Glu Ile Glu Val Glu Gly<br>820                             825                          830 | 2496 |
| aac tct cag ttg caa atc tct ttt tcg acg gcc cta gcc agc gcc gaa<br>Asn Ser Gln Leu Gln Ile Ser Phe Ser Thr Ala Leu Ala Ser Ala Glu<br>835                             840                        845 | 2544 |
| ttc cgc gta caa gtc tgt tct aca caa gta cac tgt gca gcc gag tgc<br>Phe Arg Val Gln Val Cys Ser Thr Gln Val His Cys Ala Ala Glu Cys<br>850                             855                        860 | 2592 |
| cat cca ccg aaa gac cat ata gtc aat tac ccg gcg tca cac acc acc<br>His Pro Pro Lys Asp His Ile Val Asn Tyr Pro Ala Ser His Thr Thr<br>865                             870                        875                        880 | 2640 |
| ccc ggg gtc caa gac att tcc gct acg gcg atg tca tgg gtg cag aag<br>Pro Gly Val Gln Asp Ile Ser Ala Thr Ala Met Ser Trp Val Gln Lys<br>885                             890                        895 | 2688 |
| atc acg gga ggt gtg gga ctg gtt gtc gct gtt gca gca ctg atc cta<br>Ile Thr Gly Gly Val Gly Leu Val Val Ala Val Ala Ala Leu Ile Leu<br>900                             905                        910 | 2736 |
| atc gtg gtg cta tgc gtg tcg ttt agc agg cac taa<br>Ile Val Val Leu Cys Val Ser Phe Ser Arg His<br>915                             920 | 2772 |

<210> SEQ ID NO 19
<211> LENGTH: 923
<212> TYPE: PRT
<213> ORGANISM: Artificial Sequence
<220> FEATURE:
<223> OTHER INFORMATION: Synthetic Construct

<400> SEQUENCE: 19

Ser Ile Lys Asp His Phe Asn Val Tyr Lys Ala Thr Arg Pro Tyr Leu
1               5                   10                  15

Ala His Cys Pro Asp Cys Gly Glu Gly His Ser Cys His Ser Pro Val
                20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Lys Thr Asp Asp Ser His Asp Trp
        50                  55                  60

Thr Lys Leu Arg Tyr Met Asp Asn His Met Pro Ala Asp Ala Glu Arg
65                  70                  75                  80

Ala Gly Leu Phe Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Gly Arg Lys Ile Ser His Ser Cys Thr His Pro
        115                 120                 125

Phe His His Asp Pro Pro Val Ile Gly Arg Glu Lys Phe His Ser Arg
    130                 135                 140

Pro Gln His Gly Arg Glu Leu Pro Cys Ser Thr Tyr Ala Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Ser Gln Gln Ser Gly Asn Val Lys Ile Thr Val
            180                 185                 190

Asn Ser Gln Thr Val Arg Tyr Lys Cys Asn Cys Gly Asp Ser Ser Glu

```
                195                 200                 205
Gly Leu Thr Thr Thr Asp Lys Val Ile Asn Asn Cys Lys Val Asp Gln
210                 215                 220

Cys His Ala Ala Val Thr Asn His Lys Lys Trp Gln Tyr Asn Ser Pro
225                 230                 235                 240

Leu Val Pro Arg Asn Ala Glu Phe Gly Asp Arg Lys Gly Lys Val His
                245                 250                 255

Ile Pro Phe Pro Leu Ala Asn Val Thr Cys Arg Val Pro Lys Ala Arg
                260                 265                 270

Asn Pro Thr Val Thr Tyr Gly Lys Asn Gln Val Ile Met Leu Leu Tyr
                275                 280                 285

Pro Asp His Pro Thr Leu Leu Ser Tyr Arg Asn Met Gly Glu Glu Pro
290                 295                 300

Asn Tyr Gln Glu Glu Trp Val Thr His Lys Lys Glu Ile Arg Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Thr Asn Gly Thr Ala His Gly His Pro
                340                 345                 350

His Glu Ile Ile Leu Tyr Tyr Tyr Glu Leu Tyr Pro Thr Met Thr Val
                355                 360                 365

Val Val Leu Ser Val Ala Ser Phe Ile Leu Leu Ser Met Val Gly Val
370                 375                 380

Ala Val Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
                405                 410                 415

Cys Ile Arg Thr Ala Lys Ala Ala Thr Tyr Gln Glu Ala Ala Val Tyr
                420                 425                 430

Leu Trp Asn Glu Gln Gln Pro Leu Phe Trp Leu Gln Ala Leu Ile Pro
                435                 440                 445

Leu Ala Ala Leu Ile Val Leu Cys Asn Cys Leu Arg Leu Leu Pro Cys
450                 455                 460

Cys Cys Lys Met Leu Thr Phe Leu Ala Val Leu Ser Val Gly Ala His
465                 470                 475                 480

Thr Val Ser Ala Tyr Glu His Val Thr Val Ile Pro Asn Thr Val Gly
                485                 490                 495

Val Pro Tyr Lys Thr Leu Val Asn Arg Pro Gly Tyr Ser Pro Met Val
                500                 505                 510

Leu Glu Met Glu Leu Leu Ser Val Thr Leu Glu Pro Thr Leu Ser Leu
                515                 520                 525

Asp Tyr Ile Thr Cys Glu Tyr Lys Thr Val Ile Pro Ser Pro Tyr Val
                530                 535                 540

Lys Cys Cys Gly Thr Ala Glu Cys Lys Asp Lys Ser Leu Pro Asp Tyr
545                 550                 555                 560

Ser Cys Lys Val Phe Thr Gly Val Tyr Pro Phe Met Trp Gly Gly Ala
                565                 570                 575

Tyr Cys Phe Cys Asp Thr Glu Asn Thr Gln Leu Ser Glu Ala His Val
                580                 585                 590

Glu Lys Ser Glu Ser Cys Lys Thr Glu Phe Ala Ser Ala Tyr Arg Ala
                595                 600                 605

His Thr Ala Ser Ala Ser Ala Lys Leu Arg Val Leu Tyr Gln Gly Asn
                610                 615                 620
```

-continued

Asn Ile Thr Val Ala Ala Tyr Ala Asn Gly Asp His Ala Val Thr Val
625                 630                 635                 640

Lys Asp Ala Lys Phe Ile Val Gly Pro Met Ser Ser Ala Trp Thr Pro
            645                 650                 655

Phe Asp Asn Lys Ile Val Val Tyr Lys Gly Asp Val Tyr Asn Met Asp
        660                 665                 670

Tyr Pro Pro Phe Gly Ala Gly Arg Pro Gly Gln Phe Gly Asp Ile Gln
    675                 680                 685

Ser Arg Thr Pro Glu Ser Glu Asp Val Tyr Ala Asn Thr Gln Leu Val
690                 695                 700

Leu Gln Arg Pro Ser Ala Gly Thr Val His Val Pro Tyr Ser Gln Ala
705                 710                 715                 720

Pro Ser Gly Phe Lys Tyr Trp Leu Lys Glu Arg Gly Ala Ser Leu Gln
            725                 730                 735

His Thr Ala Pro Phe Gly Cys Gln Ile Ala Thr Asn Pro Val Arg Ala
        740                 745                 750

Met Asn Cys Ala Val Gly Asn Met Pro Ile Ser Ile Asp Ile Pro Asp
    755                 760                 765

Ala Ala Phe Thr Arg Val Val Asp Ala Pro Ser Leu Thr Asp Met Ser
770                 775                 780

Cys Glu Val Ser Ala Cys Thr His Ser Ser Asp Phe Gly Gly Val Ala
785                 790                 795                 800

Ile Ile Lys Tyr Ala Ala Ser Lys Lys Gly Lys Cys Ala Val His Ser
            805                 810                 815

Met Thr Asn Ala Val Thr Ile Arg Glu Ala Glu Ile Glu Val Glu Gly
        820                 825                 830

Asn Ser Gln Leu Gln Ile Ser Phe Ser Thr Ala Leu Ala Ser Ala Glu
    835                 840                 845

Phe Arg Val Gln Val Cys Ser Thr Gln Val His Cys Ala Ala Glu Cys
850                 855                 860

His Pro Pro Lys Asp His Ile Val Asn Tyr Pro Ala Ser His Thr Thr
865                 870                 875                 880

Pro Gly Val Gln Asp Ile Ser Ala Thr Ala Met Ser Trp Val Gln Lys
            885                 890                 895

Ile Thr Gly Gly Val Gly Leu Val Val Ala Val Ala Ala Leu Ile Leu
        900                 905                 910

Ile Val Val Leu Cys Val Ser Phe Ser Arg His
        915                 920

<210> SEQ ID NO 20
<211> LENGTH: 3744
<212> TYPE: DNA
<213> ORGANISM: Artificial Sequence
<220> FEATURE:
<223> OTHER INFORMATION: proteins C-E3-E2-6K-E1 strain S27 (GenBank:
      AF339485.1)
<220> FEATURE:
<221> NAME/KEY: CDS
<222> LOCATION: (1)..(3744)

<400> SEQUENCE: 20 atg gag ttc atc cca acc caa act ttt tac aac agg agg tac cag cct     48
Met Glu Phe Ile Pro Thr Gln Thr Phe Tyr Asn Arg Arg Tyr Gln Pro
1               5                   10                  15 cga ccc tgg act ccg cgc cct act atc caa gtc atc agg ccc aga ccg     96
Arg Pro Trp Thr Pro Arg Pro Thr Ile Gln Val Ile Arg Pro Arg Pro
            20                  25                  30

| | | | | | | | | | | | | | | | | |
|---|---|---|---|---|---|---|---|---|---|---|---|---|---|---|---|---|
| cgc | ccg | cag | agg | caa | gct | ggg | caa | ctt | gcc | cag | ctg | atc | tca | gca | gtt | 144 |
| Arg | Pro | Gln | Arg | Gln | Ala | Gly | Gln | Leu | Ala | Gln | Leu | Ile | Ser | Ala | Val | |
| | | 35 | | | | 40 | | | | | 45 | | | | | |
| aat | aaa | ctg | aca | atg | cgc | gcg | gta | ccc | caa | cag | aag | cca | cgc | agg | aat | 192 |
| Asn | Lys | Leu | Thr | Met | Arg | Ala | Val | Pro | Gln | Gln | Lys | Pro | Arg | Arg | Asn | |
| 50 | | | | | 55 | | | | | 60 | | | | | | |
| cgg | aag | aat | aag | aag | caa | aag | caa | aag | caa | cag | gcg | cca | caa | aac | aac | 240 |
| Arg | Lys | Asn | Lys | Lys | Gln | Lys | Gln | Lys | Gln | Gln | Ala | Pro | Gln | Asn | Asn | |
| 65 | | | | 70 | | | | | 75 | | | | | 80 | | |
| aca | aac | caa | aag | aag | cag | cca | cct | aaa | aag | aaa | cca | gct | caa | aag | aaa | 288 |
| Thr | Asn | Gln | Lys | Lys | Gln | Pro | Pro | Lys | Lys | Lys | Pro | Ala | Gln | Lys | Lys | |
| | | | | 85 | | | | | 90 | | | | | 95 | | |
| aag | aag | ccg | ggc | cgc | aga | gag | agg | atg | tgc | atg | aaa | atc | gaa | aat | gac | 336 |
| Lys | Lys | Pro | Gly | Arg | Arg | Glu | Arg | Met | Cys | Met | Lys | Ile | Glu | Asn | Asp | |
| | | | 100 | | | | | 105 | | | | | 110 | | | |
| tgt | att | ttc | gaa | gtc | aag | cac | gaa | ggt | aag | gta | aca | ggt | tac | gcg | tgc | 384 |
| Cys | Ile | Phe | Glu | Val | Lys | His | Glu | Gly | Lys | Val | Thr | Gly | Tyr | Ala | Cys | |
| | | | 115 | | | | | 120 | | | | | 125 | | | |
| ttg | gtg | ggg | gac | aaa | gta | atg | aaa | cca | gca | cac | gta | aag | ggg | acc | atc | 432 |
| Leu | Val | Gly | Asp | Lys | Val | Met | Lys | Pro | Ala | His | Val | Lys | Gly | Thr | Ile | |
| | 130 | | | | | 135 | | | | | 140 | | | | | |
| gat | aac | gcg | gac | ctg | gcc | aaa | ttg | gcc | ttt | aag | cgg | tca | tct | aag | tac | 480 |
| Asp | Asn | Ala | Asp | Leu | Ala | Lys | Leu | Ala | Phe | Lys | Arg | Ser | Ser | Lys | Tyr | |
| 145 | | | | | 150 | | | | | 155 | | | | | 160 | |
| gac | ctt | gaa | tgc | gcg | cag | ata | ccc | gtg | cac | atg | aag | tcc | gac | gct | tcg | 528 |
| Asp | Leu | Glu | Cys | Ala | Gln | Ile | Pro | Val | His | Met | Lys | Ser | Asp | Ala | Ser | |
| | | | | 165 | | | | | 170 | | | | | 175 | | |
| aag | ttc | acc | cat | gag | aaa | ccg | gag | ggg | tac | tac | aac | tgg | cac | cac | gga | 576 |
| Lys | Phe | Thr | His | Glu | Lys | Pro | Glu | Gly | Tyr | Tyr | Asn | Trp | His | His | Gly | |
| | | | 180 | | | | | 185 | | | | | 190 | | | |
| gca | gta | cag | tac | tca | gga | ggc | cgg | ttc | acc | atc | cct | aca | ggt | gcg | ggc | 624 |
| Ala | Val | Gln | Tyr | Ser | Gly | Gly | Arg | Phe | Thr | Ile | Pro | Thr | Gly | Ala | Gly | |
| | | | 195 | | | | | 200 | | | | | 205 | | | |
| aaa | cca | ggg | gac | agc | ggt | aga | ccg | atc | ttc | gac | aac | aag | gga | cgc | gtg | 672 |
| Lys | Pro | Gly | Asp | Ser | Gly | Arg | Pro | Ile | Phe | Asp | Asn | Lys | Gly | Arg | Val | |
| 210 | | | | | 215 | | | | | 220 | | | | | | |
| gtg | gcc | ata | gtc | tta | gga | gga | gct | aat | gaa | gga | gcc | cgt | aca | gcc | ctc | 720 |
| Val | Ala | Ile | Val | Leu | Gly | Gly | Ala | Asn | Glu | Gly | Ala | Arg | Thr | Ala | Leu | |
| 225 | | | | | 230 | | | | | 235 | | | | | 240 | |
| tca | gtg | gtg | acc | tgg | aat | aaa | gac | att | gtc | act | aaa | atc | acc | cct | gag | 768 |
| Ser | Val | Val | Thr | Trp | Asn | Lys | Asp | Ile | Val | Thr | Lys | Ile | Thr | Pro | Glu | |
| | | | | 245 | | | | | 250 | | | | | 255 | | |
| gga | gcc | gaa | gag | tgg | agt | ctt | gcc | atc | cca | gtt | atg | tgc | ctg | ttg | gca | 816 |
| Gly | Ala | Glu | Glu | Trp | Ser | Leu | Ala | Ile | Pro | Val | Met | Cys | Leu | Leu | Ala | |
| | | | 260 | | | | | 265 | | | | | 270 | | | |
| aat | acc | acg | ttc | ccc | tgc | tcc | cag | ccc | cct | tgc | ata | ccc | tgc | tgc | tac | 864 |
| Asn | Thr | Thr | Phe | Pro | Cys | Ser | Gln | Pro | Pro | Cys | Ile | Pro | Cys | Cys | Tyr | |
| | | 275 | | | | | 280 | | | | | 285 | | | | |
| gaa | aag | gaa | ccg | gag | gaa | acc | cta | cgc | atg | ctt | gag | gac | aac | gtc | atg | 912 |
| Glu | Lys | Glu | Pro | Glu | Glu | Thr | Leu | Arg | Met | Leu | Glu | Asp | Asn | Val | Met | |
| | 290 | | | | | 295 | | | | | 300 | | | | | |
| aga | cct | ggg | tac | tat | cag | ctg | cta | caa | gca | tca | tta | aca | tgt | tct | ccc | 960 |
| Arg | Pro | Gly | Tyr | Tyr | Gln | Leu | Leu | Gln | Ala | Ser | Leu | Thr | Cys | Ser | Pro | |
| 305 | | | | | 310 | | | | | 315 | | | | | 320 | |
| cac | cgc | cag | cga | cgc | agc | acc | aag | gac | aac | ttc | aat | gtc | tat | aaa | gcc | 1008 |
| His | Arg | Gln | Arg | Arg | Ser | Thr | Lys | Asp | Asn | Phe | Asn | Val | Tyr | Lys | Ala | |
| | | | | 325 | | | | | 330 | | | | | 335 | | |
| aca | aga | cca | tac | tta | gct | cac | tgt | ccc | gac | tgt | gga | gaa | ggg | cac | tcg | 1056 |
| Thr | Arg | Pro | Tyr | Leu | Ala | His | Cys | Pro | Asp | Cys | Gly | Glu | Gly | His | Ser | |

```
                340             345                 350
tgc cat agt ccc gta gca cta gaa cgc atc aga aat gaa gcg aca gac         1104
Cys His Ser Pro Val Ala Leu Glu Arg Ile Arg Asn Glu Ala Thr Asp
            355                 360                 365 ggg acg ctg aaa atc cag gtc tcc ttg caa att gga ata ggg acg gat         1152
Gly Thr Leu Lys Ile Gln Val Ser Leu Gln Ile Gly Ile Gly Thr Asp
370                 375                 380 gat agc cat gat tgg acc aag ctg cgt tac atg gac aat cac ata cca         1200
Asp Ser His Asp Trp Thr Lys Leu Arg Tyr Met Asp Asn His Ile Pro
385                 390                 395                 400 gca gac gca ggg agg gcc ggg cta ttt gta aga aca tca gca cca tgc         1248
Ala Asp Ala Gly Arg Ala Gly Leu Phe Val Arg Thr Ser Ala Pro Cys
                405                 410                 415 acg att act gga aca atg gga cac ttc atc ctg gcc cga tgt ccg aaa         1296
Thr Ile Thr Gly Thr Met Gly His Phe Ile Leu Ala Arg Cys Pro Lys
            420                 425                 430 gga gaa act ctg acg gtg gga ttc act gac agt agg aag att agt cac         1344
Gly Glu Thr Leu Thr Val Gly Phe Thr Asp Ser Arg Lys Ile Ser His
            435                 440                 445 tca tgt acg cac cca ttt cac cac gac cct cct gtg ata ggc cgg gaa         1392
Ser Cys Thr His Pro Phe His His Asp Pro Pro Val Ile Gly Arg Glu
450                 455                 460 aaa ttc cat tcc cga ccg cag cac ggt aaa gag cta cct tgc agc acg         1440
Lys Phe His Ser Arg Pro Gln His Gly Lys Glu Leu Pro Cys Ser Thr
465                 470                 475                 480 tac gtg cag agc aac gcc gca act gcc gag gag ata gag gta cac atg         1488
Tyr Val Gln Ser Asn Ala Ala Thr Ala Glu Glu Ile Glu Val His Met
                485                 490                 495 ccc cca gac acc cct gat cgc aca ttg ctg tca caa cag tcc ggc aac         1536
Pro Pro Asp Thr Pro Asp Arg Thr Leu Leu Ser Gln Gln Ser Gly Asn
            500                 505                 510 gta aag atc aca gtc aac ggc cgg acg gtg cgg tat aag tgt aat tgc         1584
Val Lys Ile Thr Val Asn Gly Arg Thr Val Arg Tyr Lys Cys Asn Cys
            515                 520                 525 ggt ggc tca aat gaa gga cta ata act aca gat aaa gtg att aat aac         1632
Gly Gly Ser Asn Glu Gly Leu Ile Thr Thr Asp Lys Val Ile Asn Asn
530                 535                 540 tgc aag gtt gat caa tgt cat gcc gcg gtc acc aat cac aaa aag tgg         1680
Cys Lys Val Asp Gln Cys His Ala Ala Val Thr Asn His Lys Lys Trp
545                 550                 555                 560 cag tat aac tcc cct ctg gtc ccg cgt aac gct gaa ctc ggg gac cga         1728
Gln Tyr Asn Ser Pro Leu Val Pro Arg Asn Ala Glu Leu Gly Asp Arg
                565                 570                 575 aaa gga aaa att cac atc ccg ttt ccg ctg gca aat gta aca tgc atg         1776
Lys Gly Lys Ile His Ile Pro Phe Pro Leu Ala Asn Val Thr Cys Met
            580                 585                 590 gtg cct aaa gca agg aac ccc acc gtg acg tac ggg aaa aac caa gtc         1824
Val Pro Lys Ala Arg Asn Pro Thr Val Thr Tyr Gly Lys Asn Gln Val
            595                 600                 605 atc atg cta ctg tat cct gac cac cca aca ctc ctg tcc tac cgg agt         1872
Ile Met Leu Leu Tyr Pro Asp His Pro Thr Leu Leu Ser Tyr Arg Ser
610                 615                 620 atg gga gaa gaa cca aac tat caa gaa gag tgg gtg acg cac aag aag         1920
Met Gly Glu Glu Pro Asn Tyr Gln Glu Glu Trp Val Thr His Lys Lys
625                 630                 635                 640 gag gtc gtg cta acc gtg ccg act gaa ggg ctc gag gtt acg tgg ggc         1968
Glu Val Val Leu Thr Val Pro Thr Glu Gly Leu Glu Val Thr Trp Gly
                645                 650                 655 aac aac gag ccg tat aag tat tgg ccg cag tta tct gca aac ggt aca         2016
```

-continued

```
                Asn Asn Glu Pro Tyr Lys Tyr Trp Pro Gln Leu Ser Ala Asn Gly Thr
                            660                 665                 670 gcc cac ggc cac ccg cat gag ata atc ttg tac tat tat gag ctg tac          2064
Ala His Gly His Pro His Glu Ile Ile Leu Tyr Tyr Tyr Glu Leu Tyr
            675                 680                 685 cct act atg act gta gta gtt gtg tca gtg gcc tcg ttc ata ctc ctg          2112
Pro Thr Met Thr Val Val Val Val Ser Val Ala Ser Phe Ile Leu Leu
690                 695                 700 tcg atg gtg ggt atg gca gtg ggg atg tgc atg tgt gca cga cgc aga          2160
Ser Met Val Gly Met Ala Val Gly Met Cys Met Cys Ala Arg Arg Arg
705                 710                 715                 720 tgc atc aca cca tac gaa ctg aca cca gga gct acc gtc cct ttc ctg          2208
Cys Ile Thr Pro Tyr Glu Leu Thr Pro Gly Ala Thr Val Pro Phe Leu
            725                 730                 735 ctt agc cta ata tgc tgc atc aga aca gct aaa gcg gcc aca tac caa          2256
Leu Ser Leu Ile Cys Cys Ile Arg Thr Ala Lys Ala Ala Thr Tyr Gln
            740                 745                 750 gag gct gcg gta tac ctg tgg aac gag cag caa cct ttg ttt tgg cta          2304
Glu Ala Ala Val Tyr Leu Trp Asn Glu Gln Gln Pro Leu Phe Trp Leu
            755                 760                 765 caa gcc ctt att ccg ctg gca gcc ctg att gtc cta tgc aac tgt ctg          2352
Gln Ala Leu Ile Pro Leu Ala Ala Leu Ile Val Leu Cys Asn Cys Leu
770                 775                 780 aga ctc tta cca tgc tgt tgt aaa acg ttg gct ttt tta gcc gta atg          2400
Arg Leu Leu Pro Cys Cys Cys Lys Thr Leu Ala Phe Leu Ala Val Met
785                 790                 795                 800 agc atc ggt gcc cac act gtg agc gcg tac gaa cac gta aca gtg atc          2448
Ser Ile Gly Ala His Thr Val Ser Ala Tyr Glu His Val Thr Val Ile
            805                 810                 815 ccg aac acg gtg gga gta ccg tat aag act cta gtc aac aga ccg ggc          2496
Pro Asn Thr Val Gly Val Pro Tyr Lys Thr Leu Val Asn Arg Pro Gly
            820                 825                 830 tac agc ccc atg gta ctg gag atg gag cta ctg tca gtc act ttg gag          2544
Tyr Ser Pro Met Val Leu Glu Met Glu Leu Leu Ser Val Thr Leu Glu
            835                 840                 845 cca acg cta tcg ctt gat tac atc acg tgc gaa tac aaa acc gtc atc          2592
Pro Thr Leu Ser Leu Asp Tyr Ile Thr Cys Glu Tyr Lys Thr Val Ile
850                 855                 860 ccg tct ccg tac gtg aaa tgc tgc ggt aca gca gag tgc aag gac aaa          2640
Pro Ser Pro Tyr Val Lys Cys Cys Gly Thr Ala Glu Cys Lys Asp Lys
865                 870                 875                 880 aac cta cct gac tac agc tgt aag gtc ttc acc ggc gtc tac cca ttt          2688
Asn Leu Pro Asp Tyr Ser Cys Lys Val Phe Thr Gly Val Tyr Pro Phe
            885                 890                 895 atg tgg ggc ggc gcc tac tgc ttc tgc gac gct gaa aac acg caa ttg          2736
Met Trp Gly Gly Ala Tyr Cys Phe Cys Asp Ala Glu Asn Thr Gln Leu
            900                 905                 910 agc gaa gca cat gtg gag aag tcc gaa tca tgc aaa aca gaa ttt gca          2784
Ser Glu Ala His Val Glu Lys Ser Glu Ser Cys Lys Thr Glu Phe Ala
            915                 920                 925 tca gca tac agg gct cat acc gca tcc gca tca gct aag ctc cgc gtc          2832
Ser Ala Tyr Arg Ala His Thr Ala Ser Ala Ser Ala Lys Leu Arg Val
930                 935                 940 ctt tac caa gga aat aac atc act gta act gcc tat gca aac ggc gac          2880
Leu Tyr Gln Gly Asn Asn Ile Thr Val Thr Ala Tyr Ala Asn Gly Asp
945                 950                 955                 960 cat gcc gtc aca gtt aag gac gcc aaa ttc att gtg ggg cca atg tct          2928
His Ala Val Thr Val Lys Asp Ala Lys Phe Ile Val Gly Pro Met Ser
            965                 970                 975
```

```
tca gcc tgg aca cct ttc gac aac aaa atc gtg gtg tac aaa ggt gac    2976
Ser Ala Trp Thr Pro Phe Asp Asn Lys Ile Val Val Tyr Lys Gly Asp
            980                 985                 990 gtt tac aac atg gac tac ccg ccc ttt ggc gca gga aga cca gga caa    3024
Val Tyr Asn Met Asp Tyr Pro Pro Phe Gly Ala Gly Arg Pro Gly Gln
        995                 1000                1005 ttt ggc gat atc caa agt cgc acg cct gag agc aaa gac gtc tat        3069
Phe Gly Asp Ile Gln Ser Arg Thr Pro Glu Ser Lys Asp Val Tyr
    1010                1015                1020 gct aac aca caa ctg gta ctg cag aga ccg gct gcg ggt acg gta        3114
Ala Asn Thr Gln Leu Val Leu Gln Arg Pro Ala Ala Gly Thr Val
    1025                1030                1035 cac gtg cca tac tct cag gca cca tct ggc ttt aag tat tgg tta        3159
His Val Pro Tyr Ser Gln Ala Pro Ser Gly Phe Lys Tyr Trp Leu
    1040                1045                1050 aaa gaa cga ggg gcg tcg cta cag cac aca gca cca ttt ggc tgc        3204
Lys Glu Arg Gly Ala Ser Leu Gln His Thr Ala Pro Phe Gly Cys
    1055                1060                1065 caa ata gca aca aac ccg gta aga gcg atg aac tgc gcc gta ggg        3249
Gln Ile Ala Thr Asn Pro Val Arg Ala Met Asn Cys Ala Val Gly
    1070                1075                1080 aac atg ccc atc tcc atc gac ata ccg gat gcg gcc ttc act agg        3294
Asn Met Pro Ile Ser Ile Asp Ile Pro Asp Ala Ala Phe Thr Arg
    1085                1090                1095 gtc gtc gac gcg ccc tct tta acg gac atg tca tgc gag gta cca        3339
Val Val Asp Ala Pro Ser Leu Thr Asp Met Ser Cys Glu Val Pro
    1100                1105                1110 gcc tgc acc cat tcc tca gac ttt ggg ggc gtc gcc att att aaa        3384
Ala Cys Thr His Ser Ser Asp Phe Gly Gly Val Ala Ile Ile Lys
    1115                1120                1125 tat gca gtc agc aag aaa ggc aag tgt gcg gtg cat tcg atg acc        3429
Tyr Ala Val Ser Lys Lys Gly Lys Cys Ala Val His Ser Met Thr
    1130                1135                1140 aac gcc gtc act atc cgg gaa gct gag ata gaa gtt gaa ggg aat        3474
Asn Ala Val Thr Ile Arg Glu Ala Glu Ile Glu Val Glu Gly Asn
    1145                1150                1155 tct cag ctg caa atc tct ttc tcg acg gcc ttg gcc agc gcc gaa        3519
Ser Gln Leu Gln Ile Ser Phe Ser Thr Ala Leu Ala Ser Ala Glu
    1160                1165                1170 ttc cgc gta caa gtc tgt tct aca caa gta cac tgt gca gcc gag        3564
Phe Arg Val Gln Val Cys Ser Thr Gln Val His Cys Ala Ala Glu
    1175                1180                1185 tgc cac cct ccg aag gac cac ata gtc aac tac ccg gcg tca cat        3609
Cys His Pro Pro Lys Asp His Ile Val Asn Tyr Pro Ala Ser His
    1190                1195                1200 acc acc ctc ggg gtc cag gac att tcc gct acg gcg atg tca tgg        3654
Thr Thr Leu Gly Val Gln Asp Ile Ser Ala Thr Ala Met Ser Trp
    1205                1210                1215 gtg cag aag atc acg gga ggt gtg gga ctg gtt gtc gct gtt gca        3699
Val Gln Lys Ile Thr Gly Gly Val Gly Leu Val Val Ala Val Ala
    1220                1225                1230 gca ctg att cta atc gtg gtg cta tgc gtg tcg ttc agc agg cac        3744
Ala Leu Ile Leu Ile Val Val Leu Cys Val Ser Phe Ser Arg His
    1235                1240                1245
```

<210> SEQ ID NO 21
<211> LENGTH: 1248
<212> TYPE: PRT
<213> ORGANISM: Artificial Sequence
<220> FEATURE:
<223> OTHER INFORMATION: Synthetic Construct

<400> SEQUENCE: 21

| | | | | | | | | | | | | | | |
|---|---|---|---|---|---|---|---|---|---|---|---|---|---|---|
|Met|Glu|Phe|Ile|Pro|Thr|Gln|Thr|Phe|Tyr|Asn|Arg|Arg|Tyr|Gln|Pro|
|1| | | |5| | | | |10| | | | |15| |

Arg Pro Trp Thr Pro Arg Pro Thr Ile Gln Val Ile Arg Pro Arg Pro
               20               25               30

Arg Pro Gln Arg Gln Ala Gly Gln Leu Ala Gln Leu Ile Ser Ala Val
            35               40               45

Asn Lys Leu Thr Met Arg Ala Val Pro Gln Gln Lys Pro Arg Arg Asn
50               55               60

Arg Lys Asn Lys Lys Gln Lys Gln Gln Ala Pro Gln Asn Asn
65              70              75               80

Thr Asn Gln Lys Lys Gln Pro Pro Lys Lys Pro Ala Gln Lys Lys
            85               90               95

Lys Lys Pro Gly Arg Arg Glu Arg Met Cys Met Lys Ile Glu Asn Asp
          100               105             110

Cys Ile Phe Glu Val Lys His Glu Gly Lys Val Thr Gly Tyr Ala Cys
          115               120             125

Leu Val Gly Asp Lys Val Met Lys Pro Ala His Val Lys Gly Thr Ile
   130                135             140

Asp Asn Ala Asp Leu Ala Lys Leu Ala Phe Lys Arg Ser Ser Lys Tyr
145              150              155             160

Asp Leu Glu Cys Ala Gln Ile Pro Val His Met Lys Ser Asp Ala Ser
          165               170             175

Lys Phe Thr His Glu Lys Pro Glu Gly Tyr Tyr Asn Trp His His Gly
          180               185             190

Ala Val Gln Tyr Ser Gly Gly Arg Phe Thr Ile Pro Thr Gly Ala Gly
          195               200             205

Lys Pro Gly Asp Ser Gly Arg Pro Ile Phe Asp Asn Lys Gly Arg Val
   210                215             220

Val Ala Ile Val Leu Gly Gly Ala Asn Glu Gly Ala Arg Thr Ala Leu
225              230              235             240

Ser Val Val Thr Trp Asn Lys Asp Ile Val Thr Lys Ile Thr Pro Glu
          245               250             255

Gly Ala Glu Glu Trp Ser Leu Ala Ile Pro Val Met Cys Leu Leu Ala
          260               265             270

Asn Thr Thr Phe Pro Cys Ser Gln Pro Pro Cys Ile Pro Cys Cys Tyr
          275               280             285

Glu Lys Glu Pro Glu Glu Thr Leu Arg Met Leu Glu Asp Asn Val Met
   290                295             300

Arg Pro Gly Tyr Tyr Gln Leu Leu Gln Ala Ser Leu Thr Cys Ser Pro
305              310              315             320

His Arg Gln Arg Arg Ser Thr Lys Asp Asn Phe Asn Val Tyr Lys Ala
          325               330             335

Thr Arg Pro Tyr Leu Ala His Cys Pro Asp Cys Gly Glu Gly His Ser
          340               345             350

Cys His Ser Pro Val Ala Leu Glu Arg Ile Arg Asn Glu Ala Thr Asp
          355               360             365

Gly Thr Leu Lys Ile Gln Val Ser Leu Gln Ile Gly Ile Gly Thr Asp
   370                375             380

Asp Ser His Asp Trp Thr Lys Leu Arg Tyr Met Asp Asn His Ile Pro
385              390              395             400

Ala Asp Ala Gly Arg Ala Gly Leu Phe Val Arg Thr Ser Ala Pro Cys

```
            405                 410                 415
Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
            435                 440                 445

Ser Cys Thr His Pro Phe His His Asp Pro Pro Val Ile Gly Arg Glu
            450                 455                 460

Lys Phe His Ser Arg Pro Gln His Gly Lys Glu Leu Pro Cys Ser Thr
465                 470                 475                 480

Tyr Val Gln Ser Asn Ala Ala Thr Ala Glu Glu Ile Glu Val His Met
            485                 490                 495

Pro Pro Asp Thr Pro Asp Arg Thr Leu Leu Ser Gln Gln Ser Gly Asn
            500                 505                 510

Val Lys Ile Thr Val Asn Gly Arg Thr Val Arg Tyr Lys Cys Asn Cys
            515                 520                 525

Gly Gly Ser Asn Glu Gly Leu Ile Thr Asp Lys Val Ile Asn Asn
            530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
            565                 570                 575

Lys Gly Lys Ile His Ile Pro Phe Pro Leu Ala Asn Val Thr Cys Met
            580                 585                 590

Val Pro Lys Ala Arg Asn Pro Thr Val Thr Tyr Gly Lys Asn Gln Val
            595                 600                 605

Ile Met Leu Leu Tyr Pro Asp His Pro Thr Leu Leu Ser Tyr Arg Ser
            610                 615                 620

Met Gly Glu Glu Pro Asn Tyr Gln Glu Glu Trp Val Thr His Lys Lys
625                 630                 635                 640

Glu Val Val Leu Thr Val Pro Thr Glu Gly Leu Glu Val Thr Trp Gly
            645                 650                 655

Asn Asn Glu Pro Tyr Lys Tyr Trp Pro Gln Leu Ser Ala Asn Gly Thr
            660                 665                 670

Ala His Gly His Pro His Glu Ile Ile Leu Tyr Tyr Tyr Glu Leu Tyr
            675                 680                 685

Pro Thr Met Thr Val Val Val Ser Val Ala Ser Phe Ile Leu Leu
            690                 695                 700

Ser Met Val Gly Met Ala Val Gly Met Cys Met Cys Ala Arg Arg Arg
705                 710                 715                 720

Cys Ile Thr Pro Tyr Glu Leu Thr Pro Gly Ala Thr Val Pro Phe Leu
            725                 730                 735

Leu Ser Leu Ile Cys Cys Ile Arg Thr Ala Lys Ala Ala Thr Tyr Gln
            740                 745                 750

Glu Ala Ala Val Tyr Leu Trp Asn Glu Gln Gln Pro Leu Phe Trp Leu
            755                 760                 765

Gln Ala Leu Ile Pro Leu Ala Ala Leu Ile Val Leu Cys Asn Cys Leu
            770                 775                 780

Arg Leu Leu Pro Cys Cys Cys Lys Thr Leu Ala Phe Leu Ala Val Met
785                 790                 795                 800

Ser Ile Gly Ala His Thr Val Ser Ala Tyr Glu His Val Thr Val Ile
            805                 810                 815

Pro Asn Thr Val Gly Val Pro Tyr Lys Thr Leu Val Asn Arg Pro Gly
            820                 825                 830
```

```
Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
            915                 920                 925

Ser Ala Tyr Arg Ala His Thr Ala Ser Ala Ser Ala Lys Leu Arg Val
        930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro Phe Gly Ala Gly Arg Pro Gly Gln
        995                 1000                1005

Phe Gly Asp Ile Gln Ser Arg Thr Pro Glu Ser Lys Asp Val Tyr
    1010                1015                1020

Ala Asn Thr Gln Leu Val Leu Gln Arg Pro Ala Ala Gly Thr Val
    1025                1030                1035

His Val Pro Tyr Ser Gln Ala Pro Ser Gly Phe Lys Tyr Trp Leu
    1040                1045                1050

Lys Glu Arg Gly Ala Ser Leu Gln His Thr Ala Pro Phe Gly Cys
    1055                1060                1065

Gln Ile Ala Thr Asn Pro Val Arg Ala Met Asn Cys Ala Val Gly
    1070                1075                1080

Asn Met Pro Ile Ser Ile Asp Ile Pro Asp Ala Ala Phe Thr Arg
    1085                1090                1095

Val Val Asp Ala Pro Ser Leu Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Ala Val Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230
```

Ala Leu Ile Leu Ile Val Val Leu Cys Val Ser Phe Ser Arg His
    1235                1240                1245

<210> SEQ ID NO 22
<211> LENGTH: 1248
<212> TYPE: PRT
<213> ORGANISM: Artificial Sequence
<220> FEATURE:
<223> OTHER INFORMATION: proteins C-E3-E2-6K-E1 strain 05.61

<400> SEQUENCE: 22

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

```
Cys His Ser Pro Val Ala Leu Glu Arg Ile Arg Asn Glu Ala Thr Asp
            355                 360                 365

Gly Thr Leu Lys Ile Gln Val Ser Leu Gln Ile Gly Ile Lys Thr Asp
        370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
```

-continued

```
            770                 775                 780
Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
                820                 825                 830

Tyr Ser Pro Met Val Leu Glu Met Glu Leu Leu Ser Val Thr Leu Glu
                835                 840                 845

Pro Thr Leu Ser Leu Asp Tyr Ile Thr Cys Glu Tyr Lys Thr Val Ile
850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
                900                 905                 910

Ser Glu Ala His Val Glu Lys Ser Glu Ser Cys Lys Thr Glu Phe Ala
                915                 920                 925

Ser Ala Tyr Arg Ala His Thr Ala Ser Ala Ser Ala Lys Leu Arg Val
                930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
                980                 985                 990

Val Tyr Asn Met Asp Tyr Pro Pro Phe Gly Ala Gly Arg Pro Gly Gln
                995                 1000                1005

Phe Gly Asp Ile Gln Ser Arg Thr Pro Glu Ser Lys Asp Val Tyr
                1010                1015                1020

Ala Asn Thr Gln Leu Val Leu Gln Arg Pro Ala Ala Gly Thr Val
                1025                1030                1035

His Val Pro Tyr Ser Gln Ala Pro Ser Gly Phe Lys Tyr Trp Leu
                1040                1045                1050

Lys Glu Arg Gly Ala Ser Leu Gln His Thr Ala Pro Phe Gly Cys
                1055                1060                1065

Gln Ile Ala Thr Asn Pro Val Arg Ala Val Asn Cys Ala Val Gly
                1070                1075                1080

Asn Met Pro Ile Ser Ile Asp Ile Pro Glu Ala Ala Phe Thr Arg
                1085                1090                1095

Val Val Asp Ala Pro Ser Leu Thr Asp Met Ser Cys Glu Val Pro
                1100                1105                1110

Ala Cys Thr His Ser Ser Asp Phe Gly Gly Val Ala Ile Ile Lys
                1115                1120                1125

Tyr Ala Ala Ser Lys Lys Gly Lys Cys Ala Val His Ser Met Thr
                1130                1135                1140

Asn Ala Val Thr Ile Arg Glu Ala Glu Ile Glu Val Glu Gly Asn
                1145                1150                1155

Ser Gln Leu Gln Ile Ser Phe Ser Thr Ala Leu Ala Ser Ala Glu
                1160                1165                1170

Phe Arg Val Gln Val Cys Ser Thr Gln Val His Cys Ala Ala Glu
                1175                1180                1185
```

```
Cys His Pro Pro Lys Asp His Ile Val Asn Tyr Pro Ala Ser His
    1190            1195                1200

Thr Thr Leu Gly Val Gln Asp Ile Ser Ala Thr Ala Met Ser Trp
    1205            1210                1215

Val Gln Lys Ile Thr Gly Gly Val Gly Leu Val Val Ala Val Ala
    1220            1225                1230

Ala Leu Ile Leu Ile Val Val Leu Cys Val Ser Phe Ser Arg His
    1235            1240                1245

<210> SEQ ID NO 23
<211> LENGTH: 1248
<212> TYPE: PRT
<213> ORGANISM: Artificial Sequence
<220> FEATURE:
<223> OTHER INFORMATION: proteins C-E3-E2-6K-E1 strain 05.209

<400> SEQUENCE: 23

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
50                  55                  60

Arg Lys Asn Lys Lys Gln Lys Gln Gln Ala Pro Gln Asn Asn
65                  70                  75                  80

Thr Asn Gln Lys Lys Gln Pro Pro Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
    290                 295                 300
```

-continued

```
Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
            325                 330                 335

Thr Arg Pro Tyr Leu Ala His Cys Pro Asp Cys Gly Glu Gly His Ser
        340                 345                 350

Cys His Ser Pro Val Ala Leu Glu Arg Ile Arg Asn Glu Ala Thr Asp
    355                 360                 365

Gly Thr Leu Lys Ile Gln Val Ser Leu Gln Ile Gly Ile Lys Thr Asp
370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
            405                 410                 415

Thr Ile Thr Gly Thr Met Gly His Phe Ile Leu Ala Arg Cys Pro Lys
        420                 425                 430

Gly Glu Thr Leu Thr Val Gly Phe Thr Asp Ser Arg Lys Ile Ser His
    435                 440                 445

Ser Cys Thr His Pro Phe His His Asp Pro Pro Val Ile Gly Arg Glu
450                 455                 460

Lys Phe His Ser Arg Pro Arg His Gly Lys Glu Leu Pro Cys Ser Thr
465                 470                 475                 480

Tyr Val Gln Ser Thr Ala Ala Thr Thr Glu Glu Ile Glu Val His Met
            485                 490                 495

Pro Pro Asp Thr Pro Asp Arg Thr Leu Met Ser Gln Gln Ser Gly Asn
        500                 505                 510

Val Lys Ile Thr Val Asn Gly Gln Thr Val Arg Tyr Lys Cys Asn Cys
    515                 520                 525

Gly Gly Ser Asn Glu Gly Leu Thr Thr Thr Asp Lys Val Ile Asn Asn
530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
            565                 570                 575

Lys Gly Lys Ile His Ile Pro Phe Pro Leu Ala Asn Val Thr Cys Arg
        580                 585                 590

Val Pro Lys Ala Arg Asn Pro Thr Val Thr Tyr Gly Lys Asn Gln Val
    595                 600                 605

Ile Met Leu Leu Tyr Pro Asp His Pro Thr Leu Leu Ser Tyr Arg Asn
610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
            645                 650                 655

Asn Asn Glu Pro Tyr Lys Tyr Trp Pro Gln Leu Ser Thr Asn Gly Thr
        660                 665                 670

Ala His Gly His Pro His Glu Ile Ile Leu Tyr Tyr Tyr Glu Leu Tyr
    675                 680                 685

Pro Thr Met Thr Val Val Val Ser Val Ala Thr Phe Ile Leu Leu
690                 695                 700

Ser Met Val Gly Met Ala Ala Gly Met Cys Met Cys Ala Arg Arg Arg
705                 710                 715                 720
```

```
Cys Ile Thr Pro Tyr Glu Leu Thr Pro Gly Ala Val Pro Phe Leu
            725                 730                 735

Leu Ser Leu Ile Cys Cys Ile Arg Thr Ala Lys Ala Ala Thr Tyr Gln
        740                 745                 750

Glu Ala Ala Ile Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
        770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
                820                 825                 830

Tyr Ser Pro Met Val Leu Glu Met Glu Leu Leu Ser Val Thr Leu Glu
                835                 840                 845

Pro Thr Leu Ser Leu Asp Tyr Ile Thr Cys Glu Tyr Lys Thr Val Ile
            850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
                900                 905                 910

Ser Glu Ala His Val Glu Lys Ser Glu Ser Cys Lys Thr Glu Phe Ala
                915                 920                 925

Ser Ala Tyr Arg Ala His Thr Ala Ser Ala Ser Ala Lys Leu Arg Val
            930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
                980                 985                 990

Val Tyr Asn Met Asp Tyr Pro Pro Phe Gly Ala Gly Arg Pro Gly Gln
            995                 1000                1005

Phe Gly Asp Ile Gln Ser Arg Thr Pro Glu Ser Lys Asp Val Tyr
        1010                1015                1020

Ala Asn Thr Gln Leu Val Leu Gln Arg Pro Ala Ala Gly Thr Val
        1025                1030                1035

His Val Pro Tyr Ser Gln Ala Pro Ser Gly Phe Lys Tyr Trp Leu
        1040                1045                1050

Lys Glu Arg Gly Ala Ser Leu Gln His Thr Ala Pro Phe Gly Cys
        1055                1060                1065

Gln Ile Ala Thr Asn Pro Val Arg Ala Val Asn Cys Ala Val Gly
        1070                1075                1080

Asn Met Pro Ile Ser Ile Asp Ile Pro Glu Ala Ala Phe Thr Arg
        1085                1090                1095

Val Val Asp Ala Pro Ser Leu Thr Asp Met Ser Cys Glu Val Pro
        1100                1105                1110

Ala Cys Thr His Ser Ser Asp Phe Gly Gly Val Ala Ile Ile Lys
        1115                1120                1125

Tyr Ala Ala Ser Lys Lys Gly Lys Cys Ala Val His Ser Met Thr
```

-continued

```
                1130                1135                1140

Asn Ala Val Thr Ile Arg Glu Ala Glu Ile Glu Val Glu Gly Asn
            1145                1150                1155

Ser Gln Leu Gln Ile Ser Phe Ser Thr Ala Leu Ala Ser Ala Glu
1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 24
<211> LENGTH: 1248
<212> TYPE: PRT
<213> ORGANISM: Artificial Sequence
<220> FEATURE:
<223> OTHER INFORMATION: proteins C-E3-E2-6K-E1 strain 05.115

<400> SEQUENCE: 24

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
```

```
                    245                 250                 255
Gly Ala Glu Glu Trp Ser Leu Ala Ile Pro Val Met Cys Leu Leu Ala
                260                 265                 270

Asn Thr Thr Phe Pro Cys Ser Gln Pro Pro Cys Thr Pro Cys Cys Tyr
            275                 280                 285

Glu Lys Glu Pro Glu Glu Thr Leu Arg Met Leu Glu Asp Asn Val Met
        290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
            325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
            355                 360                 365

Gly Thr Leu Lys Ile Gln Val Ser Leu Gln Ile Gly Ile Lys Thr Asp
            370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
            435                 440                 445

Ser Cys Thr His Pro Phe His His Asp Pro Val Ile Gly Arg Glu
            450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
            515                 520                 525

Gly Gly Ser Asn Glu Gly Leu Thr Thr Thr Asp Lys Val Ile Asn Asn
            530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
            595                 600                 605

Ile Met Leu Leu Tyr Pro Asp His Pro Thr Leu Leu Ser Tyr Arg Asn
            610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670
```

```
Ala His Gly His Pro His Glu Ile Ile Leu Tyr Tyr Glu Leu Tyr
            675                 680                 685

Pro Thr Met Thr Val Val Val Ser Val Ala Thr Phe Ile Leu Leu
        690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
                740                 745                 750

Glu Ala Ala Ile Tyr Leu Trp Asn Glu Gln Pro Leu Phe Trp Leu
            755                 760                 765

Gln Ala Leu Ile Pro Leu Ala Ala Leu Ile Val Leu Cys Asn Cys Leu
        770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
            835                 840                 845

Pro Thr Leu Ser Leu Asp Tyr Ile Thr Cys Glu Tyr Lys Thr Val Ile
        850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
            885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro Phe Gly Ala Gly Arg Pro Gly Gln
        995                 1000                1005

Phe Gly Asp Ile Gln Ser Arg Thr Pro Glu Ser Lys Asp Val Tyr
    1010                1015                1020

Ala Asn Thr Gln Leu Val Leu Gln Arg Pro Ala Ala Gly Thr Val
    1025                1030                1035

His Val Pro Tyr Ser Gln Ala Pro Ser Gly Phe Lys Tyr Trp Leu
    1040                1045                1050

Lys Glu Arg Gly Ala Ser Leu Gln His Thr Ala Pro Phe Gly Cys
    1055                1060                1065

Gln Ile Ala Thr Asn Pro Val Arg Ala Val Asn Cys Ala Val Gly
    1070                1075                1080
```

-continued

```
Asn Met Pro Ile Ser Ile Asp Ile Pro Glu Ala Ala Phe Thr Arg
    1085                1090                1095

Val Val Asp Ala Pro Ser Leu Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Ala Ala Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 25
<211> LENGTH: 1248
<212> TYPE: PRT
<213> ORGANISM: Artificial Sequence
<220> FEATURE:
<223> OTHER INFORMATION: proteins C-E3-E2-6K-E1 strain 06.27

<400> SEQUENCE: 25

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
                20                  25                  30

Arg Pro Gln Arg Gln Ala Gly Gln Leu Ala Gln Leu Ile Ser Ala Val
            35                  40                  45

Asn Lys Leu Thr Met Arg Ala Val Pro Gln Gln Lys Pro Arg Arg Asn
50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190
```

```
Ala Val Gln Tyr Ser Gly Gly Arg Phe Thr Ile Pro Thr Gly Ala Gly
            195                 200                 205
Lys Pro Gly Asp Ser Gly Arg Pro Ile Phe Asp Asn Lys Gly Arg Val
210                 215                 220
Val Ala Ile Val Leu Gly Gly Ala Asn Glu Gly Ala Arg Thr Ala Leu
225                 230                 235                 240
Ser Val Val Thr Trp Asn Lys Asp Ile Val Thr Lys Ile Thr Pro Glu
            245                 250                 255
Gly Ala Glu Glu Trp Ser Leu Ala Ile Pro Val Met Cys Leu Leu Ala
            260                 265                 270
Asn Thr Thr Phe Pro Cys Ser Gln Pro Pro Cys Thr Pro Cys Cys Tyr
            275                 280                 285
Glu Lys Glu Pro Glu Glu Thr Leu Arg Met Leu Glu Asp Asn Val Met
290                 295                 300
Arg Pro Gly Tyr Tyr Gln Leu Leu Gln Ala Ser Leu Thr Cys Ser Pro
305                 310                 315                 320
His Arg Gln Arg Arg Ser Thr Lys Asp Asn Phe Asn Val Tyr Lys Ala
            325                 330                 335
Thr Arg Pro Tyr Leu Ala His Cys Pro Asp Cys Gly Glu Gly His Ser
            340                 345                 350
Cys His Ser Pro Val Ala Leu Glu Arg Ile Arg Asn Glu Ala Thr Asp
            355                 360                 365
Gly Thr Leu Lys Ile Gln Val Ser Leu Gln Ile Gly Ile Lys Thr Asp
            370                 375                 380
Asp Ser His Asp Trp Thr Lys Leu Arg Tyr Met Asp Asn His Met Pro
385                 390                 395                 400
Ala Asp Ala Glu Arg Ala Gly Leu Phe Val Arg Thr Ser Ala Pro Cys
            405                 410                 415
Thr Ile Thr Gly Thr Met Gly His Phe Ile Leu Ala Arg Cys Pro Lys
            420                 425                 430
Gly Glu Thr Leu Thr Val Gly Phe Thr Asp Ser Arg Lys Ile Ser His
            435                 440                 445
Ser Cys Thr His Pro Phe His His Asp Pro Pro Val Ile Gly Arg Glu
450                 455                 460
Lys Phe His Ser Arg Pro Gln His Gly Lys Glu Leu Pro Cys Ser Thr
465                 470                 475                 480
Tyr Val Gln Ser Thr Ala Ala Thr Thr Glu Glu Ile Glu Val His Met
            485                 490                 495
Pro Pro Asp Thr Pro Asp Arg Thr Leu Met Ser Gln Gln Ser Gly Asn
            500                 505                 510
Val Lys Ile Thr Val Asn Gly Gln Thr Val Arg Tyr Lys Cys Asn Cys
            515                 520                 525
Gly Gly Ser Asn Glu Gly Leu Thr Thr Thr Asp Lys Val Ile Asn Asn
            530                 535                 540
Cys Lys Val Asp Gln Cys His Ala Ala Val Thr Asn His Lys Lys Trp
545                 550                 555                 560
Gln Tyr Asn Ser Pro Leu Val Pro Arg Asn Ala Glu Leu Gly Asp Arg
            565                 570                 575
Lys Gly Lys Ile His Ile Pro Phe Pro Leu Ala Asn Val Thr Cys Arg
            580                 585                 590
Val Pro Lys Ala Arg Asn Pro Thr Val Thr Tyr Gly Lys Asn Gln Val
            595                 600                 605
Ile Met Leu Leu Tyr Pro Asp His Pro Thr Leu Leu Ser Tyr Arg Asn
```

```
                610              615                620
Met Gly Glu Glu Pro Asn Tyr Gln Glu Glu Trp Val Met His Lys Lys
625                 630                 635                 640

Glu Val Val Leu Thr Val Pro Thr Gly Leu Glu Val Thr Trp Gly
            645                 650                 655

Asn Asn Glu Pro Tyr Lys Tyr Trp Pro Gln Leu Ser Thr Asn Gly Thr
                660                 665                 670

Ala His Gly His Pro His Glu Ile Ile Leu Tyr Tyr Glu Leu Tyr
            675                 680                 685

Pro Thr Met Thr Val Val Val Ser Val Ala Thr Phe Ile Leu Leu
        690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
            755                 760                 765

Gln Ala Leu Ile Pro Leu Ala Ala Leu Ile Val Leu Cys Asn Cys Leu
770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
            805                 810                 815

Pro Asn Thr Val Gly Val Pro Tyr Lys Thr Leu Val Asn Arg Pro Gly
                820                 825                 830

Tyr Ser Pro Met Val Leu Glu Met Glu Leu Leu Ser Val Thr Leu Glu
            835                 840                 845

Pro Thr Leu Ser Leu Asp Tyr Ile Thr Cys Glu Tyr Lys Thr Val Ile
        850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
            915                 920                 925

Ser Ala Tyr Arg Ala His Thr Ala Ser Ala Ser Ala Lys Leu Arg Val
        930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro Phe Gly Ala Gly Arg Pro Gly Gln
        995                 1000                1005

Phe Gly Asp Ile Gln Ser Arg Thr Pro Glu Ser Lys Asp Val Tyr
    1010                1015                1020

Ala Asn Thr Gln Leu Val Leu Gln Arg Pro Ala Val Gly Thr Val
    1025                1030                1035
```

His Val Pro Tyr Ser Gln Ala Pro Ser Gly Phe Lys Tyr Trp Leu
1040                1045                1050

Lys Glu Arg Gly Ala Ser Leu Gln His Thr Ala Pro Phe Gly Cys
    1055                1060                1065

Gln Ile Ala Thr Asn Pro Val Arg Ala Val Asn Cys Ala Val Gly
1070                1075                1080

Asn Met Pro Ile Ser Ile Asp Ile Pro Glu Ala Ala Phe Thr Arg
    1085                1090                1095

Val Val Asp Ala Pro Ser Leu Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Ala Ala Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 26
<211> LENGTH: 1248
<212> TYPE: PRT
<213> ORGANISM: Artificial Sequence
<220> FEATURE:
<223> OTHER INFORMATION: proteins C-E3-E2-6K-E1 strain 06.21

<400> SEQUENCE: 26

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Gln Ala Pro Gln Asn Asn
65                  70                  75                  80

Thr Asn Gln Lys Lys Gln Pro Pro Lys Lys Pro Ala Gln Lys Lys
            85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

```
Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
            195                 200                 205

Lys Pro Gly Asp Ser Gly Arg Pro Ile Phe Asp Asn Lys Gly Arg Val
210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
            275                 280                 285

Glu Lys Glu Pro Glu Thr Leu Arg Met Leu Glu Asp Asn Val Met
290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
            355                 360                 365

Gly Thr Leu Lys Ile Gln Val Ser Leu Gln Ile Gly Ile Lys Thr Asp
370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
            435                 440                 445

Ser Cys Thr His Pro Phe His His Asp Pro Pro Val Ile Gly Arg Glu
450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Ser Gly Asn
                500                 505                 510

Val Lys Ile Thr Val Asn Gly Gln Thr Val Arg Tyr Lys Cys Asn Cys
            515                 520                 525

Gly Gly Ser Asn Glu Gly Leu Thr Thr Thr Asp Lys Val Ile Asn Asn
            530                 535                 540

Cys Lys Val Asp Gln Cys His Ala Ala Val Thr Asn His Lys Lys Trp
545                 550                 555                 560
```

```
Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Glu Leu Tyr
        675                 680                 685

Pro Thr Met Thr Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
```

-continued

```
                980               985               990
Val Tyr Asn Met Asp Tyr Pro Pro  Phe Gly Ala Gly Arg  Pro Gly Gln
                    995              1000              1005

Phe Gly Asp Ile Gln Ser Arg  Thr Pro Glu Ser Lys  Asp Val Tyr
        1010              1015              1020

Ala Asn Thr Gln Leu Val Leu  Gln Arg Pro Ala Val  Gly Thr Val
    1025              1030              1035

His Val Pro Tyr Ser Gln Ala  Pro Ser Gly Phe Lys  Tyr Trp Leu
    1040              1045              1050

Lys Glu Arg Gly Ala Ser Leu  Gln His Thr Ala Pro  Phe Gly Cys
    1055              1060              1065

Gln Ile Ala Thr Asn Pro Val  Arg Ala Val Asn Cys  Ala Val Gly
    1070              1075              1080

Asn Met Pro Ile Ser Ile Asp  Ile Pro Glu Ala Ala  Phe Thr Arg
    1085              1090              1095

Val Val Asp Ala Pro Ser Leu  Thr Asp Met Ser Cys  Glu Val Pro
    1100              1105              1110

Ala Cys Thr His Ser Ser Asp  Phe Gly Gly Val Ala  Ile Ile Lys
    1115              1120              1125

Tyr Ala Ala Ser Lys Lys Gly  Lys Cys Ala Val His  Ser Met Thr
    1130              1135              1140

Asn Ala Val Thr Ile Arg Glu  Ala Glu Ile Glu Val  Glu Gly Asn
    1145              1150              1155

Ser Gln Leu Gln Ile Ser Phe  Ser Thr Ala Leu Ala  Ser Ala Glu
    1160              1165              1170

Phe Arg Val Gln Val Cys Ser  Thr Gln Val His Cys  Ala Ala Glu
    1175              1180              1185

Cys His Pro Pro Lys Asp His  Ile Val Asn Tyr Pro  Ala Ser His
    1190              1195              1200

Thr Thr Leu Gly Val Gln Asp  Ile Ser Ala Thr Ala  Met Ser Trp
    1205              1210              1215

Val Gln Lys Ile Thr Gly Gly  Val Gly Leu Val Val  Ala Val Ala
    1220              1225              1230

Ala Leu Ile Leu Ile Val Val  Leu Cys Val Ser Phe  Ser Arg His
    1235              1240              1245

<210> SEQ ID NO 27
<211> LENGTH: 3747
<212> TYPE: DNA
<213> ORGANISM: Artificial Sequence
<220> FEATURE:
<223> OTHER INFORMATION: proteins C-E3-E2-6K-E1 strain 06.49 (GenBank:
      AM258994.1)
<220> FEATURE:
<221> NAME/KEY: CDS
<222> LOCATION: (1)..(3747)

<400> SEQUENCE: 27 atg gag ttc atc cca acc caa act ttt tac aat agg agg tac cag cct        48
Met Glu Phe Ile Pro Thr Gln Thr Phe Tyr Asn Arg Arg Tyr Gln Pro
1               5                   10                  15 cga ccc tgg act ccg cgc cct act atc caa gtc atc agg ccc aga ccg        96
Arg Pro Trp Thr Pro Arg Pro Thr Ile Gln Val Ile Arg Pro Arg Pro
            20                  25                  30 cgc cct cag agg caa gct ggg caa ctt gcc cag ctg atc tca gca gtt       144
Arg Pro Gln Arg Gln Ala Gly Gln Leu Ala Gln Leu Ile Ser Ala Val
        35                  40                  45
```

```
aat aaa ctg aca atg cgc gcg gta ccc caa cag aag cca cgc agg aat        192
Asn Lys Leu Thr Met Arg Ala Val Pro Gln Gln Lys Pro Arg Arg Asn
    50                  55                  60 cgg aag aat aag aag caa aag caa aaa caa cag gcg cca caa aac aac        240
Arg Lys Asn Lys Lys Gln Lys Gln Lys Gln Gln Ala Pro Gln Asn Asn
65                  70                  75                  80 aca aat caa aag aag cag cca cct aaa aag aaa ccg gct caa aag aaa        288
Thr Asn Gln Lys Lys Gln Pro Pro Lys Lys Lys Pro Ala Gln Lys Lys
                85                  90                  95 aag aag ccg ggc cgc aga gag agg atg tgc atg aaa atc gaa aat gat        336
Lys Lys Pro Gly Arg Arg Glu Arg Met Cys Met Lys Ile Glu Asn Asp
                100                 105                 110 tgt att ttc gaa gtc aag cac gaa ggt aag gta aca ggt tac gcg tgc        384
Cys Ile Phe Glu Val Lys His Glu Gly Lys Val Thr Gly Tyr Ala Cys
            115                 120                 125 ctg gtg ggg gac aaa gta atg aaa cca gca cac gta aag ggg acc atc        432
Leu Val Gly Asp Lys Val Met Lys Pro Ala His Val Lys Gly Thr Ile
        130                 135                 140 gat aac gcg gac ctg gcc aaa ctg gcc ttt aag cgg tca tct aag tat        480
Asp Asn Ala Asp Leu Ala Lys Leu Ala Phe Lys Arg Ser Ser Lys Tyr
145                 150                 155                 160 gac ctt gaa tgc gcg cag ata ccc gtg cac atg aag tcc gac gct tcg        528
Asp Leu Glu Cys Ala Gln Ile Pro Val His Met Lys Ser Asp Ala Ser
                165                 170                 175 aag ttc acc cat gag aaa ccg gag ggg tac tac aac tgg cac cac gga        576
Lys Phe Thr His Glu Lys Pro Glu Gly Tyr Tyr Asn Trp His His Gly
                180                 185                 190 gca gta cag tac tca gga ggc cgg ttc acc atc cct aca ggt gct ggc        624
Ala Val Gln Tyr Ser Gly Gly Arg Phe Thr Ile Pro Thr Gly Ala Gly
            195                 200                 205 aaa cca ggg gac agc ggc aga ccg atc ttc gac aac aag gga cgc gtg        672
Lys Pro Gly Asp Ser Gly Arg Pro Ile Phe Asp Asn Lys Gly Arg Val
        210                 215                 220 gtg gcc ata gtc tta gga gga gct aat gaa gga gcc cgt aca gcc ctc        720
Val Ala Ile Val Leu Gly Gly Ala Asn Glu Gly Ala Arg Thr Ala Leu
225                 230                 235                 240 tcg gtg gtg acc tgg aat aaa gac att gtc act aaa atc acc ccc gag        768
Ser Val Val Thr Trp Asn Lys Asp Ile Val Thr Lys Ile Thr Pro Glu
                245                 250                 255 ggg gcc gaa gag tgg agt ctt gcc atc cca gtt atg tgc ctg ttg gca        816
Gly Ala Glu Glu Trp Ser Leu Ala Ile Pro Val Met Cys Leu Leu Ala
                260                 265                 270 aac acc acg ttc ccc tgc tcc cag ccc cct tgc acg ccc tgc tgc tac        864
Asn Thr Thr Phe Pro Cys Ser Gln Pro Pro Cys Thr Pro Cys Cys Tyr
            275                 280                 285 gaa aag gaa ccg gag gaa acc cta cgc atg ctt gag gac aac gtc atg        912
Glu Lys Glu Pro Glu Glu Thr Leu Arg Met Leu Glu Asp Asn Val Met
        290                 295                 300 aga cct ggg tac tat cag ctg cta caa gca tcc tta aca tgt tct ccc        960
Arg Pro Gly Tyr Tyr Gln Leu Leu Gln Ala Ser Leu Thr Cys Ser Pro
305                 310                 315                 320 cac cgc cag cga cgc agc acc aag gac aac ttc aat gtc tat aaa gcc        1008
His Arg Gln Arg Arg Ser Thr Lys Asp Asn Phe Asn Val Tyr Lys Ala
                325                 330                 335 aca aga cca tac tta gct cac tgt ccc gac tgt gga gaa ggg cac tcg        1056
Thr Arg Pro Tyr Leu Ala His Cys Pro Asp Cys Gly Glu Gly His Ser
                340                 345                 350 tgc cat agt ccc gta gca cta gaa cgc atc aga aat gaa gcg aca gac        1104
Cys His Ser Pro Val Ala Leu Glu Arg Ile Arg Asn Glu Ala Thr Asp
            355                 360                 365
```

```
ggg acg ctg aaa atc cag gtc tcc ttg caa atc gga ata aag acg gat    1152
Gly Thr Leu Lys Ile Gln Val Ser Leu Gln Ile Gly Ile Lys Thr Asp
        370                 375                 380 gac agc cac gat tgg acc aag ctg cgt tat atg gac aac cac atg cca    1200
Asp Ser His Asp Trp Thr Lys Leu Arg Tyr Met Asp Asn His Met Pro
385                 390                 395                 400 gca gac gca gag agg gcg ggg cta ttt gta aga aca tca gca ccg tgt    1248
Ala Asp Ala Glu Arg Ala Gly Leu Phe Val Arg Thr Ser Ala Pro Cys
                405                 410                 415 acg att act gga aca atg gga cac ttc atc ctg gcc cga tgt cca aaa    1296
Thr Ile Thr Gly Thr Met Gly His Phe Ile Leu Ala Arg Cys Pro Lys
                    420                 425                 430 ggg gaa act ctg acg gtg gga ttc act gac agt agg aag att agt cac    1344
Gly Glu Thr Leu Thr Val Gly Phe Thr Asp Ser Arg Lys Ile Ser His
                435                 440                 445 tca tgt acg cac cca ttt cac cac gac cct cct gtg ata ggt cgg gaa    1392
Ser Cys Thr His Pro Phe His His Asp Pro Pro Val Ile Gly Arg Glu
        450                 455                 460 aaa ttc cat tcc cga ccg cag cac ggt aaa gag cta cct tgc agc acg    1440
Lys Phe His Ser Arg Pro Gln His Gly Lys Glu Leu Pro Cys Ser Thr
465                 470                 475                 480 tac gtg cag agc acc gcc gca act acc gag gag ata gag gta cac atg    1488
Tyr Val Gln Ser Thr Ala Ala Thr Thr Glu Glu Ile Glu Val His Met
                485                 490                 495 ccc cca gac acc cct gat cgc aca tta atg tca caa cag tcc ggc aac    1536
Pro Pro Asp Thr Pro Asp Arg Thr Leu Met Ser Gln Gln Ser Gly Asn
                    500                 505                 510 gta aag atc aca gtc aat ggc cag acg gtg cgg tac aag tgt aat tgc    1584
Val Lys Ile Thr Val Asn Gly Gln Thr Val Arg Tyr Lys Cys Asn Cys
                515                 520                 525 ggt ggc tca aat gaa gga cta aca act aca gac aaa gtg att aat aac    1632
Gly Gly Ser Asn Glu Gly Leu Thr Thr Thr Asp Lys Val Ile Asn Asn
        530                 535                 540 tgc aag gtt gat caa tgt cat gcc gcg gtc acc aat cac aaa aag tgg    1680
Cys Lys Val Asp Gln Cys His Ala Ala Val Thr Asn His Lys Lys Trp
545                 550                 555                 560 cag tat aac tcc cct ctg gtc ccg cgt aat gct gaa ctt ggg gac cga    1728
Gln Tyr Asn Ser Pro Leu Val Pro Arg Asn Ala Glu Leu Gly Asp Arg
                565                 570                 575 aaa gga aaa att cac atc ccg ttt ccg ctg gca aat gta aca tgc agg    1776
Lys Gly Lys Ile His Ile Pro Phe Pro Leu Ala Asn Val Thr Cys Arg
                    580                 585                 590 gtg cct aaa gca agg aac ccc acc gtg acg tac ggg aaa aac caa gtc    1824
Val Pro Lys Ala Arg Asn Pro Thr Val Thr Tyr Gly Lys Asn Gln Val
                595                 600                 605 atc atg cta ctg tat cct gac cac cca aca ctc ctg tcc tac cgg aat    1872
Ile Met Leu Leu Tyr Pro Asp His Pro Thr Leu Leu Ser Tyr Arg Asn
        610                 615                 620 atg gga gaa gaa cca aac tat caa gaa gag tgg gtg atg cat aag aag    1920
Met Gly Glu Glu Pro Asn Tyr Gln Glu Glu Trp Val Met His Lys Lys
625                 630                 635                 640 gaa gtc gtg cta acc gtg ccg act gaa ggg ctc gag gtc acg tgg ggc    1968
Glu Val Val Leu Thr Val Pro Thr Glu Gly Leu Glu Val Thr Trp Gly
                645                 650                 655 aac aac gag ccg tat aag tat tgg ccg cag tta tct aca aac ggt aca    2016
Asn Asn Glu Pro Tyr Lys Tyr Trp Pro Gln Leu Ser Thr Asn Gly Thr
                    660                 665                 670 gcc cat ggc cac ccg cac gag ata att ctg tat tat tat gag ctg tac    2064
Ala His Gly His Pro His Glu Ile Ile Leu Tyr Tyr Tyr Glu Leu Tyr
```

-continued

| | | | 675 | | | | 680 | | | | 685 | | | | |
|---|---|---|---|---|---|---|---|---|---|---|---|---|---|---|---|
| ccc | act | atg | act | gta | gta | gtt | gtg | tca | gtg | gcc | acg | ttc | ata | ctc | ctg | 2112 |
| Pro | Thr | Met | Thr | Val | Val | Val | Val | Ser | Val | Ala | Thr | Phe | Ile | Leu | Leu | |
| | 690 | | | | 695 | | | | 700 | | | | | | | |

| tcg | atg | gtg | ggt | atg | gca | gcg | ggg | atg | tgc | atg | tgt | gca | cga | cgc | aga | 2160 |
|---|---|---|---|---|---|---|---|---|---|---|---|---|---|---|---|---|
| Ser | Met | Val | Gly | Met | Ala | Ala | Gly | Met | Cys | Met | Cys | Ala | Arg | Arg | Arg | |
| 705 | | | | 710 | | | | | 715 | | | | | 720 | | |

| tgc | atc | aca | ccg | tat | gaa | ctg | aca | cca | gga | gct | acc | gtc | cct | ttc | ctg | 2208 |
|---|---|---|---|---|---|---|---|---|---|---|---|---|---|---|---|---|
| Cys | Ile | Thr | Pro | Tyr | Glu | Leu | Thr | Pro | Gly | Ala | Thr | Val | Pro | Phe | Leu | |
| | | | | 725 | | | | | 730 | | | | | 735 | | |

| ctt | agc | cta | ata | tgc | tgc | atc | aga | aca | gct | aaa | gcg | gcc | aca | tac | caa | 2256 |
|---|---|---|---|---|---|---|---|---|---|---|---|---|---|---|---|---|
| Leu | Ser | Leu | Ile | Cys | Cys | Ile | Arg | Thr | Ala | Lys | Ala | Ala | Thr | Tyr | Gln | |
| | | | 740 | | | | | 745 | | | | | 750 | | | |

| gag | gct | gcg | ata | tac | ctg | tgg | aac | gag | cag | caa | cct | ttg | ttt | tgg | cta | 2304 |
|---|---|---|---|---|---|---|---|---|---|---|---|---|---|---|---|---|
| Glu | Ala | Ala | Ile | Tyr | Leu | Trp | Asn | Glu | Gln | Gln | Pro | Leu | Phe | Trp | Leu | |
| | | | | 755 | | | | | 760 | | | | | 765 | | |

| caa | gcc | ctt | att | ccg | ctg | gca | gcc | ctg | att | gtt | cta | tgc | aac | tgt | ctg | 2352 |
|---|---|---|---|---|---|---|---|---|---|---|---|---|---|---|---|---|
| Gln | Ala | Leu | Ile | Pro | Leu | Ala | Ala | Leu | Ile | Val | Leu | Cys | Asn | Cys | Leu | |
| 770 | | | | | 775 | | | | | 780 | | | | | | |

| aga | ctc | tta | cca | tgc | tgc | tgt | aaa | acg | ttg | gct | ttt | tta | gcc | gta | atg | 2400 |
|---|---|---|---|---|---|---|---|---|---|---|---|---|---|---|---|---|
| Arg | Leu | Leu | Pro | Cys | Cys | Cys | Lys | Thr | Leu | Ala | Phe | Leu | Ala | Val | Met | |
| 785 | | | | 790 | | | | | 795 | | | | | 800 | | |

| agc | gtc | ggt | gcc | cac | act | gtg | agc | gcg | tac | gaa | cac | gta | aca | gtg | atc | 2448 |
|---|---|---|---|---|---|---|---|---|---|---|---|---|---|---|---|---|
| Ser | Val | Gly | Ala | His | Thr | Val | Ser | Ala | Tyr | Glu | His | Val | Thr | Val | Ile | |
| | | | | 805 | | | | | 810 | | | | | 815 | | |

| ccg | aac | acg | gtg | gga | gta | ccg | tat | aag | act | cta | gtc | aat | aga | cct | ggc | 2496 |
|---|---|---|---|---|---|---|---|---|---|---|---|---|---|---|---|---|
| Pro | Asn | Thr | Val | Gly | Val | Pro | Tyr | Lys | Thr | Leu | Val | Asn | Arg | Pro | Gly | |
| | | | 820 | | | | | 825 | | | | | 830 | | | |

| tac | agc | ccc | atg | gta | ttg | gag | atg | gaa | cta | ctg | tca | act | ttg | gag | | 2544 |
|---|---|---|---|---|---|---|---|---|---|---|---|---|---|---|---|---|
| Tyr | Ser | Pro | Met | Val | Leu | Glu | Met | Glu | Leu | Leu | Ser | Val | Thr | Leu | Glu | |
| | | 835 | | | | | 840 | | | | | 845 | | | | |

| cca | aca | cta | tcg | ctt | gat | tac | atc | acg | tgc | gag | tac | aaa | acc | gtc | atc | 2592 |
|---|---|---|---|---|---|---|---|---|---|---|---|---|---|---|---|---|
| Pro | Thr | Leu | Ser | Leu | Asp | Tyr | Ile | Thr | Cys | Glu | Tyr | Lys | Thr | Val | Ile | |
| 850 | | | | | 855 | | | | | 860 | | | | | | |

| ccg | tct | ccg | tac | gtg | aag | tgc | tgc | ggt | aca | gca | gag | tgc | aag | gac | aaa | 2640 |
|---|---|---|---|---|---|---|---|---|---|---|---|---|---|---|---|---|
| Pro | Ser | Pro | Tyr | Val | Lys | Cys | Cys | Gly | Thr | Ala | Glu | Cys | Lys | Asp | Lys | |
| 865 | | | | 870 | | | | | 875 | | | | | 880 | | |

| aac | cta | cct | gac | tac | agc | tgt | aag | gtc | ttc | acc | ggc | gtc | tac | cca | ttt | 2688 |
|---|---|---|---|---|---|---|---|---|---|---|---|---|---|---|---|---|
| Asn | Leu | Pro | Asp | Tyr | Ser | Cys | Lys | Val | Phe | Thr | Gly | Val | Tyr | Pro | Phe | |
| | | | | 885 | | | | | 890 | | | | | 895 | | |

| atg | tgg | ggc | ggc | gcc | tac | tgc | ttc | tgc | gac | gct | gaa | aac | acg | cag | ttg | 2736 |
|---|---|---|---|---|---|---|---|---|---|---|---|---|---|---|---|---|
| Met | Trp | Gly | Gly | Ala | Tyr | Cys | Phe | Cys | Asp | Ala | Glu | Asn | Thr | Gln | Leu | |
| | | | 900 | | | | | 905 | | | | | 910 | | | |

| agc | gaa | gca | cac | gtg | gag | aag | tcc | gaa | tca | tgc | aaa | aca | gaa | ttt | gca | 2784 |
|---|---|---|---|---|---|---|---|---|---|---|---|---|---|---|---|---|
| Ser | Glu | Ala | His | Val | Glu | Lys | Ser | Glu | Ser | Cys | Lys | Thr | Glu | Phe | Ala | |
| | | 915 | | | | | 920 | | | | | 925 | | | | |

| tca | gca | tac | agg | gct | cat | acc | gca | tct | gca | tca | gct | aag | ctc | cgc | gtc | 2832 |
|---|---|---|---|---|---|---|---|---|---|---|---|---|---|---|---|---|
| Ser | Ala | Tyr | Arg | Ala | His | Thr | Ala | Ser | Ala | Ser | Ala | Lys | Leu | Arg | Val | |
| | 930 | | | | | 935 | | | | | 940 | | | | | |

| ctt | tac | caa | gga | aat | aac | atc | act | gta | act | gcc | tat | gca | aac | ggc | gac | 2880 |
|---|---|---|---|---|---|---|---|---|---|---|---|---|---|---|---|---|
| Leu | Tyr | Gln | Gly | Asn | Asn | Ile | Thr | Val | Thr | Ala | Tyr | Ala | Asn | Gly | Asp | |
| 945 | | | | | 950 | | | | | 955 | | | | | 960 | |

| cat | gcc | gtc | aca | gtt | aag | gac | gcc | aaa | ttc | att | gtg | ggg | cca | atg | tct | 2928 |
|---|---|---|---|---|---|---|---|---|---|---|---|---|---|---|---|---|
| His | Ala | Val | Thr | Val | Lys | Asp | Ala | Lys | Phe | Ile | Val | Gly | Pro | Met | Ser | |
| | | | | 965 | | | | | 970 | | | | | 975 | | |

| tca | gcc | tgg | aca | cct | ttc | gac | aac | aaa | att | gtg | gtg | tac | aaa | ggt | gac | 2976 |
|---|---|---|---|---|---|---|---|---|---|---|---|---|---|---|---|---|
| Ser | Ala | Trp | Thr | Pro | Phe | Asp | Asn | Lys | Ile | Val | Val | Tyr | Lys | Gly | Asp | |
| | | | 980 | | | | | 985 | | | | | 990 | | | |

| gtc | tat | aac | atg | gac | tac | ccg | ccc | | ttt | ggc | gca | gga | aga | | cca | gga | caa | 3024 |

```
                Val Tyr Asn Met Asp Tyr Pro Pro Phe Gly Ala Gly Arg Pro Gly Gln
                            995                 1000                1005 ttt ggc gat atc caa agt cgc aca cct gag agt aaa gac gtc tat           3069
Phe Gly Asp Ile Gln Ser Arg Thr Pro Glu Ser Lys Asp Val Tyr
1010                1015                1020 gct aat aca caa ctg gta ctg cag aga ccg gct gtg ggt acg gta           3114
Ala Asn Thr Gln Leu Val Leu Gln Arg Pro Ala Val Gly Thr Val
    1025                1030                1035 cac gtg cca tac tct cag gca cca tct ggc ttt aag tat tgg cta           3159
His Val Pro Tyr Ser Gln Ala Pro Ser Gly Phe Lys Tyr Trp Leu
1040                1045                1050 aaa gaa cgc ggg gcg tcg ctg cag cac aca gca cca ttt ggc tgc           3204
Lys Glu Arg Gly Ala Ser Leu Gln His Thr Ala Pro Phe Gly Cys
    1055                1060                1065 caa ata gca aca aac ccg gta aga gcg gtg aac tgc gcc gta ggg           3249
Gln Ile Ala Thr Asn Pro Val Arg Ala Val Asn Cys Ala Val Gly
1070                1075                1080 aac atg ccc atc tcc atc gac ata ccg gaa gcg gcc ttc act agg           3294
Asn Met Pro Ile Ser Ile Asp Ile Pro Glu Ala Ala Phe Thr Arg
    1085                1090                1095 gtc gtc gac gcg ccc tct tta acg gac atg tcg tgc gag gta cca           3339
Val Val Asp Ala Pro Ser Leu Thr Asp Met Ser Cys Glu Val Pro
1100                1105                1110 gcc tgc acc cat tcc tca gac ttt ggg ggc gtc gcc att att aaa           3384
Ala Cys Thr His Ser Ser Asp Phe Gly Gly Val Ala Ile Ile Lys
    1115                1120                1125 tat gca gcc agc aag aaa ggc aag tgt gcg gtg cat tcg atg act           3429
Tyr Ala Ala Ser Lys Lys Gly Lys Cys Ala Val His Ser Met Thr
1130                1135                1140 aac gcc gtc act att cgg gaa gct gag ata gaa gtt gaa ggg aat           3474
Asn Ala Val Thr Ile Arg Glu Ala Glu Ile Glu Val Glu Gly Asn
    1145                1150                1155 tct cag ctg caa atc tct ttc tcg acg gcc tta gcc agc gcc gaa           3519
Ser Gln Leu Gln Ile Ser Phe Ser Thr Ala Leu Ala Ser Ala Glu
1160                1165                1170 ttc cgc gta caa gtc tgt tct aca caa gta cac tgt gca gcc gag           3564
Phe Arg Val Gln Val Cys Ser Thr Gln Val His Cys Ala Ala Glu
    1175                1180                1185 tgc cac ccc ccg aag gac cac ata gtc aac tac ccg gcg tca cat           3609
Cys His Pro Pro Lys Asp His Ile Val Asn Tyr Pro Ala Ser His
1190                1195                1200 acc acc ctc ggg gtc cag gac atc tcc gct acg gcg atg tca tgg           3654
Thr Thr Leu Gly Val Gln Asp Ile Ser Ala Thr Ala Met Ser Trp
    1205                1210                1215 gtg cag aag atc acg gga ggt gtg gga ctg gtt gtt gct gtt gcc           3699
Val Gln Lys Ile Thr Gly Gly Val Gly Leu Val Val Ala Val Ala
1220                1225                1230 gca ctg att cta atc gtg gtg cta tgc gtg tcg ttc agc agg cac           3744
Ala Leu Ile Leu Ile Val Val Leu Cys Val Ser Phe Ser Arg His
    1235                1240                1245 taa                                                                   3747

<210> SEQ ID NO 28
<211> LENGTH: 1248
<212> TYPE: PRT
<213> ORGANISM: Artificial Sequence
<220> FEATURE:
<223> OTHER INFORMATION: Synthetic Construct

<400> SEQUENCE: 28
```

-continued

```
Met Glu Phe Ile Pro Thr Gln Thr Phe Tyr Asn Arg Arg Tyr Gln Pro
 1               5                  10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
         35                  40                  45

Asn Lys Leu Thr Met Arg Ala Val Pro Gln Gln Lys Pro Arg Arg Asn
 50                  55                  60

Arg Lys Asn Lys Lys Gln Lys Gln Lys Gln Ala Pro Gln Asn Asn
 65                  70                  75                  80

Thr Asn Gln Lys Lys Gln Pro Pro Lys Lys Pro Ala Gln Lys Lys
                 85                  90                  95

Lys Lys Pro Gly Arg Arg Glu Arg Met Cys Met Lys Ile Glu Asn Asp
             100                 105                 110

Cys Ile Phe Glu Val Lys His Glu Gly Lys Val Thr Gly Tyr Ala Cys
             115                 120                 125

Leu Val Gly Asp Lys Val Met Lys Pro Ala His Val Lys Gly Thr Ile
         130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                 165                 170                 175

Lys Phe Thr His Glu Lys Pro Glu Gly Tyr Tyr Asn Trp His His Gly
             180                 185                 190

Ala Val Gln Tyr Ser Gly Gly Arg Phe Thr Ile Pro Thr Gly Ala Gly
         195                 200                 205

Lys Pro Gly Asp Ser Gly Arg Pro Ile Phe Asp Asn Lys Gly Arg Val
     210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                 245                 250                 255

Gly Ala Glu Glu Trp Ser Leu Ala Ile Pro Val Met Cys Leu Leu Ala
             260                 265                 270

Asn Thr Thr Phe Pro Cys Ser Gln Pro Pro Cys Thr Pro Cys Cys Tyr
         275                 280                 285

Glu Lys Glu Pro Glu Glu Thr Leu Arg Met Leu Glu Asp Asn Val Met
     290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                 325                 330                 335

Thr Arg Pro Tyr Leu Ala His Cys Pro Asp Cys Gly Glu Gly His Ser
             340                 345                 350

Cys His Ser Pro Val Ala Leu Glu Arg Ile Arg Asn Glu Ala Thr Asp
         355                 360                 365

Gly Thr Leu Lys Ile Gln Val Ser Leu Gln Ile Gly Ile Lys Thr Asp
     370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                 405                 410                 415

Thr Ile Thr Gly Thr Met Gly His Phe Ile Leu Ala Arg Cys Pro Lys
```

```
                420                 425                 430
Gly Glu Thr Leu Thr Val Gly Phe Thr Asp Ser Arg Lys Ile Ser His
            435                 440                 445
Ser Cys Thr His Pro Phe His His Asp Pro Val Ile Gly Arg Glu
    450                 455                 460
Lys Phe His Ser Arg Pro Gln His Gly Lys Glu Leu Pro Cys Ser Thr
465                 470                 475                 480
Tyr Val Gln Ser Thr Ala Ala Thr Thr Glu Glu Ile Glu Val His Met
            485                 490                 495
Pro Pro Asp Thr Pro Asp Arg Thr Leu Met Ser Gln Gln Ser Gly Asn
            500                 505                 510
Val Lys Ile Thr Val Asn Gly Gln Thr Val Arg Tyr Lys Cys Asn Cys
            515                 520                 525
Gly Gly Ser Asn Glu Gly Leu Thr Thr Thr Asp Lys Val Ile Asn Asn
            530                 535                 540
Cys Lys Val Asp Gln Cys His Ala Ala Val Thr Asn His Lys Lys Trp
545                 550                 555                 560
Gln Tyr Asn Ser Pro Leu Val Pro Arg Asn Ala Glu Leu Gly Asp Arg
            565                 570                 575
Lys Gly Lys Ile His Ile Pro Phe Pro Leu Ala Asn Val Thr Cys Arg
            580                 585                 590
Val Pro Lys Ala Arg Asn Pro Thr Val Thr Tyr Gly Lys Asn Gln Val
            595                 600                 605
Ile Met Leu Leu Tyr Pro Asp His Pro Thr Leu Leu Ser Tyr Arg Asn
            610                 615                 620
Met Gly Glu Glu Pro Asn Tyr Gln Glu Glu Trp Val Met His Lys Lys
625                 630                 635                 640
Glu Val Val Leu Thr Val Pro Thr Glu Gly Leu Glu Val Thr Trp Gly
            645                 650                 655
Asn Asn Glu Pro Tyr Lys Tyr Trp Pro Gln Leu Ser Thr Asn Gly Thr
            660                 665                 670
Ala His Gly His Pro His Glu Ile Ile Leu Tyr Tyr Tyr Glu Leu Tyr
            675                 680                 685
Pro Thr Met Thr Val Val Val Ser Val Ala Thr Phe Ile Leu Leu
            690                 695                 700
Ser Met Val Gly Met Ala Ala Gly Met Cys Met Cys Ala Arg Arg Arg
705                 710                 715                 720
Cys Ile Thr Pro Tyr Glu Leu Thr Pro Gly Ala Thr Val Pro Phe Leu
            725                 730                 735
Leu Ser Leu Ile Cys Cys Ile Arg Thr Ala Lys Ala Ala Thr Tyr Gln
            740                 745                 750
Glu Ala Ala Ile Tyr Leu Trp Asn Glu Gln Gln Pro Leu Phe Trp Leu
            755                 760                 765
Gln Ala Leu Ile Pro Leu Ala Ala Leu Ile Val Leu Cys Asn Cys Leu
            770                 775                 780
Arg Leu Leu Pro Cys Cys Cys Lys Thr Leu Ala Phe Leu Ala Val Met
785                 790                 795                 800
Ser Val Gly Ala His Thr Val Ser Ala Tyr Glu His Val Thr Val Ile
            805                 810                 815
Pro Asn Thr Val Gly Val Pro Tyr Lys Thr Leu Val Asn Arg Pro Gly
            820                 825                 830
Tyr Ser Pro Met Val Leu Glu Met Glu Leu Leu Ser Val Thr Leu Glu
            835                 840                 845
```

```
Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro Phe Gly Ala Gly Arg Pro Gly Gln
        995                 1000                1005

Phe Gly Asp Ile Gln Ser Arg Thr Pro Glu Ser Lys Asp Val Tyr
    1010                1015                1020

Ala Asn Thr Gln Leu Val Leu Gln Arg Pro Ala Val Gly Thr Val
    1025                1030                1035

His Val Pro Tyr Ser Gln Ala Pro Ser Gly Phe Lys Tyr Trp Leu
    1040                1045                1050

Lys Glu Arg Gly Ala Ser Leu Gln His Thr Ala Pro Phe Gly Cys
    1055                1060                1065

Gln Ile Ala Thr Asn Pro Val Arg Ala Val Asn Cys Ala Val Gly
    1070                1075                1080

Asn Met Pro Ile Ser Ile Asp Ile Pro Glu Ala Ala Phe Thr Arg
    1085                1090                1095

Val Val Asp Ala Pro Ser Leu Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Ala Ala Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245
```

<210> SEQ ID NO 29
<211> LENGTH: 1170
<212> TYPE: DNA
<213> ORGANISM: Artificial Sequence
<220> FEATURE:
<223> OTHER INFORMATION: soluble glycoprotein E2 without stem region strain 06.49
<220> FEATURE:
<221> NAME/KEY: CDS
<222> LOCATION: (1)..(1170)

<400> SEQUENCE: 29

```
cgt acg atg agt ctt gcc atc cca gtt atg tgc ctg ttg gca aac acc        48
Arg Thr Met Ser Leu Ala Ile Pro Val Met Cys Leu Leu Ala Asn Thr
1               5                   10                  15 acg ttt cct tgc tcc cag gac aac ttc aat gtc tat aaa gcc aca aga        96
Thr Phe Pro Cys Ser Gln Asp Asn Phe Asn Val Tyr Lys Ala Thr Arg
            20                  25                  30 cca tac tta gct cac tgt ccc gac tgt gga gaa ggg cac tcg tgc cat       144
Pro Tyr Leu Ala His Cys Pro Asp Cys Gly Glu Gly His Ser Cys His
        35                  40                  45 agt ccc gta gca cta gaa cgc atc aga aat gaa gcg aca gac ggg acg       192
Ser Pro Val Ala Leu Glu Arg Ile Arg Asn Glu Ala Thr Asp Gly Thr
    50                  55                  60 ctg aaa atc cag gtc tcc ttg caa atc gga ata aag acg gat gac agc       240
Leu Lys Ile Gln Val Ser Leu Gln Ile Gly Ile Lys Thr Asp Asp Ser
65                  70                  75                  80 cac gat tgg acc aag ctg cgt tat atg gac aac cac atg cca gca gac       288
His Asp Trp Thr Lys Leu Arg Tyr Met Asp Asn His Met Pro Ala Asp
                85                  90                  95 gca gag agg gcg ggg cta ttt gta aga aca tca gca ccg tgt acg att       336
Ala Glu Arg Ala Gly Leu Phe Val Arg Thr Ser Ala Pro Cys Thr Ile
            100                 105                 110 act gga aca atg gga cac ttc atc ctg gcc cga tgt ccc aaa ggc gaa       384
Thr Gly Thr Met Gly His Phe Ile Leu Ala Arg Cys Pro Lys Gly Glu
        115                 120                 125 act ctg acg gtg gga ttc act gac agt agg aag att agt cac tca tgt       432
Thr Leu Thr Val Gly Phe Thr Asp Ser Arg Lys Ile Ser His Ser Cys
    130                 135                 140 acg cac cca ttt cac cac gac cct cct gtg ata ggt cgg gag aaa ttc       480
Thr His Pro Phe His His Asp Pro Pro Val Ile Gly Arg Glu Lys Phe
145                 150                 155                 160 cat tcc cga ccg cag cac ggt aaa gag cta cct tgc agc acc tac gtg       528
His Ser Arg Pro Gln His Gly Lys Glu Leu Pro Cys Ser Thr Tyr Val
                165                 170                 175 cag agc acc gcc gca act acc gag gag ata gag gta cac atg ccc cca       576
Gln Ser Thr Ala Ala Thr Thr Glu Glu Ile Glu Val His Met Pro Pro
            180                 185                 190 gac acc cct gat cgc aca tta atg tca caa cag tcc ggc aac gta aag       624
Asp Thr Pro Asp Arg Thr Leu Met Ser Gln Gln Ser Gly Asn Val Lys
        195                 200                 205 atc aca gtc aat ggc cag acg gtg cgg tac aag tgt aat tgc ggt ggc       672
Ile Thr Val Asn Gly Gln Thr Val Arg Tyr Lys Cys Asn Cys Gly Gly
    210                 215                 220 tca aat gaa gga cta aca act aca gac aaa gtg att aat aac tgc aag       720
Ser Asn Glu Gly Leu Thr Thr Thr Asp Lys Val Ile Asn Asn Cys Lys
225                 230                 235                 240 gtt gat caa tgt cat gcc gcg gtc acc aat cac aaa aag tgg cag tat       768
Val Asp Gln Cys His Ala Ala Val Thr Asn His Lys Lys Trp Gln Tyr
                245                 250                 255 aac tcc cct ctg gtc ccg cgt aat gct gaa ctt ggg gac agg aaa gga       816
Asn Ser Pro Leu Val Pro Arg Asn Ala Glu Leu Gly Asp Arg Lys Gly
```

```
                Asn Ser Pro Leu Val Pro Arg Asn Ala Glu Leu Gly Asp Arg Lys Gly
                                260                 265                 270 aaa att cac atc ccg ttt ccg ctg gca aat gta aca tgc agg gtg cct            864
Lys Ile His Ile Pro Phe Pro Leu Ala Asn Val Thr Cys Arg Val Pro
            275                 280                 285 aaa gca agg aac ccc acc gtg acg tat ggc aaa aac caa gtc atc atg            912
Lys Ala Arg Asn Pro Thr Val Thr Tyr Gly Lys Asn Gln Val Ile Met
        290                 295                 300 cta ctg tat cct gac cac cca aca ctc ctg tcc tac cgg aat atg gga            960
Leu Leu Tyr Pro Asp His Pro Thr Leu Leu Ser Tyr Arg Asn Met Gly
305                 310                 315                 320 gaa gaa cca aac tat caa gaa gag tgg gtg atg cat aag aag gaa gtc           1008
Glu Glu Pro Asn Tyr Gln Glu Glu Trp Val Met His Lys Lys Glu Val
                325                 330                 335 gtg cta acc gtg ccg act gaa ggg ctc gag gtc acg tgg ggc aac aac           1056
Val Leu Thr Val Pro Thr Glu Gly Leu Glu Val Thr Trp Gly Asn Asn
            340                 345                 350 gag ccg tat aag tat tgg ccg cag tta tct aca aac ggt aca gcc cat           1104
Glu Pro Tyr Lys Tyr Trp Pro Gln Leu Ser Thr Asn Gly Thr Ala His
        355                 360                 365 ggc cac ccg cac gag ata att ctg tat tat tat gag ctg tac ccc act           1152
Gly His Pro His Glu Ile Ile Leu Tyr Tyr Tyr Glu Leu Tyr Pro Thr
370                 375                 380 atg act taa tag gcg cgc                                                   1170
Met Thr     Ala Arg
385

<210> SEQ ID NO 30
<211> LENGTH: 386
<212> TYPE: PRT
<213> ORGANISM: Artificial Sequence
<220> FEATURE:
<223> OTHER INFORMATION: Synthetic Construct

<400> SEQUENCE: 30

Arg Thr Met Ser Leu Ala Ile Pro Val Met Cys Leu Leu Ala Asn Thr
1               5                   10                  15

Thr Phe Pro Cys Ser Gln Asp Asn Phe Asn Val Tyr Lys Ala Thr Arg
            20                  25                  30

Pro Tyr Leu Ala His Cys Pro Asp Cys Gly Glu Gly His Ser Cys His
        35                  40                  45

Ser Pro Val Ala Leu Glu Arg Ile Arg Asn Glu Ala Thr Asp Gly Thr
    50                  55                  60

Leu Lys Ile Gln Val Ser Leu Gln Ile Gly Ile Lys Thr Asp Asp Ser
65                  70                  75                  80

His Asp Trp Thr Lys Leu Arg Tyr Met Asp Asn His Met Pro Ala Asp
                85                  90                  95

Ala Glu Arg Ala Gly Leu Phe Val Arg Thr Ser Ala Pro Cys Thr Ile
            100                 105                 110

Thr Gly Thr Met Gly His Phe Ile Leu Ala Arg Cys Pro Lys Gly Glu
        115                 120                 125

Thr Leu Thr Val Gly Phe Thr Asp Ser Arg Lys Ile Ser His Ser Cys
    130                 135                 140

Thr His Pro Phe His His Asp Pro Pro Val Ile Gly Arg Glu Lys Phe
145                 150                 155                 160

His Ser Arg Pro Gln His Gly Lys Glu Leu Pro Cys Ser Thr Tyr Val
                165                 170                 175

Gln Ser Thr Ala Ala Thr Thr Glu Glu Ile Glu Val His Met Pro Pro
```

|     |     |     |     |     | 180 |     |     |     | 185 |     |     |     |     | 190 |
| --- | --- | --- | --- | --- | --- | --- | --- | --- | --- | --- | --- | --- | --- | --- |
| Asp | Thr | Pro | Asp | Arg | Thr | Leu | Met | Ser | Gln | Gln | Ser | Gly | Asn | Val | Lys |
|     |     |     | 195 |     |     |     |     | 200 |     |     |     |     | 205 |     |     |
| Ile | Thr | Val | Asn | Gly | Gln | Thr | Val | Arg | Tyr | Lys | Cys | Asn | Cys | Gly | Gly |
|     |     | 210 |     |     |     |     | 215 |     |     |     |     | 220 |     |     |     |
| Ser | Asn | Glu | Gly | Leu | Thr | Thr | Thr | Asp | Lys | Val | Ile | Asn | Asn | Cys | Lys |
| 225 |     |     |     |     | 230 |     |     |     |     | 235 |     |     |     |     | 240 |
| Val | Asp | Gln | Cys | His | Ala | Ala | Val | Thr | Asn | His | Lys | Lys | Trp | Gln | Tyr |
|     |     |     |     | 245 |     |     |     |     | 250 |     |     |     |     | 255 |     |
| Asn | Ser | Pro | Leu | Val | Pro | Arg | Asn | Ala | Glu | Leu | Gly | Asp | Arg | Lys | Gly |
|     |     |     | 260 |     |     |     |     | 265 |     |     |     |     | 270 |     |     |
| Lys | Ile | His | Ile | Pro | Phe | Pro | Leu | Ala | Asn | Val | Thr | Cys | Arg | Val | Pro |
|     |     | 275 |     |     |     |     | 280 |     |     |     |     | 285 |     |     |     |
| Lys | Ala | Arg | Asn | Pro | Thr | Val | Thr | Tyr | Gly | Lys | Asn | Gln | Val | Ile | Met |
|     | 290 |     |     |     |     | 295 |     |     |     |     | 300 |     |     |     |     |
| Leu | Leu | Tyr | Pro | Asp | His | Pro | Thr | Leu | Leu | Ser | Tyr | Arg | Asn | Met | Gly |
| 305 |     |     |     |     | 310 |     |     |     |     | 315 |     |     |     |     | 320 |
| Glu | Glu | Pro | Asn | Tyr | Gln | Glu | Trp | Val | Met | His | Lys | Lys | Glu | Val |
|     |     |     |     | 325 |     |     |     |     | 330 |     |     |     |     | 335 |
| Val | Leu | Thr | Val | Pro | Thr | Glu | Gly | Leu | Glu | Val | Thr | Trp | Gly | Asn | Asn |
|     |     |     | 340 |     |     |     |     | 345 |     |     |     |     | 350 |     |     |
| Glu | Pro | Tyr | Lys | Tyr | Trp | Pro | Gln | Leu | Ser | Thr | Asn | Gly | Thr | Ala | His |
|     |     |     | 355 |     |     |     |     | 360 |     |     |     |     | 365 |     |     |
| Gly | His | Pro | His | Glu | Ile | Ile | Leu | Tyr | Tyr | Glu | Leu | Tyr | Pro | Thr |
|     | 370 |     |     |     |     | 375 |     |     |     |     | 380 |     |     |     |

Met Thr
385

<210> SEQ ID NO 31
<211> LENGTH: 3762
<212> TYPE: DNA
<213> ORGANISM: Artificial Sequence
<220> FEATURE:
<223> OTHER INFORMATION: proteins C-E3-E2-6K-E1 strain 06.49

<400> SEQUENCE: 31

```
cgtacgatgg agttcatccc aacccaaact ttttacaata ggaggtacca gcctcgaccc      60
tggactccgc gccctactat ccaagtcatc aggccccaga cgcgccctca gaggcaagct    120
gggcaacttg cccagctgat ctcagcagtt aataaactga caatgagagc ggtaccccaa    180
cagaagccac gcaggaatcg aagaataag aagcaaaagc aaaaacaaca ggcgccacaa    240
aacaacacaa atcaaaagaa gcagccacct aaaagaaac cggctcaaaa gaaaaagaag    300
ccgggccgca gagagaggat gtgcatgaaa atcgaaaatg attgtatttt cgaagtcaag    360
cacgaaggta aggtaacagg ttacgcgtgc ctggtggggg acaaagtaat gaaaccagca    420
cacgtcaagg gcaccatcga taacgcggac ctggccaaac tggcctttaa gcggtcatct    480
aagtatgacc ttgaatgcgc tcagataccc gtgcacatga agtccgacgc ttcgaagttc    540
acccatgaga aaccggaggg gtactacaac tggcaccacg agcagtacag tactcagga    600
ggccggttca ccatccctac aggtgctggc aaaccagggg acagcggcag accgatcttc    660
gacaacaagg gacgcgtggt ggccatagtc ttaggaggag ctaatgaagg agcccgtaca    720
gccctctcgg tggtgacctg gaataaagac attgtcacta aaatcacccc cgagggggcc    780
gaagagtgga gtcttgccat cccagttatg tgcctgttgg caaacaccac gttcccatgc    840
```

```
tcccagccac cttgcacgcc ctgctgctac gagaaggaac cggaggaaac cctacgcatg    900
cttgaggaca acgtcatgag acctgggtac tatcagctgc tacaagcatc cttaacatgt    960
tctccccacc gccagcgacg cagcaccaag acaacttca atgtctataa agccacaaga   1020
ccatacttag ctcactgtcc cgactgtgga aagggcact cgtgccatag tcccgtagca    1080
ctagaacgca tcagaaatga agcgacagac gggacgctga aaatccaggt ctccttgcaa    1140
atcggaataa agacggatga cagccacgat tggaccaagc tgcgttatat ggacaaccac    1200
atgccagcag acgcagagag ggcggggcta tttgtaagaa catcagcacc gtgtacgatt    1260
actggaacaa tggacactt catcctggcc cgatgtccta aaggcgaaac tctgacggtg     1320
ggattcactg acagtaggaa gattagtcac tcatgtacgc acccatttca ccacgaccct    1380
cctgtgatag gtcgggagaa attccattcc cgaccgcagc acggtaaaga gctaccttgc    1440
agcacctacg tgcagagcac cgccgcaact accgaggaga tagaggtaca catgccccca    1500
gacacccctg atcgcacatt aatgtcacaa cagtccggca acgtaaagat cacagtcaat    1560
ggccagacgg tgcggtacaa gtgtaattgc ggtggctcaa atgaaggact aacaactaca    1620
gacaaagtga ttaataactg caaggttgat caatgtcatg ccgcggtcac caatcacaaa    1680
aagtggcagt ataactcccc tctggtcccg cgtaatgctg aacttgggga ccggaaagga    1740
aaaattcaca tcccgtttcc gctggcaaat gtaacatgca gggtgcctaa agcaaggaac    1800
cccaccgtga cgtatggcaa aaaccaagtc atcatgctac tgtatcctga ccacccaaca    1860
ctcctgtcct accggaatat gggagaagaa ccaaactatc aagaagagtg ggtgatgcat    1920
aagaaggaag tcgtgctaac cgtgccgact gaagggctcg aggtcacgtg gggcaacaac    1980
gagccgtata agtattggcc gcagttatct acaaacggta cagcccatgg ccacccgcac    2040
gagataattc tgtattatta tgagctgtac cccactatga ctgtagtagt tgtgtcagtg    2100
gccacgttca tactcctgtc gatggtgggt atggcagcgg ggatgtgcat gtgtgcacga    2160
cgcagatgca tcacaccgta tgaactgaca ccaggagcta ccgtcccatt cctgcttagc    2220
ctaatatgct gcatcagaac agctaaagcg gccacatacc aagaggctgc gatatacctg    2280
tggaacgagc agcaaccttt gttttggcta caagcccctta ttccgctggc agccctgatt    2340
gttctatgca actgtctgag actcttacca tgctgctgta aaacgttggc tttttttagcc    2400
gtaatgagcg tcggtgccca cactgtgagc gcttacgaac acgtaacagt gatcccgaac    2460
acggtgggag taccgtataa gactctagtc aatagacctg gctacagccc catggtattg    2520
gagatggaac tactgtcagt cactttggag ccaaacactat cgcttgatta catcacgtgc    2580
gagtacaaaa ccgtcatccc gtctccttac gtgaagtgct gcggtacagc agagtgcaag    2640
gacaaaaacc tacctgacta cagctgtaag gtcttcaccg cgtctaccc atttatgtgg    2700
ggcggcgcct actgcttctg cgacgctgaa aacacgcagt tgagcgaagc acacgtggag    2760
aagtccgaat catgcaaaac agaatttgca tcagcataca gggctcatac cgcatctgca    2820
tcagctaagc tccgcgtcct ttaccaagga aataacatca ctgtaactgc ctatgcaaac    2880
ggcgaccatg ccgtcacagt taaggacgcc aaattcattg tggggccaat gtcttcagcc    2940
tggacacctt tcgacaacaa aattgtggtg tacaaaggtg acgtctataa catgactac     3000
ccgcccttcg gcgcaggaag accaggacaa tttggcgata tccaaagtcg cacacctgag    3060
agtaaagacg tctatgctaa tacacaactg gtactgcaga accggctgt gggtacggta    3120
cacgtgccat actctcaggc accatctggc tttaagtatt ggctaaaaga acgcggggcg    3180
tcgctgcagc acacagcacc atttggctgc caaatagcaa caaacccggt aagagcggtg    3240
```

```
aactgcgccg tagggaacat gcccatctcc atcgacatac cggaagcggc cttcactagg    3300
gtcgtcgacg cgccctcttt aacggacatg tcgtgcgagg taccagcctg cacccattcc    3360
tcagactttg ggggcgtcgc cattattaaa tatgcagcca gcaagaaagg caagtgtgcg    3420
gtgcattcga tgactaacgc cgtcactatt cgggaagctg agatagaagt tgaagggaat    3480
tctcagctgc aaatctcttt ctcgacggcc ttagccagcg ccgaattccg cgtacaagtc    3540
tgttctacac aagtacactg tgcagccgag tgccaccccc cgaaggacca catagtcaac    3600
tacccggcgt cacataccac cctcggggtc caggacatct ccgctacggc gatgtcatgg    3660
gtgcagaaga tcacgggagg tgtgggactg gttgttgctg ttgccgcact gattctaatc    3720
gtggtgctat gcgtgtcgtt cagcaggcac taataggcgc gc                      3762

<210> SEQ ID NO 32
<211> LENGTH: 54
<212> TYPE: DNA
<213> ORGANISM: Artificial Sequence
<220> FEATURE:
<223> OTHER INFORMATION: Nucleotide sequence of E2 EP3
<220> FEATURE:
<221> NAME/KEY: CDS
<222> LOCATION: (1)..(54)

<400> SEQUENCE: 32 agc acc aag gac aac ttc aat gtc tat aaa gcc aca aga cca tac tta    48
Ser Thr Lys Asp Asn Phe Asn Val Tyr Lys Ala Thr Arg Pro Tyr Leu
1               5                   10                  15 gct cac                                                             54
Ala His

<210> SEQ ID NO 33
<211> LENGTH: 18
<212> TYPE: PRT
<213> ORGANISM: Artificial Sequence
<220> FEATURE:
<223> OTHER INFORMATION: Synthetic Construct

<400> SEQUENCE: 33

Ser Thr Lys Asp Asn Phe Asn Val Tyr Lys Ala Thr Arg Pro Tyr Leu
1               5                   10                  15

Ala His
```